(12) United States Patent
Brownell et al.

(10) Patent No.: US 11,123,393 B2
(45) Date of Patent: *Sep. 21, 2021

(54) COMPOSITIONS AND METHODS FOR JOINT HEALTH

(71) Applicants: Unigen, Inc., Seattle, WA (US); Unigen, Inc., Cheonan-si (KR)

(72) Inventors: Lidia Alfaro Brownell, Tacoma, WA (US); Min Chu, Newcastle, WA (US); Mei-Feng Hong, Lacey, WA (US); Eu-Jin Hyun, Cheonan-si (KR); Qi Jia, Olympia, WA (US); Ping Jiao, Newcastle, WA (US); Hyun-Jin Kim, Asan-si (KR); Mi-Ran Kim, Daejeon (KR); Tae-Woo Kim, Ulsan (KR); Bo-Su Lee, Pohang-si (KR); Young-Chul Lee, Daejeon (KR); Breanna Moore, Seattle, WA (US); Jeong-Bum Nam, Ochang-eup (KR); Mi-Sun Oh, Cheonan-si (KR); Mi-Hye Park, Daegu (KR); Mesfin Yimam, Tacoma, WA (US); Qian Zhang, Seoul (KR)

(73) Assignee: Unigen, Inc., Tacoma, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/305,839

(22) Filed: Jun. 16, 2014

(65) Prior Publication Data
US 2015/0072953 A1 Mar. 12, 2015

Related U.S. Application Data

(60) Provisional application No. 61/836,113, filed on Jun. 17, 2013, provisional application No. 61/895,234, filed on Oct. 24, 2013.

(51) Int. Cl.
| | |
|---|---|
| *A61K 36/605* | (2006.01) |
| *A61K 36/48* | (2006.01) |
| *A61K 31/7008* | (2006.01) |
| *A61K 36/534* | (2006.01) |
| *A61K 31/05* | (2006.01) |
| *A61K 31/352* | (2006.01) |
| *A61K 31/353* | (2006.01) |
| *A61K 31/7028* | (2006.01) |
| *A61K 31/7034* | (2006.01) |

(52) U.S. Cl.
CPC ............ *A61K 36/605* (2013.01); *A61K 31/05* (2013.01); *A61K 31/352* (2013.01); *A61K 31/353* (2013.01); *A61K 31/7008* (2013.01); *A61K 31/7028* (2013.01); *A61K 31/7034* (2013.01); *A61K 36/48* (2013.01); *A61K 36/534* (2013.01)

(58) Field of Classification Search
None
See application file for complete search history.

(56) References Cited

U.S. PATENT DOCUMENTS

| | | | |
|---|---|---|---|
| 7,514,469 B2 | 4/2009 | Jia | |
| 8,192,768 B2 | 6/2012 | Gokaraju et al. | |
| 2004/0185122 A1* | 9/2004 | Obukowicz | ........... A23L 1/3002 424/725 |
| 2006/0269627 A1* | 11/2006 | Jia | ........................ A61K 31/33 424/757 |
| 2008/0286213 A1* | 11/2008 | Shi | ........................ A61K 8/498 424/49 |
| 2012/0135094 A1 | 5/2012 | Simon | |

FOREIGN PATENT DOCUMENTS

| | | |
|---|---|---|
| WO | 2006099217 | 9/2006 |
| WO | WO 2007/139887 | * 12/2007 |

OTHER PUBLICATIONS

Andallu, B. et al "Effect of mulberry (Morus indica L.) therapy . . . " Clin. Chim. Acta (2001) vol. 314, pp. 47-53.*
Ferlinahayati, Y. et al "Phenolic constituents from the wood of Morus . . . " Z. Naturforsch. (2008) vol. 63c, pp. 35-39.*
Jaraid, E. et al "Biochemical study of the hypoglycaemic effects . . . " Int. J. Diab. Metab. (2009) vol. 17, pp. 63-69.*
Zheng, Z. et al "Tyrosinase ihibitory constituents from the roots of Morus nigra . . . " J. Agric. Food Chem. (2010) vol. 58, pp. 5368-5373.*
Song, W. et al "Phytochemical profiles of different mulberry . . . " J. Agric. Food Chem. (2009) vol. 57, pp. 9133-9140.*
Chung, K. et al "In vitro and in vivo anti-inflammatory effect . . . " J. Pharm. Pharmacol. (2003) vol. 55, pp. 1695-1700.*

(Continued)

*Primary Examiner* — Leigh C Maier
(74) *Attorney, Agent, or Firm* — Sandra Poteat Thompson; Finlayson Toffer Roosevelt & Lilly LLP

(57) ABSTRACT

The present disclosure provides mixtures of prenylated flavonoids, stilbenes, or both with flavans or curcuminoids or both capable of modulating joint inflammation, joint pain, joint stiffness, cartilage degradation, or improving mobility, range of motion, flexibility, joint physical function, or any combination thereof. Such a mixture of prenylated flavonoids, stilbenes, or both with flavans or curcuminoids or both can optionally be used in combination with other joint management agents, such as non-steroidal anti-inflammatory agents/analgesics, COX/LOX inhibiting agents, glucosamine compounds, neuropathic pain relief agents, or the like.

10 Claims, 1 Drawing Sheet

(56) References Cited

OTHER PUBLICATIONS

Kimura, Y. et al "Effects of phenolic constitutents from the mulberry . . . " J. Nat. Prod. (1986) vol. 49, No. 4, pp. 639-644.*
Singh, R. et al "Evaluation of antioxidant potential of ethyl acetate extract . . . " Food Chem. Toxicol., (2007) vol. 45, pp. 1216-1223.*
Clement, B. et al "Toxic amines and alkaloids . . . " Phytochem. (1998) vol. 49, No. 5, pp. 1377-1380.*
Enkhmaa, B. et al "Mulberry (Morus alba L.) leaves and their major flavonol . . . " J. Nutr., vol. 135, pp. 729-734. (Year: 2005).*
Guleria, S. et al "Antioxidant activity and protective effect . . . "J. Food Sci., vol. 76, No. 7, pp. C959-C964. (Year: 2011).*
Almeida, Jackson Roberto Guedes da Silva et al., "Medicinal Plants and Natural Compounds from the genus *Morus* (Moraceae) with Hypoglycemic activity: A review", In: Glucose tolerance, INTECH, Dec. 12, 2012, ISBN 978-953-51-08-1-7, Chapter 11, pp. 189-206. See p. 192, paragraphs 4-5, table 1.
Search Report for PCT/US2014/042584 dated Oct. 27, 2014.

\* cited by examiner

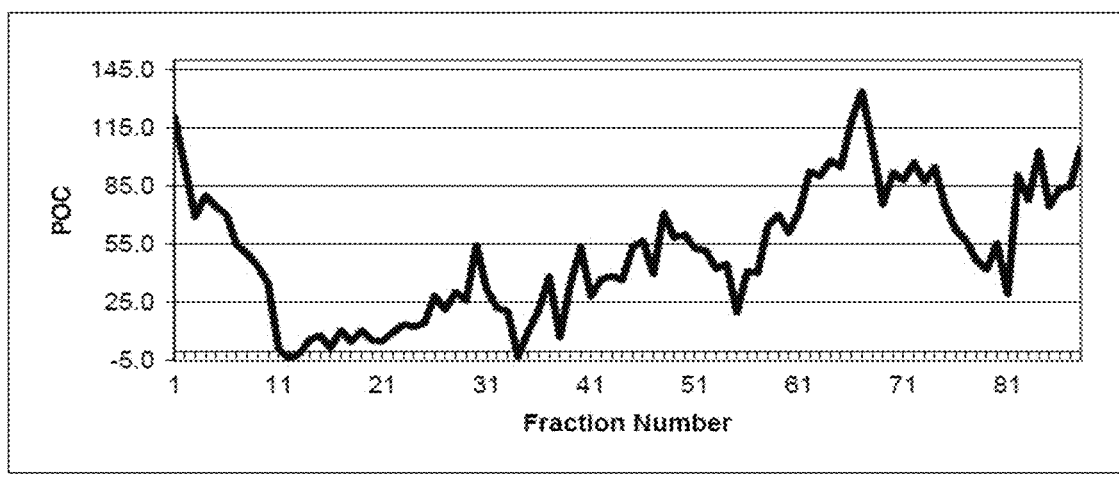

COMPOSITIONS AND METHODS FOR JOINT HEALTH

CROSS-REFERENCE TO RELATED APPLICATIONS

This application claims the benefit under 35 U.S.C. § 119(e) of U.S. Provisional Patent Application No. 61/836,113, filed Jun. 17, 2013 and U.S. Provisional Patent Application No. 61/895,234, filed Oct. 24, 2013. These applications are incorporated herein by reference in their entireties.

BACKGROUND

The most abundant heteropolysaccharides in the body are glycosaminoglycans (GAGs). They are composed of repetitive disaccharide units of a hexosamine and hexuronic acid attached through a linker oligosaccharide region to the core protein of proteoglycans. A high number of GAGs are linked to the core protein of cartilage aggrecan. GAGs are highly negatively charged molecules with extended an extended conformation that imparts viscosity to a solution. These negatively charged carbohydrates are responsible for the high swelling capacity of cartilage. GAGs are located primarily on the surface of cells or in the extracellular matrix (ECM). GAGs are important molecular constituents of both cell surface proteoglycans, as well as large and small proteoglycans of the extracellular matrix of cartilage. Along with high viscosity of GAGs comes low compressibility, which makes these molecules ideal for a lubricating fluid in the joints. At the same time, their rigidity provides structural integrity to cells and provides passageways between cells.

Glycosaminoglycan is a major component of joint cartilage, joint fluid, and other soft connective tissue. The glycosaminoglycans (GAGs) of articular cartilage have been identified as chondroitin 6-sulfate, chondroitin 4-sulfate, dermatan sulfate, heparin, heparin sulfate and keratin sulfate. GAGs are released from the degrading cartilage matrix in large amounts during inflammation of the joints. Changes in the levels or molecular nature of GAGs have been associated with some connective tissue diseases. For example, patients with arthritis and scleroderma have elevated concentrations of GAGs in blood and synovial fluid, and destruction of involved joints in arthritis patients correlates positively with high GAG levels in synovial fluid. Histochemical and biochemical studies of cartilage from arthritic joints have shown a significant decrease in the GAG content and that the decrease in approximately proportional to the severity of the disease.

*Morus alba* L (Moraceae), the mulberry or white berry plant, is native to northern China, and has been cultivated and naturalized elsewhere, from India to the Middle East to Southern Europe, and recently to the North American area. The root-bark is used in traditional medicine known as Sang bai pi or Cortex Mori (Pharmacopoeia of the People's Republic of China, 2005). This herb is also known as Pong-na-moo in Korean and Sohakuhi in Japan. In contemporary pharmacological research, *Morus alba* root-bark has been reported to have antibacterial, anti-viral, antioxidant, hypoglycemic, hypolipidemic, neuroprotective, antiulcer, analgesic and anti-inflammatory activities. A variety of bioactive compounds from *Morus alba* root-bark have in vivo and in vitro anti-inflammatory activity.

*Acacia* is a genus of leguminous trees and shrubs. The genus *Acacia* includes more than 1000 species belonging to the family of Leguminosae and the subfamily of Mimosoideae. *Acacias* are distributed worldwide in tropical and subtropical areas of Central and South America, Africa, parts of Asia, as well as Australia, which has the largest number of endemic species. *Acacias* occur primarily in dry and arid regions, where the forests are often in the nature of open thorny shrubs. *Acacias* are very important economically, providing a source of tannins, gums, timber, fuel and fodder. Tannins, which are isolated primarily from bark, are used extensively for tanning hides and skins Some *Acacia* barks are also used for flavoring local spirits. Some indigenous species like *A. sinuata* also yield saponins, which are used in detergents, foaming agents and emulsifiers. The flowers of some *Acacia* species are fragrant and used to make perfume. The heartwood of many *Acacias* is used for making agricultural implements and also provides a source of firewood. *Acacia* gums find extensive use in medicine and confectionary and as sizing and finishing materials in the textile industry.

*Uncaria gambir* (Rubiaceae) is a climbing shrub with round branches, which is believed to strengthen teeth when chewed with piper bettle leaves. All parts of the plant have astringent properties. Leaves of the *U. gambir* plant contain free catechins as well as polymerized catechins—tannins—which are more abundant in younger leaves as compared to older leaves. *U. gambir* is listed in the Food Additive Database in EAFUS (Everything Added to Food in the United States), in the Korea Food Additives Code by KFDA, and in the Japan Food Additives Code by MHLW as a natural flavoring agent. *U. gambir* is also listed in the Korea Pharmaceutical Codex (KP), Japan Pharmaceutical Codex (JP) and China Pharmaceutical Codex (CP). In South Korea, there are many over-the-counter (OTC) drugs that contain *U. gambir* extract, especially for dyspepsia, halitosis, vomiting and anorexia. In Japan, *U. gambir* is used for diarrhea, vomiting and gastritis. In the United States, *U. gambir* is used as a dietary supplement to support liver function and fat metabolism.

*Curcuma longa* L, with common name as turmeric, is a perennial plant of the ginger family, Zingiberaceae. The name of turmeric might come from Latin, terra merita (merited earth) or turmeryte, which is related to saffron. It is originally from tropical south Asia and cultivated extensively in India and Southeast Asia. Turmeric is prepared from the ground rhizome and has been used in India for thousands of years. Besides its culinary usage, modern research has revealed that turmeric has antibacterial, antioxidant, chemopreventive, chemotherapeutic, antiproliferative, antiparasitic, anti-antimalarial, antinociceptive, and anti-inflammatory properties.

BRIEF SUMMARY

In brief, the present disclosure is directed to compounds and compositions useful for joint health management, including stereoisomers, pharmaceutically or nutraceutically acceptable salts, tautomers, glycosides and prodrugs of the disclosed compounds, and to related methods of improving joint health.

In certain embodiments, this disclosure provides a composition comprising a mixture of a *Morus* extract, optionally enriched for one or more prenylated flavonoids (e.g., Diels-Alder adducts of a chalcone and a prenylphenyl moiety), or one or more stilbenes, or a combination thereof, and an *Acacia* extract, optionally enriched for flavans. In further embodiments, this disclosure provides a composition comprising a mixture of a *Morus* extract, optionally enriched for prenylated flavonoids (e.g., Diels-Alder adducts of a chalcone and a prenylphenyl moiety), or one or more stilbenes, or a combination thereof, and an *Uncaria gambir* extract, optionally enriched for flavans. In further embodiments, this disclosure provides a composition comprising a mixture of a *Morus* extract enriched for one or more prenylated flavonoids (e.g., Diels-Alder adducts of a chalcone and a prenylphenyl moiety), or one or more stilbenes, or a combination thereof, and a *Curcuma* extract. In other embodiments, this disclosure provides a composition comprising a mixture of a *Morus* extract enriched for one or more prenylated flavonoids (e.g., Diels-Alder adducts of a chalcone and a prenylphenyl moiety), or one or more stilbenes, and a Peppermint extract. In other embodiments, any of the compositions further, optionally, contain one or more glucosamine compounds, such as N-acetyl glucosamine.

For example, a mixture of *Curcuma* and *Morus alba* root-bark extracts in a 1:1 ratio demonstrated beneficial synergistic effects with enhanced anti-inflammatory and anti-nociceptive efficacy compared with either *Curcuma* or *Morus alba* root-bark extracts alone.

In another aspect, the present disclosure provides methods for managing joint health. In certain embodiments, the compositions of this disclosure can be used in methods for treating, preventing, or managing joint cartilage, minimizing cartilage degradation, promoting healthy joints by protecting cartilage integrity, diminishing the action of enzymes that affect joint health, improving joint movement and/or function, alleviating joint pain, alleviating joint stiffness, improving joint range of motion and/or flexibility, promote mobility, and/or any combination thereof.

These and other aspects of the invention will be apparent upon reference to the following detailed description.

BRIEF DESCRIPTION OF THE DRAWINGS

FIG. 1 shows the inhibition of BKB1 receptor binding by *Curcuma longa* 88 HTP fractions.

DETAILED DESCRIPTION

In certain aspects, the present disclosure provides prenylated flavonoids and resveratrol compounds mixed with flavans or curcuminoids for use in improving joint health. In certain embodiments, prenylated flavonoids and resveratrol compounds are extracted *Morus alba*, such as from the *Morus alba* root. In yet another embodiment, a *Morus* extract combined with flavans is optionally further combined with other joint health management agents, such as non-steroidal anti-inflammatory agents/analgesics, COX/LOX inhibiting agents such as acetaminophen, ibuprofen, celecoxib, *Boswellia* extract, glucosamine compounds such as glucosamine sulfate, glucosamine hydrochloride, N-acetylglucosamine, chondroitin sulfate and methylsulfonylmethane, hyaluronic acid, ω-3 fatty acids (such as eicosapentaenoic acid, EPA and docosahexaenoic acid, DHA), hydrolyzed collagen (e.g., from bovine type I collagen, chicken sternal type II collagen), collagen derived peptides or a mixture of collagen amino acids, xanthophyll carotenoids (e.g., astaxanthin, which is distributed in marine bacteria, algae, crustaceans, fish), multivitamins and minerals such as vitamin D and calcium fructoborate, neuropathic pain relief agents, herbal and/or plant extracts promoting joint health, or dietary supplements that promote joint health.

Other embodiments relate to methods of use of the compositions of this disclosure, such as maintaining joint cartilage, minimizing cartilage degradation, promoting healthy joints by protecting cartilage integrity, diminishing the action of enzymes that affect joint health, improving joint movement and/or function, alleviating joint pain, alleviating joint discomfort, alleviating joint pain and discomfort, alleviating joint stiffness, improving joint range of motion and/or flexibility, promote mobility, or the like.

In the following description, certain specific details are set forth in order to provide a thorough understanding of various embodiments of this disclosure. However, one skilled in the art will understand that the invention may be practiced without these details.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. Unless the context requires otherwise, throughout the present specification and claims, the word "comprise" and variations thereof, such as, "comprises" and "comprising," as well as synonymous terms like "include" and "have" and variants thereof, are to be construed in an open, inclusive sense; that is, as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ radical.
"Cyano" refers to the —CN radical.
"Hydroxy" or "hydroxyl" refers to the —OH radical.
"Imino" refers to the =NH substituent.
"Nitro" refers to the —NO$_2$ radical.
"Oxo" refers to the =O substituent.
"Thioxo" refers to the =S substituent.

"Alkyl" refers to a straight or branched hydrocarbon chain radical consisting solely of carbon and hydrogen atoms, which is saturated or unsaturated (i.e., contains one or more double or triple bonds), having from one to twelve carbon atoms ($C_1$-$C_{12}$ alkyl), or one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this disclosure, the aryl radical may be a monocyclic, bicyclic, tricyclic or tetracyclic ring system, which may include fused or bridged ring systems. Aryl radicals include aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, or having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —R$_b$R$_d$ where R$_b$ is an alkylene chain as defined above and R$_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of this disclosure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —R$_b$R$_e$ where R$_b$ is an alkylene chain as defined above and R$_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl or heteroarylalkyl), wherein at least one hydrogen atom is replaced by a bond to a non-hydrogen atoms such as a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom, such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl or heteroarylalkyl group. In addition, each of the foregoing substituents may also be optionally substituted with one or more of the above substituents.

"Glycoside" refers to a molecule in which a sugar group is bonded through its anomeric carbon to another group via a glycosidic bond. Exemplary sugars include glucose, rhamnose, manose, galactose, arabinose, glucuronide and others. Glycosides can be linked by an O- (an O-glycoside), N- (a glycosylamine), S- (a thioglycoside), or C- (a C-glycoside) glycosidic bond. Compounds of this disclosure can form glycosides at any suitable attachment point.

A "prenyl group" is a moiety comprising a five-carbon backbone of the following structure:

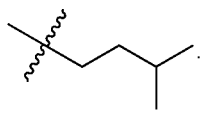 [SMILES: *CCC(C)C]

In some embodiments, prenyl groups comprise one or more carbon-carbon double bonds and/or are substituted with one or more substituents. "Prenyl" refers to the

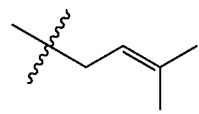 [SMILES: *CC=C(C)C]

radical. Isoprenyl refers to the

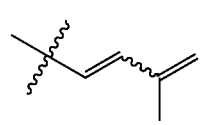 [SMILES: *C=CC(=C)C]

radical (cis or trans). Prenyl groups are substituted or unsubstituted, such as

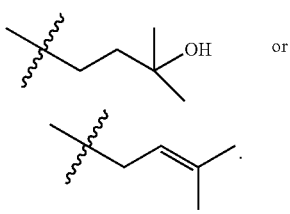

"Prenylphenyl" refers to a phenyl moiety connected to a prenyl moiety as defined above. Prenylphenyls include substituted phenyls such as flavonoids and other substituted phenyls and heteroaryls, provided there is at least one prenyl group in the molecule. In the case of substituted phenyls and heteroaryl, the prenyl moiety need not be directly attached to the phenyl ring, but can be attached at any point in the molecule.

"Chalcone" refers to a compound comprising the following core structure:

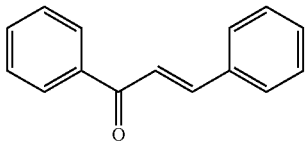 [SMILES: O=C(/C=C/c1ccccc1)c1ccccc1]

Chalcones can be variously substituted at any of the above carbon atoms.

"Prodrug" is meant to indicate a compound that may be converted under physiological conditions or by solvolysis to a biologically active compound of this disclosure. Thus, the term "prodrug" refers to a metabolic precursor of a compound of this disclosure that is pharmaceutically and nutraceutically acceptable. A prodrug may be inactive when administered to a subject in need thereof, but is converted in vivo to an active compound of this disclosure. Prodrugs are typically rapidly transformed in vivo to yield the parent compound of this disclosure, for example, by hydrolysis in blood or intestine or metabolized in the liver. The prodrug compound often offers advantages of solubility, tissue compatibility or delayed release in a mammalian organism (see Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical and Nutraceutical Association and Pergamon Press, 1987.

The term "prodrug" is also meant to include any covalently bonded carriers, which release the active compound of this disclosure in vivo when such prodrug is administered to a mammalian subject. Prodrugs of a compound of this disclosure may be prepared by modifying functional groups present in the compound of this disclosure in such a way that the modifications are cleaved, either in routine manipulation or in vivo, to the parent compound of this disclosure. Prodrugs include compounds of this disclosure wherein a hydroxy, amino or mercapto group is bonded to any group that, when the prodrug of the compound of this disclosure is administered to a mammalian subject, cleaves to form a free hydroxy, free amino or free mercapto group, respectively. Examples of prodrugs include acetate, formate and benzoate derivatives of alcohol or amide derivatives of amine functional groups in the compounds of this disclosure and the like.

The instant disclosure is also meant to encompass all pharmaceutically or nutraceutically acceptable compounds of any one of structures (I)-(VI) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of any one of structures (I)-(VI), for example, those incorporating a radioactive isotope, are useful in drug or substrate tissue distribution studies. The radioactive isotopes tritium, i.e., $^{3}H$, and carbon-14, i.e., $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of any one of structures (I)-(VI) can generally be prepared by conventional techniques known to those skilled in the art or by processes analogous to those described in the preparations and examples as set out herein using an appropriate isotopically-labeled reagent in place of the non-labeled reagent previously employed.

The instant disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, this disclosure includes compounds produced by a process comprising administering a compound of this disclosure to a mammal for a period of time sufficient to yield a metabolic product thereof. Such products are typically identified by administering a radiolabelled compound of this disclosure in a detectable dose to an animal, such as rat, mouse, guinea pig, dog, cat, pig, sheep, horse, monkey, or human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals, such as laboratory animals or household pets (e.g., rat, mouse, guinea pig, cats, dogs, swine, cattle, sheep, goats, horses, rabbits, primates), and non-domestic animals, such as wildlife or the like.

"Optional" or "optionally" means that the subsequently described element, component, event or circumstances may or may not occur, and includes instances where the element, component, event or circumstance occur and instances in which they do not. For example, "optionally substituted aryl" means that the aryl radical may or may not be substituted—in other words, the description includes both substituted aryl radicals and aryl radicals having no substitution.

"Pharmaceutically or nutraceutically acceptable carrier, diluent or excipient" includes any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically or nutraceutically acceptable salt" includes both acid and base addition salts.

"Pharmaceutically or nutraceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, or the like.

"Pharmaceutically or nutraceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include the sodium, potassium, lithium, ammonium, calcium, magnesium, iron, zinc, copper, manganese, aluminum salts and the like. In certain embodiments, the inorganic salts are ammonium, sodium, potassium, calcium, or magnesium salts. Salts derived from organic bases include salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly useful organic bases include isopropylamine, diethylamine, ethanolamine, trimethylamine, dicyclohexylamine, choline, or caffeine.

Often crystallizations produce a solvate of the compound of this disclosure. As used herein, the term "solvate" refers to an aggregate that comprises one or more molecules of a compound of this disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of this disclosure may be true solvates, while in other cases, the compound of this disclosure may merely retain adventitious water or be a mixture of water plus some adventitious solvent.

A "pharmaceutical composition" or "nutraceutical composition" refers to a formulation of a compound of this disclosure and a medium generally accepted in the art for the delivery of the biologically active compound to mammals, e.g., humans. For example, a pharmaceutical composition of the present disclosure may be formulated or used as a stand alone composition, or as a component in a prescription drug, an over-the-counter (OTC) medicine, a botanical drug, an herbal medicine, a homeopathic agent, or any other form of health care product reviewed and approved by a government agency. Exemplary nutraceutical compositions of the present disclosure may be formulated or used as a stand alone composition, or as a nutritional or bioactive component in food, a novel food, a functional food, a beverage, a bar, a food flavor, a food additive, a medical food, a dietary supplement, or an herbal product. A medium generally accepted in the art includes all pharmaceutically or nutraceutically acceptable carriers, diluents or excipients therefor.

As used herein, "enriched for" refers to a plant extract or other preparation having at least a two-fold up to about a 1000-fold increase in the amount or activity of one or more active compounds as compared to the amount or activity of the one or more active compounds found in the weight of the plant material or other source before extraction or other preparation. In certain embodiments, the weight of the plant material or other source before extraction or other preparation may be dry weight, wet weight, or a combination thereof.

As used herein, "major active ingredient" or "major active component" refers to one or more active compounds found in a plant extract or other preparation, or enriched for in a plant extract or other preparation, which is capable of at least one biological activity. In certain embodiments, a major active ingredient of an enriched extract will be the one or more active compounds that were enriched in that extract. Generally, one or more major active components will impart, directly or indirectly, most (i.e., greater than 50%) of one or more measurable biological activities or effects as compared to other extract components. In certain embodiments, a major active ingredient may be a minor component by weight percentage of an extract (e.g., less than 50%, 25%, 20%, 15%, 10%, 5%, or 1% of the components contained in an extract) but still provide most of the desired biological activity. Any composition of this disclosure containing a major active ingredient may also contain minor active ingredients that may or may not contribute to the pharmaceutical or nutraceutical activity of the enriched composition, but not to the level of major active components, and minor active components alone may not be effective in the absence of a major active ingredient.

"Effective amount" or "therapeutically effective amount" refers to that amount of a compound or composition of this disclosure that, when administered to a mammal, such as a human, is sufficient to effect treatment, including any one or more of: (1) treating or preventing loss of cartilage in a mammal; (2) promoting joint health; (3) suppressing loss of cartilage in a mammal; (4) increasing joint flexibility in a mammal; (5) treating or preventing joint pain in a mammal; (6) modifying inflammation of a joint in a mammal; and (7) increasing joint range of motion. The amount of a compound or composition of this disclosure that constitutes a "therapeutically effective amount" will vary depending on the compound, the condition being treated and its severity, the manner of administration, the duration of treatment, or the body weight and age of a subject to be treated, but can be determined by one of ordinary skill in the art having regard to his own knowledge and to this disclosure.

"Supplements" as used herein refers to a product that improves, promotes, supports, increases, regulates, manages, controls, maintains, optimizes, modifies, reduces, inhibits, or prevents a particular condition, structure or function associated with a natural state or biological process (i.e., are not used to diagnose, treat, mitigate, cure, or prevent disease). In certain embodiments, a supplement is a dietary supplement. For example, with regard to joint health-related conditions, dietary supplements may be used to maintain joint cartilage, minimize cartilage degradation, promote healthy joints by protecting cartilage integrity, diminish the action of enzymes that affect joint health, improve joint movement and/or function, support joint function, alleviate joint pain, alleviate joint discomfort, alleviate joint stiffness, improve joint range of motion, improve joint flexibility, improve joint range of motion and flexibility, promote mobility, or the like. In certain embodiments, dietary supplements are a special category of diet, food or both, and are not a drug.

"Treating" or "treatment" or "ameliorating" refers to either a therapeutic treatment or prophylactic/preventative treatment of a disease or condition of interest in a mammal, such as a human, having or suspected of having a disease or condition of interest, and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition, (e.g., relieving pain, reducing inflammation, reducing loss of cartilege) without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. In certain embodiments, the compositions and methods of the instant disclosure are used to treat, for example, osteoarthritis, rheumatoid arthritis, or both.

As used herein, "statistical significance" refers to a p value of 0.050 or less as calculated using the Students t-test and indicates that it is unlikely that a particular event or result being measured has arisen by chance.

The chemical naming protocol and structure diagrams used herein are a modified form of the I.U.P.A.C. nomenclature system, using the ACD/Name Version 9.07 software program or ChemDraw Ultra Version 11.0 software naming program (CambridgeSoft), wherein the compounds of this disclosure are named herein as derivatives of the central core structure, e.g., the imidazopyridine structure. For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

As noted herein, in certain embodiments, the present disclosure provides a composition comprising prenylated flavonoids. Flavonoids include flavans, flavones, flavonols, flavanones, flavanonols, isoflavonoids, neoflavonoids, chalcones, arylbenzofuran, or the like.

In certain embodiments, a flavonoid compound of the present disclosure has structure (III), as follows:

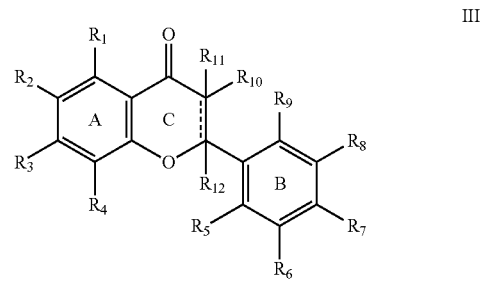

wherein $R_1$-$R_{12}$ are each independently H, hydroxyl, a prenyl group, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl, or a bond to a compound of structure (III) or (IV); or one of $R_1$-$R_{12}$ joins with another one of $R_1$-$R_{12}$ to form a ring, and the remaining $R_1$-$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl or a bond to a compound of structure (III) or (IV), provided that all valencies are satisfied (e.g., when the optional double bond is present in ring C, then $R_{12}$ is absent and at least one of $R_{10}$ or $R_{11}$ is absent). In certain embodiments, at least one of $R_1$-$R_{12}$ is a prenyl group, such as

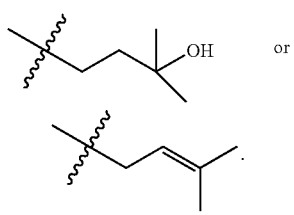

In further embodiments, the optional double bond is present in ring C, $R_{11}$ and $R_{12}$ are absent, and $R_{10}$ is a prenyl group. In still further embodiments, at least one of $R_1$-$R_9$ is a prenyl group and $R_{10}$-$R_{12}$ are independently H or hydroxyl. In certain specific embodiments, the prenylated flavonoids include Albanin G, Kuwanon G, Morusin, or any combination thereof.

In certain embodiments, a flavonoid compound of the present disclosure has structure (IV) as follows:

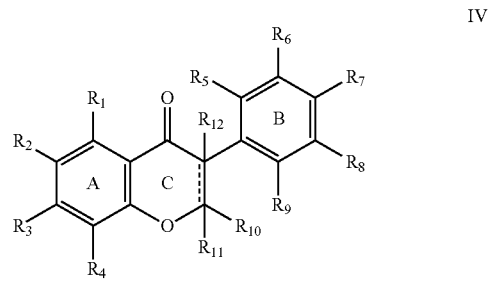

wherein $R_1$-$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkylamino, cycloalkyl, heterocyclyl, aryl, heteroaryl, aralkyl, alkylcarbonyl, aralkylcarbonyl, or a bond to a compound of structure (III) or (IV); or one of $R_1$-$R_{12}$ joins with another one of $R_1$-$R_{12}$ to form a ring, and the remaining $R_1$-$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl or a bond to a compound of structure (III) or (IV), provided that all valencies are satisfied (e.g., when the optional double bond is present in ring C, then $R_{12}$ is absent and at least one of $R_{10}$ or $R_{11}$ is absent). In certain embodiments, at least one of $R_1$-$R_{12}$ is a prenyl group, such as

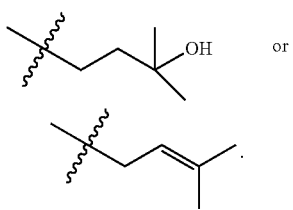

In further embodiments, the optional double bond is present in ring C, $R_{11}$ and $R_{12}$ are absent, and $R_{10}$ is a prenyl group. In still further embodiments, at least one of $R_1$-$R_9$ is a prenyl group and $R_{10}$-$R_{12}$ are independently H or hydroxyl. In certain specific embodiments, the prenylated flavonoids include Albanin G, Kuwanon G, Morusin, morusinol, Sanggenon, isoxanthoumol, glabridin, cathayanon A, or any combination thereof.

In some embodiments, a chalconoid compound of the present disclosure has structure (V) as follows:

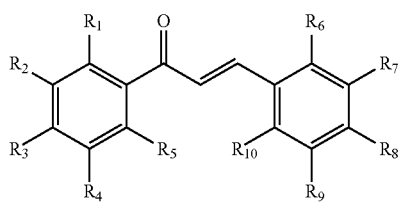

wherein $R_1$-$R_{10}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, or aralkylcarbonyl. In certain embodiments, at least one of $R_1$-$R_{10}$ is a prenyl group, such as

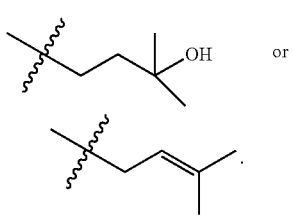

In further embodiments, the optional double bond is present in ring C, $R_{11}$ and $R_{12}$ are absent, and $R_{10}$ is a prenyl group. In still further embodiments, at least one of $R_1$-$R_9$ is a prenyl group and $R_{10}$-$R_{12}$ are independently H or hydroxyl. In certain specific embodiments, a chalconoid compound includes xanthohumol.

In certain embodiments, a stilbene compound of the present disclosure is an (E)-stilbene (trans isomer) structure of formula I or (Z)-stilbene (cis isomer) structure of formula II, as follows:

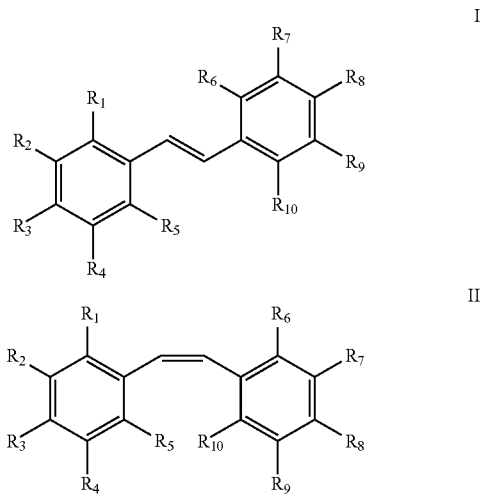

wherein $R_1$-$R_{10}$ are each independently H, hydroxyl, glycoside, a prenyl group, flavonoid, chalcone, halogen, sulfhydryl, amino, aldehyde, $C_{1-12}$ alkyl, $C_{1-12}$ alkenyl, $C_{1-12}$ alkoxy, $C_{1-12}$ alkthio, $C_{1-12}$ alkyamino, cycloalkyl, heterocyclyl, aryl, heteroaryl, aralkyl, alkyl carbonyl, or aralkylcarbonyl. In certain embodiments, at least one of $R_1$-$R_{12}$ is a prenyl group, such as

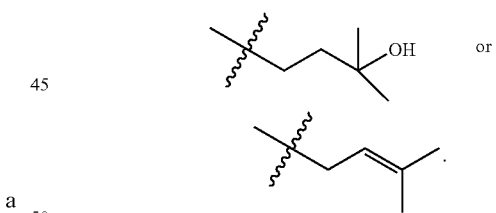

In further embodiments, $R_1$, $R_5$, $R_6$ and $R_{10}$ are H. In still further embodiments, $R_2$ is a glucoside, or $R_2$ and $R_8$ are glycosides, and one or more of $R_4$, $R_9$, and $R_{10}$ are hydroxyl. In yet further embodiments, $R_1$, $R_5$, and $R_6$ are H, and one or more of $R_2$-$R_4$ and $R_7$-$R_{10}$ are independently hydroxyl, $C_{1-3}$ alkoxy, or any combination thereof. In certain specific embodiments, a stilbene includes oxyresveratrol, resveratrol, piceatannol, pinosylvin, 3,4'-dihydroxystilbene, combretastatin A-1, pterostilbene, rhapontigenin, and a stilbene glycoside includes mulberroside A, rhaponticin, piceid, astringin, or any combination of these stilbenes or stilbene glycosides.

It is understood that any embodiment of the compounds of structure (I) to (VI), as set forth above, and any specific substituent set forth herein for the compounds of structure (I) to (VI), may be independently combined with other embodiments or substituents of any one of the compounds of structure (I) to (VI) to form embodiments of this disclosure not specifically set forth above. In addition, in the event that a list of substituents is listed for any particular R group in a particular embodiment or claim, it is understood that each individual substituent may be deleted from the particular embodiment or claim and that the remaining list of substituents will be considered to be within the scope of this disclosure.

For the purposes of administration, compounds and compositions of the present disclosure may be administered as a raw chemical or may be formulated as pharmaceutical or nutraceutical compositions. In certain embodiments, pharmaceutical or nutraceutical compositions of the present disclosure comprise any one or more of the compounds having structure (I) to (VI) and a pharmaceutically or nutraceutically acceptable carrier, diluent or excipient. The compounds of structures (I) to (VI) are individually or in combination present in the composition in an amount that is effective to treat a particular disease or condition of interest. Promoting, managing, or improving joint health or treating disease with compounds as set forth in any one of structures (I) to (VI) can be determined by one skilled in the art, for example, as described in the Examples herein.

In certain embodiments, compounds and compositions (e.g., pharmaceutical, nutraceutical) of the present disclosure may be administered in an amount sufficient to promote joint health; improve joint health; maintain joint health; treat or manage joint health; support joint health; support a normal and comfortable range of motion and/or flexibility; improve range of motion and/or flexibility; reduce the action of harmful enzymes that break down protective joint tissues; alter the action of enzymes that affect joint health; improve joint movement and/or joint function; improve physical mobility; manage and/or maintain physical mobility; alleviate joint pain and/or joint stiffness; improve joint physical function; promote or enhance flexibility and comfortable movement; promote healthy joint function and joint comfort; relieve joint discomfort; relieve joint discomfort caused by exercise, work, overexertion or any combination thereof; promote healthy joints by protecting cartilage integrity; maintain joint cartilage; support joint cartilage; treat, prevent, or manage cartilage degradation; minimize cartilage degradation; promote joint health or comfort by maintaining synovial fluid for joint lubrication; support joint stability and joint flexibility; revitalize joints and promote mobility; promote flexible joints and strong cartilage; maintain steady blood flow to joints to support enhanced flexibility and/or strength; promote joint comfort and a wide range of motion after exercise, work, overexertion, or any combination thereof; or any other associated indication described herein, and generally with acceptable toxicity to a patient.

In certain other embodiments, compounds and compositions (e.g., pharmaceutical, nutraceutical) of the present disclosure may be administered in an amount sufficient to treat osteoarthritis, rheumatoid arthritis, juvenile rheumatoid arthritis, Still's disease, psoriatic arthritis, reactive arthritis, septic arthritis, Reiter's syndrome, Behcet's syndrome, Felty's syndrome, systemic lupus erythematosus, ankylosing spondylitis, diffuse idiopathic skeletal hyperostosis (DISH), sacroiliac joint dysfunction, polymyalgia rheumatic, carpal tunnel syndrome, gout, bursitis, tendenitis, synovitis, SAPHO (synovitis, acne, pustulosis, hyperostosis, osteitis) syndrome, patella chondromalacia, repetitive strain injury, sprain, dislocation, or any other associated indication, and generally with acceptable toxicity to a patient.

Administration of the compounds of this disclosure, or their pharmaceutically or nutraceutically acceptable salts, in pure form or in an appropriate pharmaceutical or nutraceutical composition, can be carried out via any of the accepted modes of administration of agents for serving similar utilities. The pharmaceutical or nutraceutical compositions of this disclosure can be prepared by combining a compound of this disclosure with an appropriate pharmaceutically or nutraceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical or nutraceutical compositions include oral, topical, transdermal, inhalation, parenteral, sublingual, buccal, rectal, vaginal, or intranasal. The term parenteral as used herein includes subcutaneous injections, intravenous, intramuscular, intrasternal injection or infusion techniques. Pharmaceutical or nutraceutical compositions of this disclosure are formulated so as to allow the active ingredients contained therein to be bioavailable upon administration of the composition to a patient. In certain embodiments, compositions of the present disclosure are administered to a subject or patient in the form of one or more dosage units, where, for example, a tablet may be a single dosage unit, and a container of a compound of this disclosure in aerosol form may hold a plurality of dosage units. Actual methods of preparing such dosage forms are known, or will be apparent, to those skilled in this art; for example, see *Remington: The Science and Practice of Pharmacy*, $20^{th}$ Edition (Philadelphia College of Pharmacy and Science, 2000). The composition to be administered will, in any event, contain a therapeutically effective amount of a compound of this disclosure, or a pharmaceutically or nutraceutically acceptable salt thereof, for treatment of a disease or condition of interest in accordance with the teachings of this disclosure.

A pharmaceutical or nutraceutical composition of this disclosure may be in the form of a solid or liquid. In one aspect, the carrier(s) are particulate, so that the compositions are, for example, in tablet or powder form. The carrier(s) may be liquid, with the compositions being, for example, oral syrup, injectable liquid or an aerosol, which is useful in, for example, inhalatory administration.

When intended for oral administration, the pharmaceutical or nutraceutical composition is in either solid or liquid form, where semi-solid, semi-liquid, suspension and gel forms are included within the forms considered herein as either solid or liquid.

As a solid composition for oral administration, the pharmaceutical or nutraceutical composition may be formulated into a powder, granule, compressed tablet, pill, capsule, chewing gum, wafer, bar, or like form. Such a solid composition will typically contain one or more inert diluents or edible carriers. In addition, one or more of the following may be present: binders such as carboxymethylcellulose, ethyl cellulose, cyclodextrin, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex®; glidants such as colloidal silicon dioxide; sweetening agents such as sucrose or saccharin; a flavoring agent such as peppermint, methyl salicylate or orange flavoring; and a coloring agent.

When the pharmaceutical or nutraceutical composition is in the form of a capsule, for example, a gelatin capsule, it may contain, in addition to materials of the above type, a liquid carrier such as polyethylene glycol or oil.

The pharmaceutical or nutraceutical composition may be in the form of a liquid, for example, an elixir, syrup, gel, solution, emulsion or suspension. The liquid may be for oral administration or for delivery by injection, as two examples. When intended for oral administration, a useful composition contains, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical or nutraceutical compositions of this disclosure, whether they be solutions, suspensions or other like form, may include one or more of the following adjuvants: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a generally useful adjuvant. An injectable pharmaceutical or nutraceutical composition is sterile.

A liquid pharmaceutical or nutraceutical composition of this disclosure intended for either parenteral or oral administration should contain an amount of a compound of this disclosure such that a suitable dosage will be obtained.

The pharmaceutical or nutraceutical composition of this disclosure may be intended for topical administration, in which case the carrier may suitably comprise a solution, emulsion, cream, lotion, ointment, or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical or nutraceutical composition for topical administration. If intended for transdermal administration, the composition may include a transdermal patch or iontophoresis device.

The pharmaceutical or nutraceutical composition of this disclosure may be intended for rectal administration, in the form, for example, of a suppository, which will melt in the rectum and release the drug. The composition for rectal administration may contain an oleaginous base as a suitable nonirritating excipient. Such bases include lanolin, cocoa butter and polyethylene glycol.

The pharmaceutical or nutraceutical composition of this disclosure may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical or nutraceutical composition of this disclosure in solid or liquid form may include an agent that binds to the compound of this disclosure and thereby assists in the delivery of the compound. Suitable agents that may act in this capacity include a monoclonal or polyclonal antibody, a protein or a liposome.

The pharmaceutical or nutraceutical composition of this disclosure in solid or liquid form may include reducing the size of a particle to, for example, improve bioavailability. The size of a powder, granule, particle, microsphere, or the like in a composition, with or without an excipient, can be macro (e.g., visible to the eye or at least 100 µm in size), micro (e.g., may range from about 100 µm to about 100 nm in size), nano (e.g., may no more than 100 nm in size), and any size in between or any combination thereof to improve size and bulk density.

The pharmaceutical or nutraceutical composition of this disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of this disclosure may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation, may determine the most appropriate aerosol(s).

The pharmaceutical or nutraceutical compositions of this disclosure may be prepared by methodology well known in the pharmaceutical or nutraceutical art. For example, a pharmaceutical or nutraceutical composition intended to be administered by injection can be prepared by combining a compound of this disclosure with sterile, distilled water so as to form a solution. A surfactant may be added to facilitate the formation of a homogeneous solution or suspension. Surfactants are compounds that non-covalently interact with the compound of this disclosure so as to facilitate dissolution or homogeneous suspension of the compound in the aqueous delivery system.

The compounds of this disclosure, or their pharmaceutically or nutraceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of this disclosure, or pharmaceutically or nutraceutically acceptable derivatives thereof, may also be administered simultaneously with, prior to, or after administration of one or more other therapeutic agents. Such combination therapy includes administration of a single pharmaceutical or nutraceutical dosage formulation which contains a compound of this disclosure and one or more additional active agents, as well as administration of the compound of this disclosure and each active agent in its own separate pharmaceutical or nutraceutical dosage formulation. For example, a compound of this disclosure and another active agent can be administered to the patient together in a single oral dosage composition, such as a tablet or capsule, or each agent can be administered in separate oral dosage formulations. Where separate dosage formulations are used, the compounds of this disclosure and one or more additional active agents can be administered at essentially the same time, i.e., concurrently, or at separate staggered times, i.e., sequentially; combination therapy is understood to include all these regimens.

It is understood that in the present description, combinations of substituents or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diaryllalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3$^{rd}$ Ed., Wiley. As one of skill in the art would appreciate, a protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of this disclosure which are pharmacologically active. Such derivatives may therefore be described as "prodrugs". All prodrugs of compounds of this disclosure are included within the scope of this disclosure.

Furthermore, all compounds of this disclosure which exist in free base or acid form can be converted to their pharmaceutically or nutraceutically acceptable salts by treatment with the appropriate inorganic or organic base or acid by methods known to one skilled in the art. Salts of the compounds of this disclosure can be converted to their free base or acid form by standard techniques.

In some embodiments, compounds of the present disclosure can be isolated from plant sources, for example, from those plants included in the Examples and elsewhere throughout the present application. Suitable plant parts for isolation of the compounds include leaves, bark, trunk, trunk bark, stems, stem bark, twigs, tubers, root, root bark, bark surface (such as periderm or polyderm, which may include phellem, phellogen, phelloderm, or any combination thereof), young shoots, rhizomes, seed, fruit, androecium, gynoecium, calyx, stamen, petal, sepal, carpel (pistil), flower, or any combination thereof. In some related embodiments, the compounds are isolated from plant sources and synthetically modified to contain any of the recited substituents. In this regard, synthetic modification of the compound isolated from plants can be accomplished using any number of techniques that are known in the art and are well within the knowledge of one of ordinary skill in the art.

As noted herein, compounds of a Diels-Alder adduct of a chalcone and a prenylphenyl moiety, prenylated flavonoids, stilbenes, or any combination thereof may be obtained by chemical synthesis or from a plant extract, such as a *Morus* or *Milicia* extract. For example, *Morus* is a genus of flowering trees in the family Moraceae, which comprises more than 30 species (known as mulberries) that grow wild or under cultivation in many countries. Exemplary *Morus* species include *Morus alba* L., *Morus australis* Poir, *Morus celtidifolia* Kunth, *Morus insignis*, *Morus mesozygia* Stapf, *Morus microphylla*, *Morus nigra* L., *Morus rubra* L., *Morus atropurpurea*, *Morus bombycis*, *Morus cathayana*, *Morus indica*, *Morus thou*, *Morus japonica*, *Morus kagayamae*, *Morus laevigata*, *Morus latifolia*, *Morus liboensis*, *Morus macroura*, *Morus mongolica*, *Morus multicaulis*, *Morus notabilis*, *Morus rotundiloba*, *Morus serrate*, *Morus heterophyllus*, *Morus tillaefolia*, *Morus trilobata*, *Morus yunnanensis*, and *Morus wittiorum*.

In certain embodiments, a *Morus* extract is from *Morus alba*, or a *Morus* extract is a mixture of extracts from one, two, three, four, or five different *Morus* species. A mixture of extracts may include extracts from two or more *Morus* species or other sources listed in Table A. For example, a composition comprising a Diels-Alder adduct of a chalcone and a prenylphenyl moiety, a prenylated flavonoid, a stilbene, or any combination thereof may be made up of a *Morus* extract (e.g., *Morus alba*) and a *Milicia* extract (e.g., *Milicia excelsa*). In certain embodiments, a *Morus* extract enriched for prenylated flavonoids and stilbenes is from *Morus alba* (a) root bark, (b) root bark and leaves, (c) rootbark and twigs, (d) root bark, leaves and twigs, or (e) root bark, root wood, fine roots, stem bark, branch, branch bark, branch wood, and twigs.

In some specific embodiments, compounds of a Diels-Alder adduct of a chalcone and a prenylphenyl moiety may be any one or more of the compounds provided in Table A.

TABLE A

List of Exemplary Diels-Alder Adduct Compounds

| Structure | Name | Species | Molecular Formula | M.W. |
|---|---|---|---|---|
| (structure shown) | Albafuran C | *Morus alba* | $C_{34}H_{28}O_9$ | 580.590 |

TABLE A-continued
List of Exemplary Diels-Alder Adduct Compounds
| Structure | Name | Species | Molecular Formula | M.W. |
|---|---|---|---|---|
| 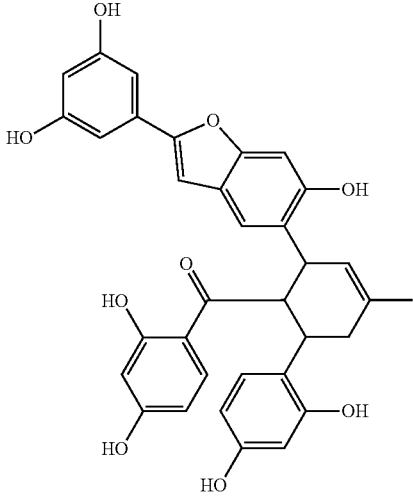 [SMILES: CC1=CC(c2cc3cc(-c4cc(O)cc(O)c4)oc3cc2O)C(C(=O)c2ccc(O)cc2O)C(c2ccc(O)cc2O)C1] | Albafuran C; 2-Epimer | *Morus australis* | $C_{34}H_{28}O_9$ | 580.590 |
| 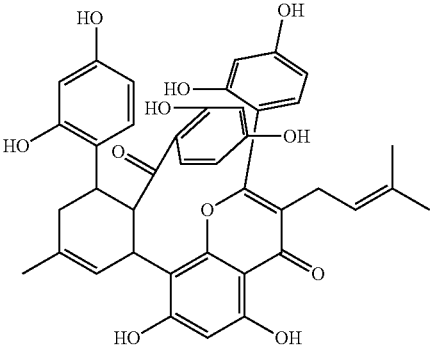 [SMILES: CC(C)=CCc1c(-c2ccc(O)cc2O)oc2c(C3C=C(C)CC(c4ccc(O)cc4O)C3C(=O)c3ccc(O)cc3O)c(O)cc(O)c2c1=O] | Albanin F | *Morus alba*, also from *Morus australis*, *Morus bombycis*, and *Morus lhou* | $C_{40}H_{36}O_{11}$ | 692.718 |
| 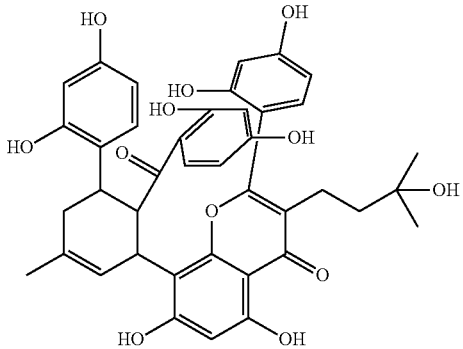 [SMILES: CC1=CC(c2c(O)cc(O)c3c(=O)c(CCC(C)(C)O)c(-c4ccc(O)cc4O)oc23)C(C(=O)c2ccc(O)cc2O)C(c2ccc(O)cc2O)C1] | Albanin F (Moracenin D); 12,13-Dihydro, 13-hydroxy | *Morus* sp. | $C_{40}H_{38}O_{12}$ | 710.733 |

TABLE A-continued

List of Exemplary Diels-Alder Adduct Compounds

| Structure | Name | Species | Molecular Formula | M.W. |
|---|---|---|---|---|
| 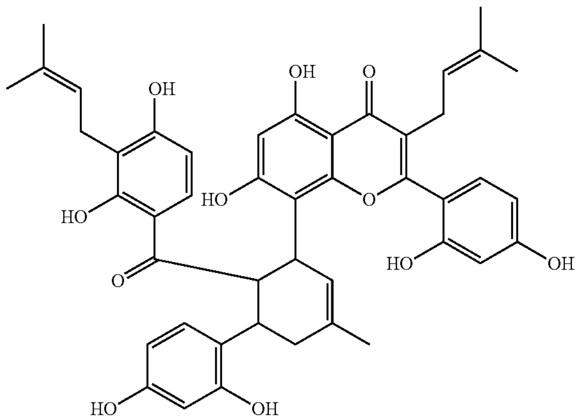 [SMILES: CC(C)=CCc1c(O)ccc(C(=O)C2C(c3c(O)cc(O)c4c(=O)c(CC=C(C)C)c(-c5ccc(O)cc5O)oc34)C=C(C)CC2c2ccc(O)cc2O)c1O] | Albanin G (Kuwanon H. Moracenin A.) | Morus alba; also isol. from Morus australis, Morus bombycis, and Morus lhou | $C_{45}H_{44}O_{11}$ | 760.836 |
| 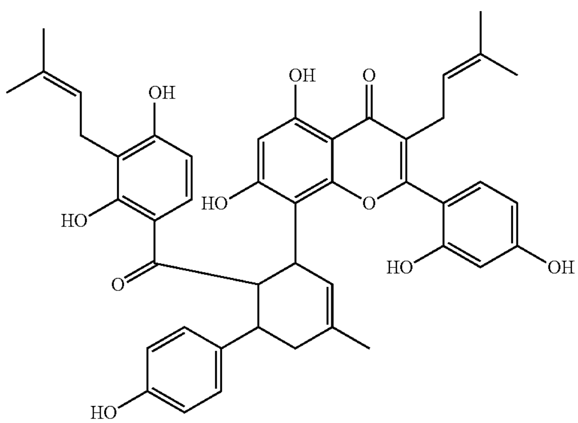 [SMILES: CC(C)=CCc1c(O)ccc(C(=O)C2C(c3c(O)cc(O)c4c(=O)c(CC=C(C)C)c(-c5ccc(O)cc5O)oc34)C=C(C)CC2c2ccc(O)cc2)c1O] | Albanin G; 2'''-Deoxy (Mongolicin D) | Morus mongolica | $C_{45}H_{44}O_{10}$ | 744.837 |
| 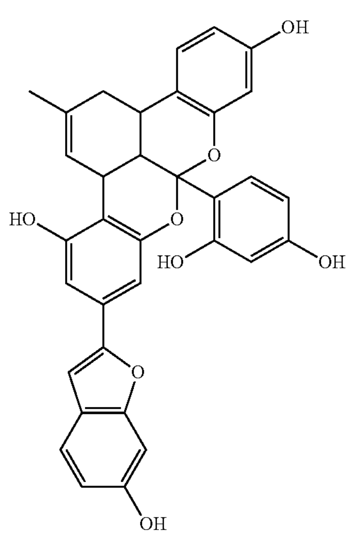 [SMILES: CC1=CC2c3c(O)cc(-c4cc5ccc(O)cc5o4)cc3OC3(c4ccc(O)cc4O)Oc4cc(O)ccc4C(C1)C23] | Albanol A (Mulberrofuran G.) | Morus lhou | $C_{34}H_{26}O_8$ | 562.575 |

TABLE A-continued
List of Exemplary Diels-Alder Adduct Compounds
| Structure | Name | Species | Molecular Formula | M.W. |
|---|---|---|---|---|
| 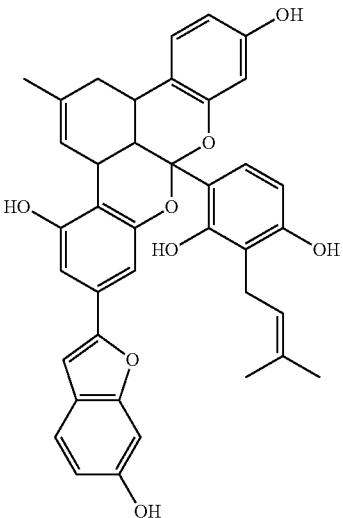 [SMILES: CC(C)=CCc1c(O)ccc(C23Oc4cc(O)ccc4C4CC(C)=CC(c5c(O)cc(-c6cc7ccc(O)cc7o6)cc5O2)C43)c1O] | Albanol A; 3''-(3-Methyl-2-butenyl), Mulberrofuran F | *Morus lhou* | $C_{39}H_{34}O_8$ | 630.693 |
| 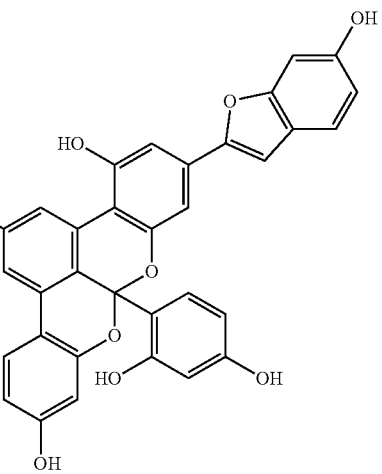 | Albanol B | *Morus alba* | $C_{34}H_{22}O_8$ | 558.543 |
| 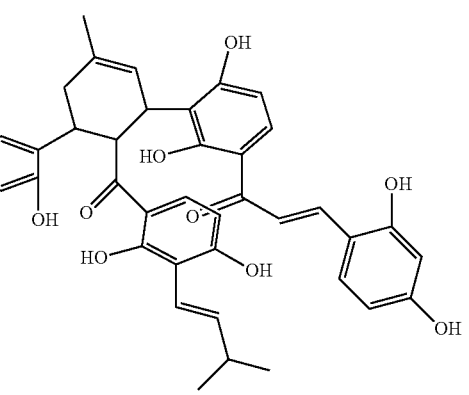 | Artonin C | *Artocarpus heterophyllus* (jackfruit) | $C_{40}H_{38}O_{10}$ | 678.734 |

TABLE A-continued
List of Exemplary Diels-Alder Adduct Compounds
| Structure | Name | Species | Molecular Formula | M.W. |
|---|---|---|---|---|
| 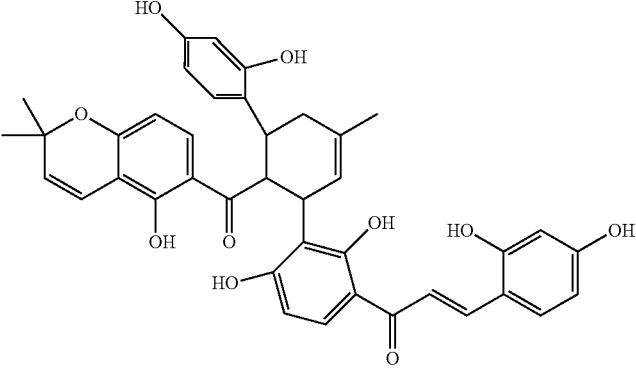 [SMILES: CC1=CC(c2c(O)ccc(C(=O)/C=C/c3ccc(O)cc3O)c2O)C(C(=O)c2ccc3c(c2O)C=CC(C)(C)O3)C(c2ccc(O)cc2O)C1] | Artonin D | *Artocarpus heterophyllus* (jackfruit) | $C_{40}H_{36}O_{10}$ | 676.718 |
| 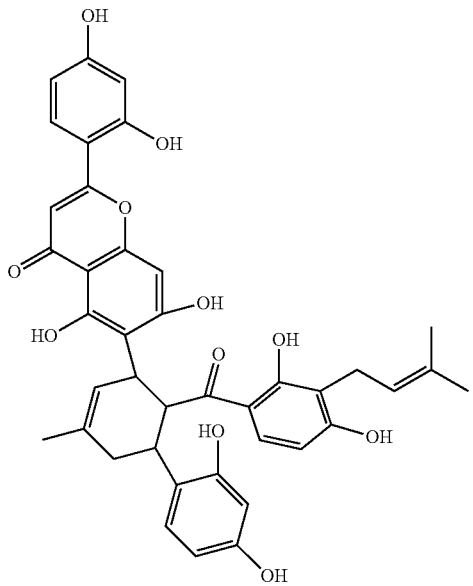 [SMILES: CC(C)=CCc1c(O)ccc(C(=O)C2C(c3c(O)cc4oc(-c5ccc(O)cc5O)cc(=O)c4c3O)C=C(C)CC2c2ccc(O)cc2O)c1O] | Artonin I | *Morus heterophyllus* | $C_{40}H_{36}O_{11}$ | 692.718 |
| 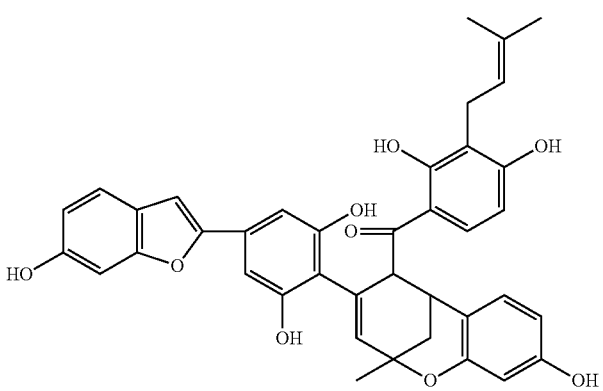 [SMILES: CC(C)=CCc1c(O)ccc(C(=O)C2C(c3c(O)cc(-c4cc5ccc(O)cc5o4)cc3O)=CC3(C)CC2c2ccc(O)cc2O3)c1O] | Australisin B | *Morus australis* | $C_{39}H_{34}O_9$ | 646.692 |

TABLE A-continued

List of Exemplary Diels-Alder Adduct Compounds

| Structure | Name | Species | Molecular Formula | M.W. |
|---|---|---|---|---|
| 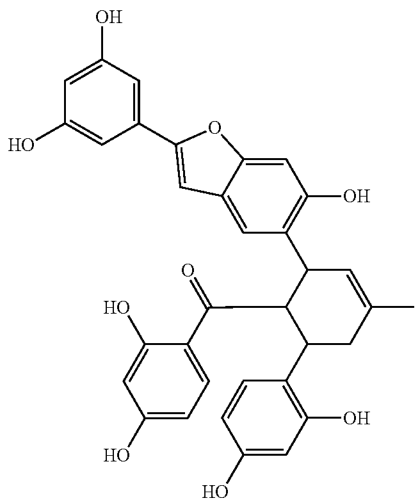 [SMILES: CC1=CC(c2cc3cc(-c4cc(O)cc(O)c4)oc3cc2O)C(C(=O)c2ccc(O)cc2O)C(c2ccc(O)cc2O)C1] | Australisin C.; 2-Epimer | *Morus australis* | $C_{34}H_{28}O_9$ | |
| 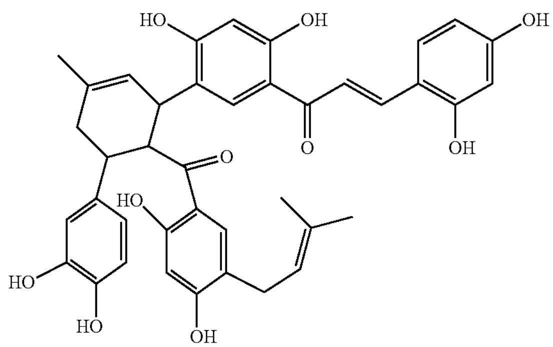 [SMILES: CC(C)=CCc1cc(C(=O)C2C(c3cc(C(=O)/C=C/c4ccc(O)cc4O)c(O)cc3O)C=C(C)CC2c2ccc(O)c(O)c2)c(O)cc1O] | Brosimone B | *Brosimopsis oblongifolia* (preferred genus name *Brosimum*) | $C_{40}H_{38}O_{10}$ | 678.734 |
| 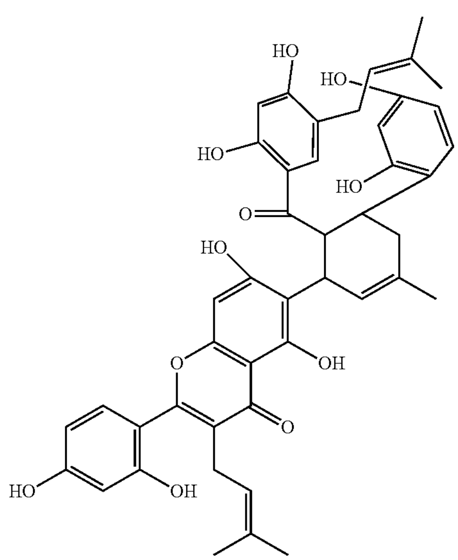 [SMILES: CC(C)=CCc1cc(C(=O)C2C(c3c(O)cc4oc(-c5ccc(O)cc5O)c(CC=C(C)C)c(=O)c4c3O)C=C(C)CC2c2ccc(O)cc2O)c(O)cc1O] | Brosimone D | *Brosimopsis oblongifolia* (preferred genus name *Brosimum*) | $C_{45}H_{44}O_{11}$ | 760.836 |

TABLE A-continued
List of Exemplary Diels-Alder Adduct Compounds
| Structure | Name | Species | Molecular Formula | M.W. |
|---|---|---|---|---|
| 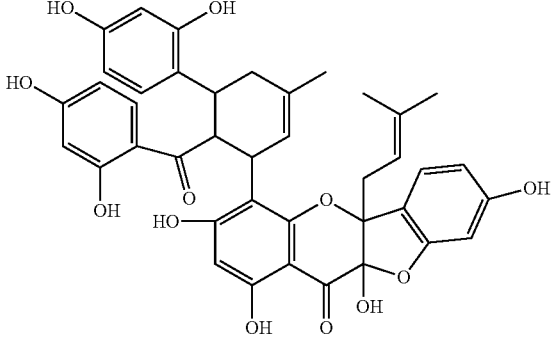 [SMILES: CC(C)=CCC12Oc3c(c(O)cc(O)c3C3C=C(C)CC(c4ccc(O)cc4O)C3C(=O)c3ccc(O)cc3O)C(=O)C1(O)Oc1cc(O)ccc12] | Cathayanon A | *Morus cathayana* | $C_{40}H_{36}O_{12}$ | 708.717 |
| 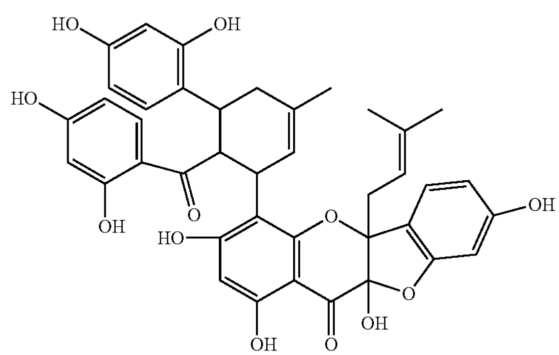 | Cathayanon A; 14-Epimer | *Morus cathayana* | $C_{40}H_{36}O_{12}$ | 708.717 |
| 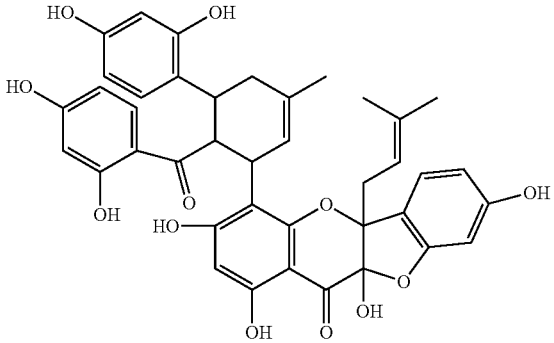 [SMILES: CC(C)=CCC12Oc3c(c(O)cc(O)c3C3C=C(C)CC(c4ccc(O)cc4O)C3C(=O)c3ccc(O)cc3O)C(=O)C1(O)Oc1cc(O)ccc12] | Cathayanon E | *Morus cathayana* | $C_{40}H_{36}O_{12}$ | 708.717 |
| 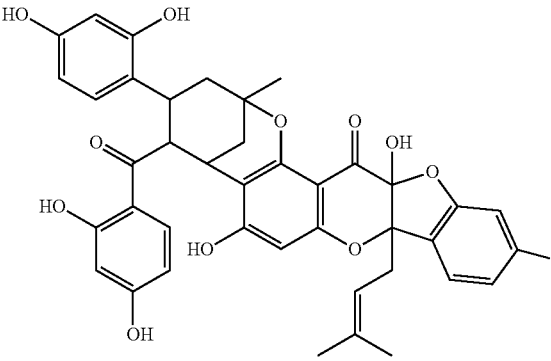 | | | | |

TABLE A-continued

List of Exemplary Diels-Alder Adduct Compounds

| Structure | Name | Species | Molecular Formula | M.W. |
|---|---|---|---|---|
| 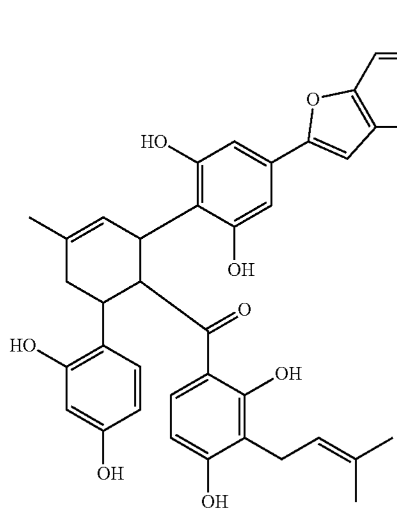 | Chalcomoracin | Morus alba and Morus mongolica | $C_{39}H_{36}O_9$ | 648.708 |
| 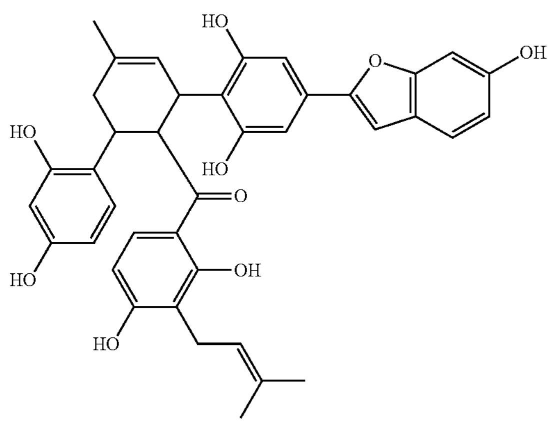 [SMILES: CC(C)=CCc1c(O)ccc(C(=O)C2C(c3c(O)cc(-c4cc5ccc(O)cc5o4)cc3O)C=C(C)CC2c2ccc(O)cc2O)c1O] | Chalcomoracin; 3",5"-Diepimer | Sorocea muriculata | $C_{39}H_{36}O_9$ | 648.708 |
| 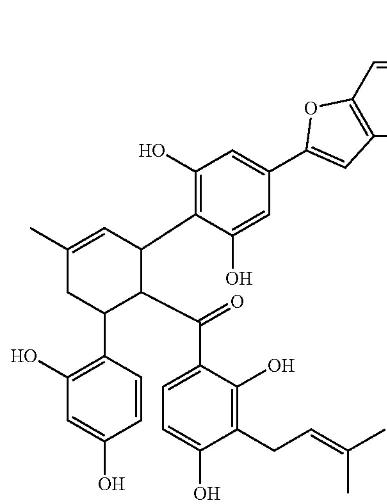 | Chalcomoracin; 3"-Epimer | Morus mongolica | $C_{39}H_{36}O_9$ | 648.708 |

TABLE A-continued
List of Exemplary Diels-Alder Adduct Compounds
| Structure | Name | Species | Molecular Formula | M.W. |
|---|---|---|---|---|
| 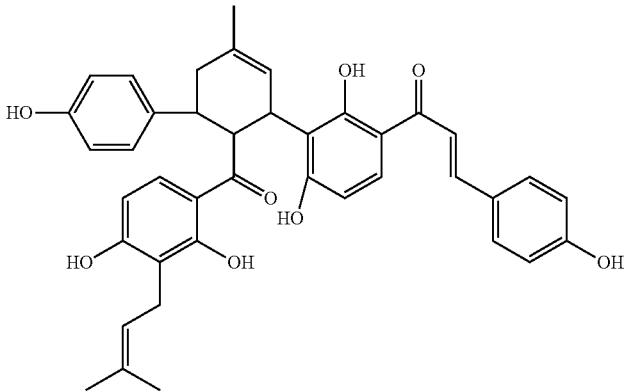 [SMILES: CC(C)=CCc1c(O)ccc(C(=O)C2C(c3c(O)ccc(C(=O)/C=C/c4ccc(O)cc4)c3O)C=C(C)CC2c2ccc(O)cc2)c1O] | Dorstenone | *Dorstenia barteri* | $C_{40}H_{38}O_8$ | 646.735 |
| 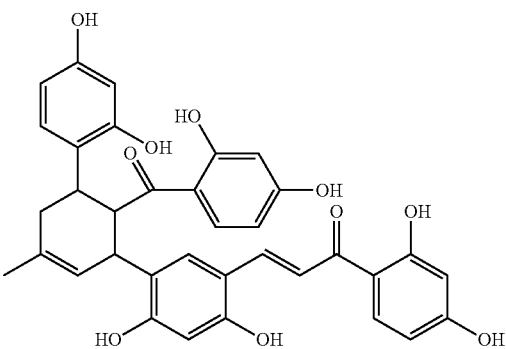 [SMILES: CC1=CC(c2cc(/C=C/C(=O)c3ccc(O)cc3O)c(O)cc2O)C(C(=O)c2ccc(O)cc2O)C(c2ccc(O)cc2O)C1] | Guangsangon C | *Morus macroura* | $C_{35}H_{30}O_{10}$ | 610.616 |
| 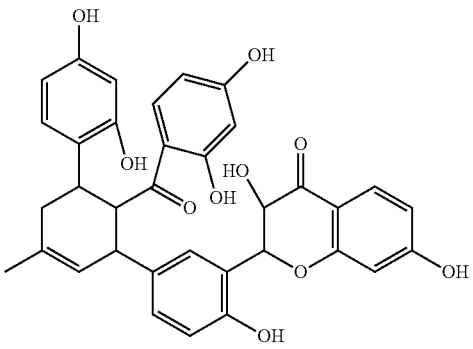 [SMILES: CC1=CC(c2ccc(O)c(C3Oc4cc(O)ccc4C(=O)C3O)c2)C(C(=O)c2ccc(O)cc2O)C(c2ccc(O)cc2O)C1] | Guangsangon D | *Morus macroura* | $C_{35}H_{30}O_{10}$ | 610.616 |
| 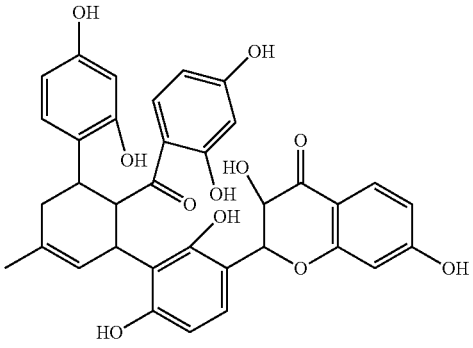 [SMILES: CC1=CC(c2c(O)ccc(C3Oc4cc(O)ccc4C(=O)C3O)c2O)C(C(=O)c2ccc(O)cc2O)C(c2ccc(O)cc2O)C1] | Guangsangon D; 2'-Deoxy, 4',6'-dihydroxy | *Morus macroura* | $C_{35}H_{30}O_{11}$ | 626.615 |

TABLE A-continued

List of Exemplary Diels-Alder Adduct Compounds

| Structure | Name | Species | Molecular Formula | M.W. |
|---|---|---|---|---|
| 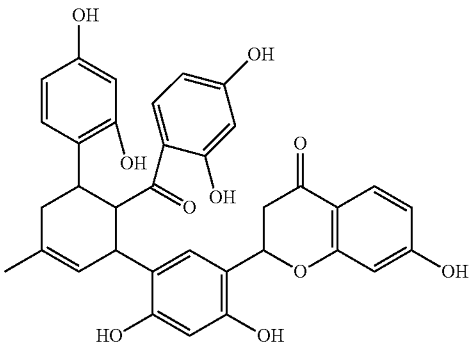 [SMILES: CC1=CC(c2cc(C3CC(=O)c4ccc(O)cc4O3)c(O)cc2O)C(C(=O)c2ccc(O)cc2O)C(c2ccc(O)cc2O)C1] | Guangsangon D; 3-Deoxy, 4'-hydroxy | *Morus macroura* and *Morus wittiorum* | $C_{35}H_{30}O_{10}$ | 610.616 |
| 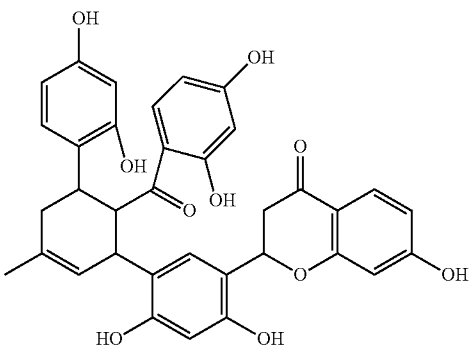 [SMILES: CC1=CC(c2cc(C3CC(=O)c4ccc(O)cc4O3)c(O)cc2O)C(C(=O)c2ccc(O)cc2O)C(c2ccc(O)cc2O)C1] | Guangsangon D; 2-Epimer, 3-deoxy, 4'-hydroxy | *Morus macroura* | $C_{35}H_{30}O_{10}$ | 610.616 |
| 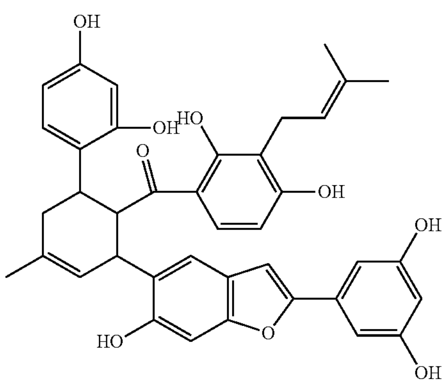 [SMILES: CC(C)=CCc1c(O)ccc(C(=O)C2C(c3cc4cc(-c5cc(O)cc(O)c5)oc4cc3O)C=C(C)CC2c2ccc(O)cc2O)c1O] | Guangsangon E | *Morus macroura* | $C_{39}H_{36}O_{9}$ | 648.708 |
| 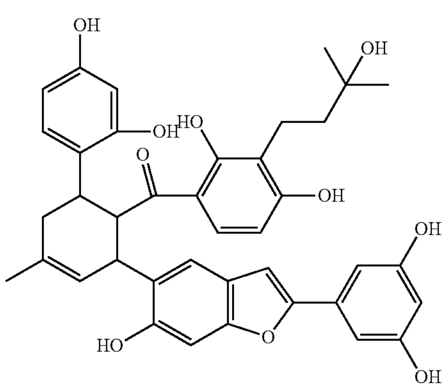 [SMILES: CC1=CC(c2cc3cc(-c4cc(O)cc(O)c4)oc3cc2O)C(C(=O)c2ccc(O)c(CCC(C)(C)O)c2O)C(c2ccc(O)cc2O)C1] | Guangsangon E; 3''-Epimer, 2'''',3''''-dihydro, 3''''-hydroxy | *Morus macroura* | $C_{39}H_{38}O_{10}$ | 666.723 |

TABLE A-continued

List of Exemplary Diels-Alder Adduct Compounds

| Structure | Name | Species | Molecular Formula | M.W. |
|---|---|---|---|---|
| 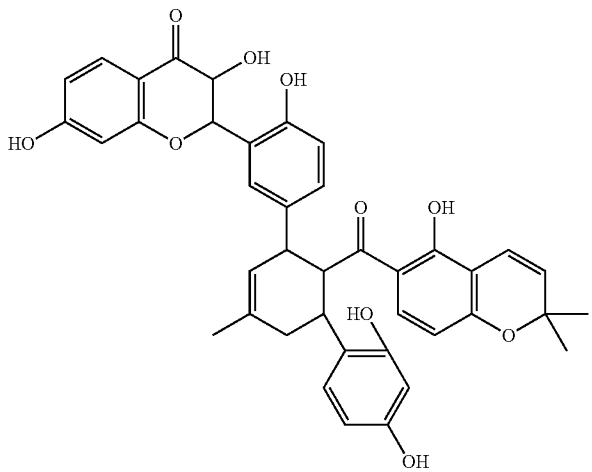 [SMILES: CC1=CC(c2ccc(O)c(C3Oc4cc(O)ccc4C(=O)C3O)c2)C(C(=O)c2ccc3c(c2O)C=CC(C)(C)O3)C(c2ccc(O)cc2O)C1] | Guangsangon F | Morus macroura | $C_{40}H_{36}O_{10}$ | 676.718 |
| 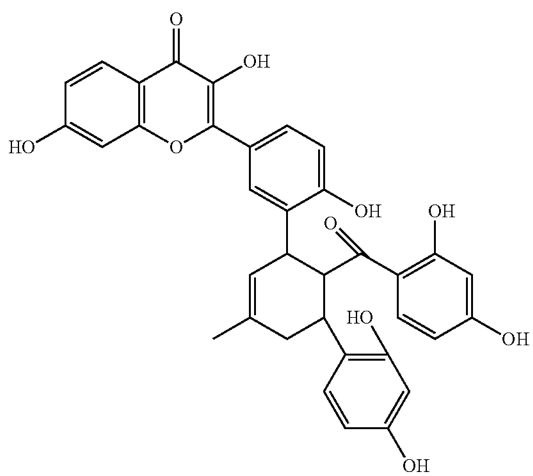 [SMILES: CC1=CC(c2cc(-c3oc4cc(O)ccc4c(=O)c3O)ccc2O)C(C(=O)c2ccc(O)cc2O)C(c2ccc(O)cc2O)C1] | Guangsangon G | Morus macroura | $C_{35}H_{28}O_{10}$ | 608.600 |
| | Guangsangon G; 1″-Epimer, 2′-hydroxy | Morus macroura | $C_{35}H_{28}O_{11}$ | 624.600 |

TABLE A-continued

List of Exemplary Diels-Alder Adduct Compounds

| Structure | Name | Species | Molecular Formula | M.W. |
|---|---|---|---|---|
| 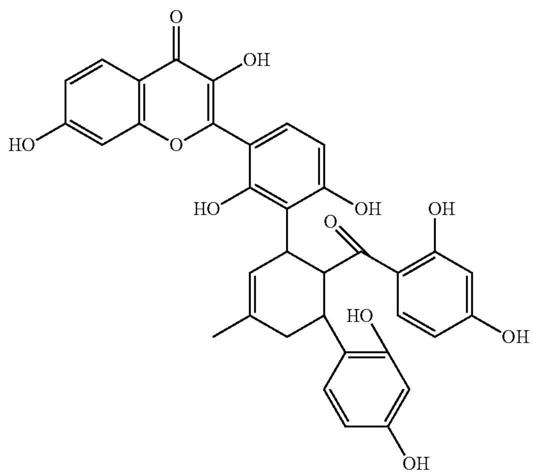 [SMILES: CC1=CC(c2c(O)ccc(-c3oc4cc(O)ccc4c(=O)c3O)c2O)C(C(=O)c2ccc(O)cc2O)C(c2ccc(O)cc2O)C1] | Guangsangon G; 2'-Hydroxy | Morus macroura | $C_{35}H_{28}O_{11}$ | 624.600 |
| 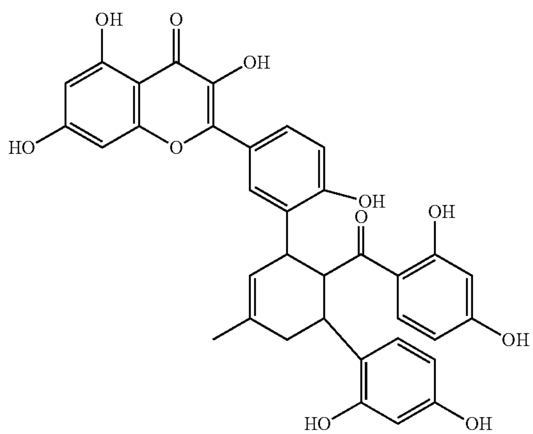 [SMILES: CC1=CC(c2cc(-c3oc4cc(O)cc(O)c4c(=O)c3O)ccc2O)C(C(=O)c2ccc(O)cc2O)C(c2ccc(O)cc2O)C1] | Guangsangon G; 5-Hydroxy | Morus wittiorum | $C_{35}H_{28}O_{11}$ | 625.600 |
| 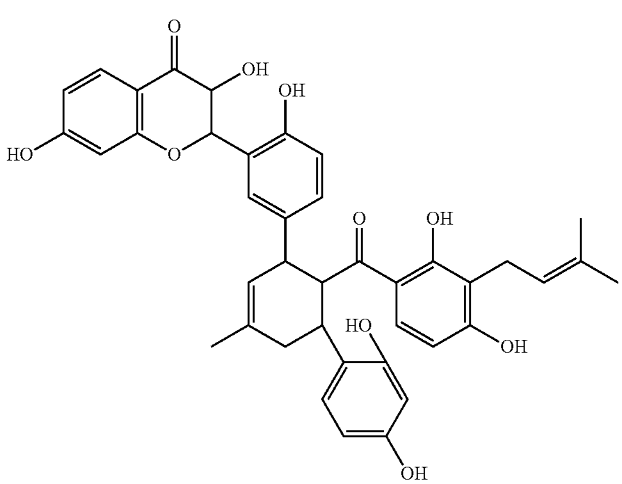 [SMILES: CC(C)=CCc1c(O)ccc(C(=O)C2C(c3ccc(O)c(C4Oc5cc(O)ccc5C(=O)C4O)c3)C=C(C)CC2c2ccc(O)cc2O)c1O] | Guangsangon H | Morus macroura | $C_{40}H_{38}O_{10}$ | 678.734 |

TABLE A-continued

List of Exemplary Diels-Alder Adduct Compounds

| Structure | Name | Species | Molecular Formula | M.W. |
|---|---|---|---|---|
| 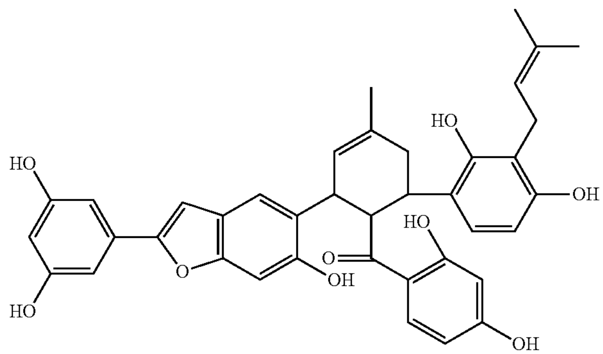 [SMILES: CC(C)=CCc1c(O)ccc(C2CC(C)=CC(c3cc4cc(-c5cc(O)cc(O)c5)oc4cc3O)C2C(=O)c2ccc(O)cc2O)c1O] | Guangsangon J | *Morus wittiorum* | $C_{39}H_{36}O_9$ | 648.708 |
| 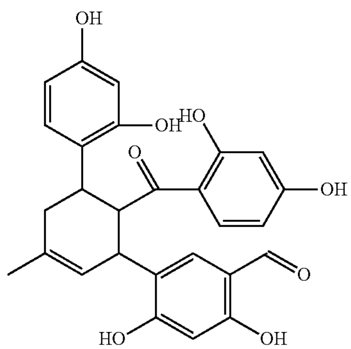 [SMILES: CC1=CC(c2cc(C=O)c(O)cc2O)C(C(=O)c2ccc(O)cc2O)C(c2ccc(O)cc2O)C1] | Guangsangon L | *Morus alba* | $C_{27}H_{24}O_8$ | 476.482 |
| 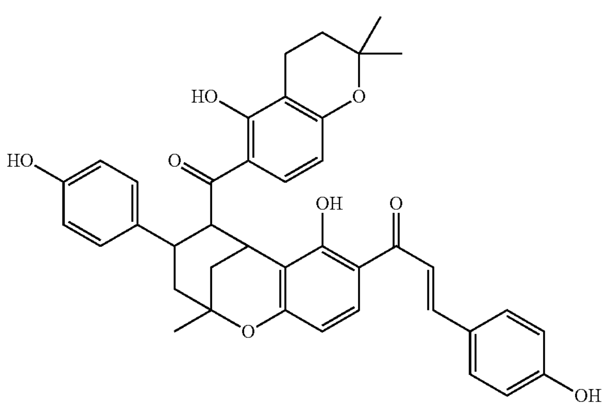 [SMILES: CC1(C)CCc2c(ccc(C(=O)C3C(c4ccc(O)cc4)CC4(C)CC3c3c(ccc(C(=O)/C=C/c5ccc(O)cc5)c3O)O4)c2O)O1] | Isobavachromene dimer | *Dorstenia zenkeri* | $C_{40}H_{38}O_8$ | 646.735 |
| 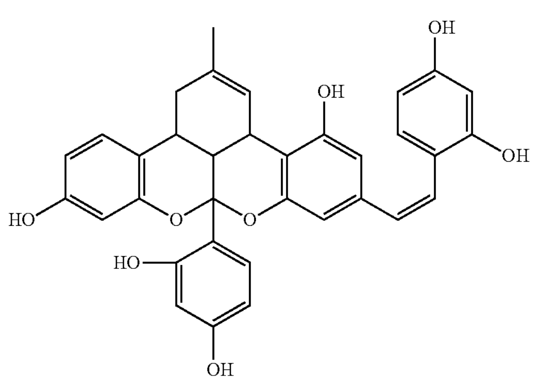 [SMILES: CC1=CC2c3c(O)cc(/C=C\c4ccc(O)cc4O)cc3OC3(c4ccc(O)cc4O)Oc4cc(O)ccc4C(C1)C23] | Kuwanol A | *Morus bombycis* | $C_{34}H_{28}O_8$ | 564.590 |

TABLE A-continued
List of Exemplary Diels-Alder Adduct Compounds
| Structure | Name | Species | Molecular Formula | M.W. |
|---|---|---|---|---|
| 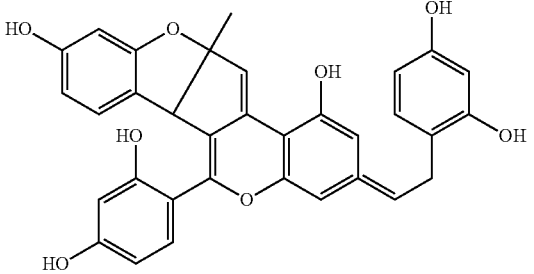 | Kuwanol B | *Morus bombycis* | $C_{34}H_{26}O_8$ | 562.575 |
| 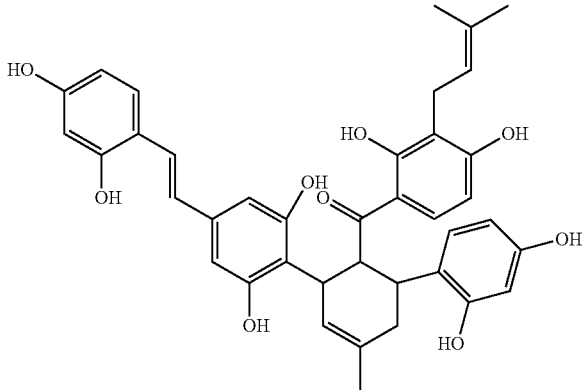 [SMILES: CC(C)=CCc1c(O)ccc(C(=O)C2C(c3c(O)cc(/C=C/c4ccc(O)cc4O)cc3O)C=C(C)CC2c2ccc(O)cc2O)c1O] | Kuwanol E | *Morus alba* (white mulberry) | $C_{39}H_{38}O_9$ | 650.724 |
| 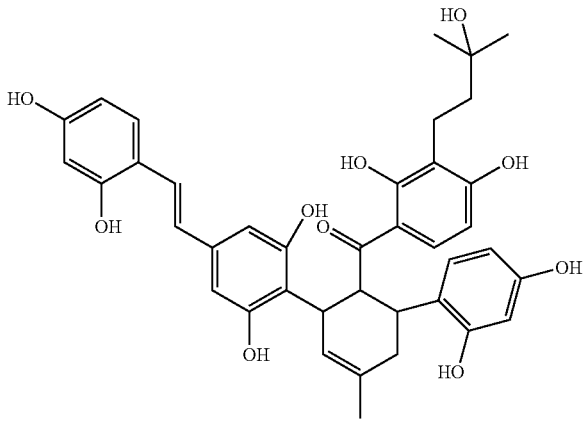 [SMILES: CC1=CC(c2c(O)cc(/C=C/c3ccc(O)cc3O)cc2O)C(C(=O)c2ccc(O)c(CCC(C)(C)O)c2O)C(c2ccc(O)cc2O)C1] | Kuwanol E; 2''',3'''-Dihydro, 3'''-hydroxy | *Sorocea ilicifolia* | $C_{39}H_{40}O_{10}$ | 668.739 |

TABLE A-continued
List of Exemplary Diels-Alder Adduct Compounds
| Structure | Name | Species | Molecular Formula | M.W. |
|---|---|---|---|---|
| 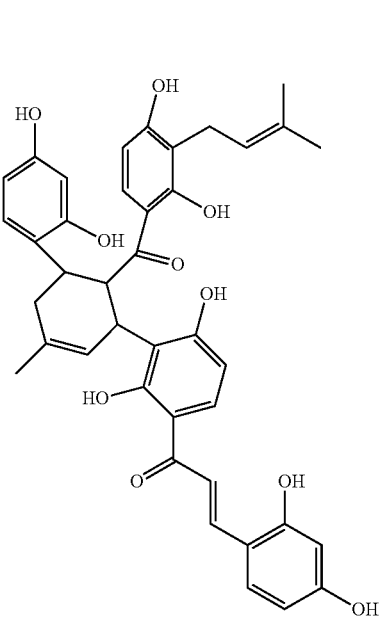 [SMILES: CC(C)=CCc1c(O)ccc(C(=O)C2C(c3c(O)ccc(C(=O)/C=C/c4ccc(O)cc4O)c3O)C=C(C)CC2c2ccc(O)cc2O)c1O] | Kuwanon J | Morus alba and from Morus bombycis and Morus nigra | $C_{40}H_{38}O_{10}$ | 678.734 |
| 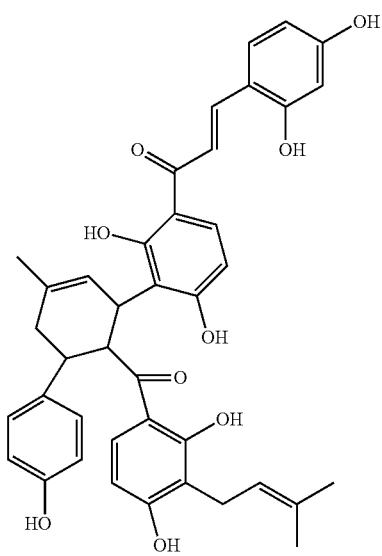 [SMILES: CC(C)=CCc1c(O)ccc(C(=O)C2C(c3c(O)ccc(C(=O)/C=C/c4ccc(O)cc4O)c3O)C=C(C)CC2c2ccc(O)cc2)c1O] | Kuwanon J; 16''-Deoxy | Morus alba (white mulberry) | $C_{40}H_{38}O_9$ | 662.735 |

TABLE A-continued

List of Exemplary Diels-Alder Adduct Compounds

| Structure | Name | Species | Molecular Formula | M.W. |
|---|---|---|---|---|
| 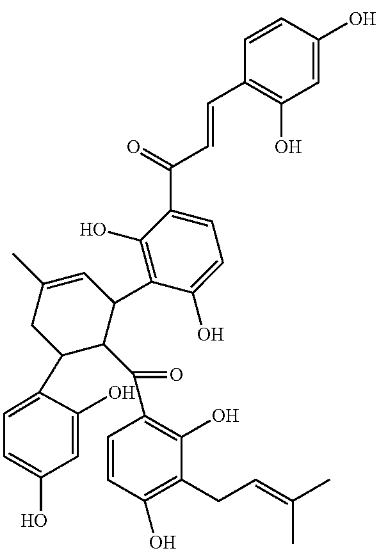 [SMILES: CC(C)=CCc1c(O)ccc(C(=O)C2C(c3c(O)ccc(C(=O)/C=C/c4ccc(O)cc4O)c3O)C=C(C)CC2c2ccc(O)cc2O)c1O] | Kuwanon J; 2-Deoxy | *Morus alba* (white mulberry) | $C_{40}H_{38}O_9$ | 662.735 |
|  | Kuwanon J, Δ21″,22″-Isomer, 2-deoxy | *Morus alba* (white mulberry) | $C_{40}H_{38}O_9$ | 662.735 |

TABLE A-continued

List of Exemplary Diels-Alder Adduct Compounds

| Structure | Name | Species | Molecular Formula | M.W. |
|---|---|---|---|---|
| | Kuwanon J; 2,16''-Dideoxy | *Morus alba* (white mulberry) | $C_{40}H_{38}O_8$ | 646.735 |
| 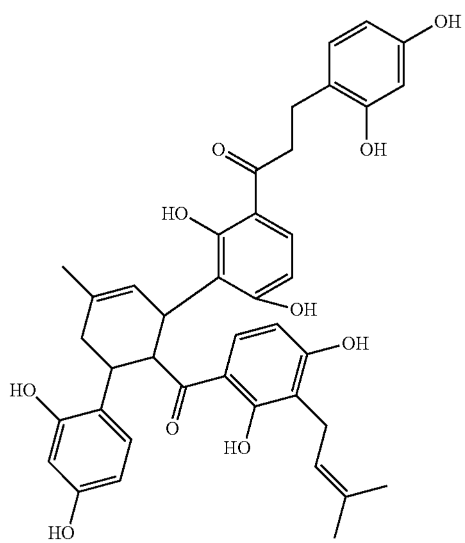 [SMILES: CC(C)=CCc1c(O)ccc(C(=O)C2C(c3c(O)ccc(C(=O)CCc4ccc(O)cc4O)c3O)C=C(C)CC2c2ccc(O)cc2O)c1O] | Kuwanon J; 2',3'-Dihydro | *Morus mongolica* | $C_{40}H_{40}O_{10}$ | 680.750 |

TABLE A-continued

List of Exemplary Diels-Alder Adduct Compounds

| Structure | Name | Species | Molecular Formula | M.W. |
|---|---|---|---|---|
| | Kuwanon J; 1″-Epimer | *Morus alba* and *Morus bombycus* | $C_{40}H_{38}O_{10}$ | 678.734 |
| | Kuwanon J; Δ21″,22″-Isomer, 2-deoxy (Artonin X.) | *Artocarpus heterophyllus* (jackfruit) | $C_{40}H_{38}O_9$ | 662.735 |

TABLE A-continued
List of Exemplary Diels-Alder Adduct Compounds
| Structure | Name | Species | Molecular Formula | M.W. |
|---|---|---|---|---|
| 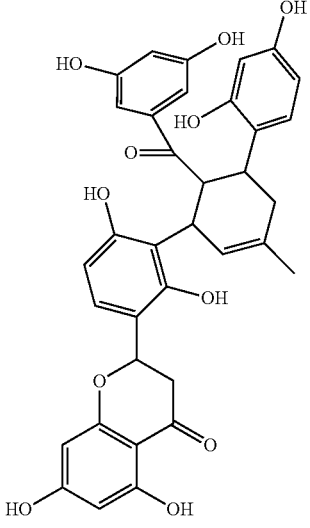 [SMILES: CC1=CC(c2c(O)ccc(C3CC(=O)c4c(O)cc(O)cc4O3)c2O)C(C(=O)c2cc(O)cc(O)c2)C(c2ccc(O)cc2O)C1] | Kuwanon L | *Morus alba* (white mulberry) | $C_{35}H_{30}O_{11}$ | 626.615 |
| 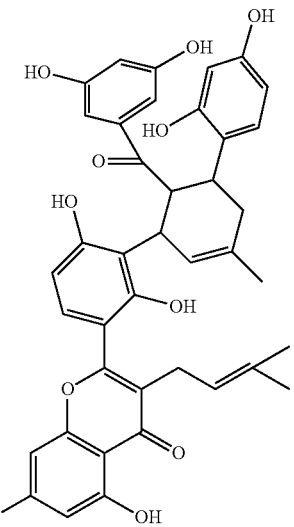 | Kuwanon L; 2,3-Didehydro, 3-(3-methyl-2-butenyl) | *Morus alba* (white mulberry) | $C_{40}H_{36}O_{11}$ | 692.718 |

TABLE A-continued

List of Exemplary Diels-Alder Adduct Compounds

| Structure | Name | Species | Molecular Formula | M.W. |
|---|---|---|---|---|
| 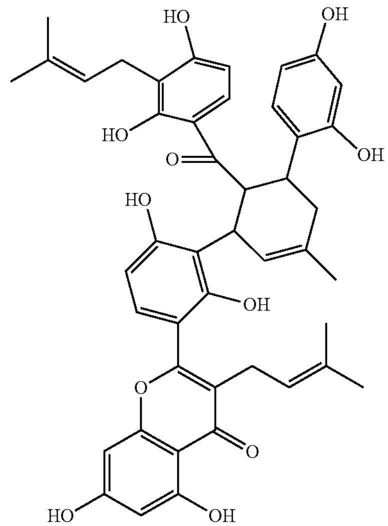 [SMILES: CC(C)=CCc1c(O)ccc(C(=O)C2C(c3c(O)ccc(-c4oc5cc(O)cc(O)c5c(=O)c4CC=C(C)C)c3O)C=C(C)CC2c2ccc(O)cc2O)c1O] | Kuwanon N | *Morus lhou* | $C_{45}H_{44}O_{11}$ | 760.836 |
| 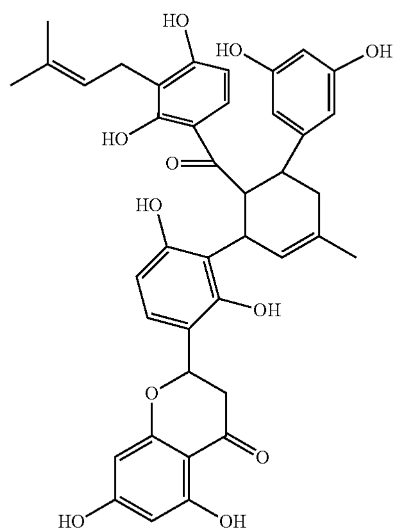 [SMILES: CC(C)=CCc1c(O)ccc(C(=O)C2C(c3c(O)ccc(C4CC(=O)c5c(O)cc(O)cc5O4)c3O)C=C(C)CC2c2cc(O)cc(O)c2)c1O] | Kuwanon O | *Morus lhou* | $C_{40}H_{38}O_{11}$ | 694.734 |
| 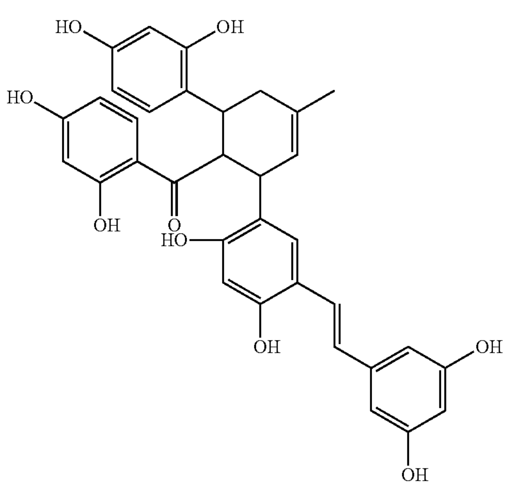 [SMILES: CC1=CC(c2cc(/C=C/c3cc(O)cc(O)c3)c(O)cc2O)C(C(=O)c2ccc(O)cc2O)C(c2ccc(O)cc2O)C1] | Kuwanon P | *Morus lhou* | $C_{34}H_{30}O_{9}$ | 582.606 |

TABLE A-continued

List of Exemplary Diels-Alder Adduct Compounds

| Structure | Name | Species | Molecular Formula | M.W. |
|---|---|---|---|---|
| 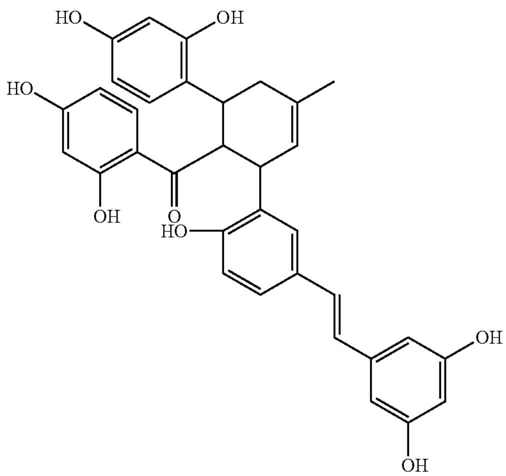 [SMILES: CC1=CC(c2cc(/C=C/c3cc(O)cc(O)c3)ccc2O)C(C(=O)c2ccc(O)cc2O)C(c2ccc(O)cc2O)C1] | Kuwanon P; 2-Deoxy | *Morus macroura* | $C_{34}H_{30}O_8$ | |
| 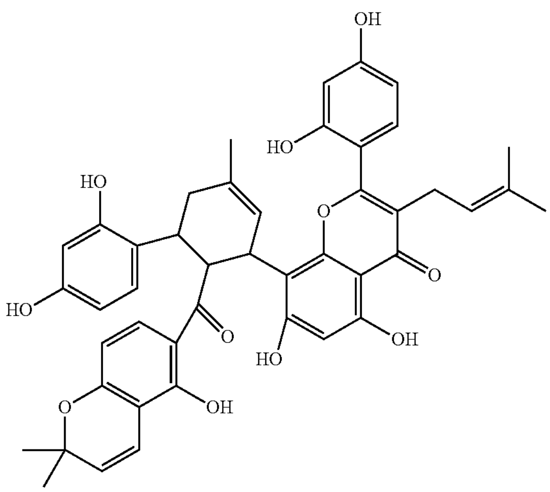 [SMILES: CC(C)=CCc1c(-c2ccc(O)cc2O)oc2c(C3C=C(C)CC(c4ccc(O)cc4O)C3C(=O)c3ccc4c(c3O)C=CC(C)(C)O4)c(O)cc(O)c2c1=O] | Kuwanon W | *Morus lhou* | $C_{45}H_{42}O_{11}$ | 758.820 |
| 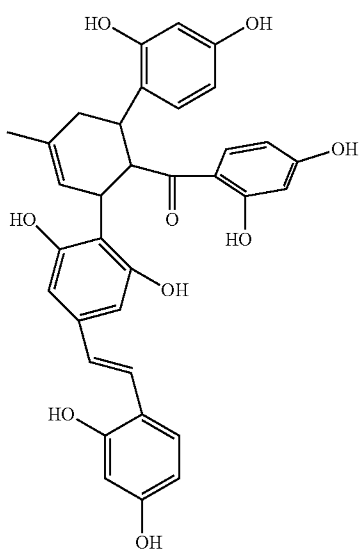 [SMILES: CC1=CC(c2c(O)cc(/C=C/c3ccc(O)cc3O)cc2O)C(C(=O)c2ccc(O)cc2O)C(c2ccc(O)cc2O)C1] | Kuwanon X | *Morus lhou* | $C_{34}H_{30}O_9$ | 582.606 |

TABLE A-continued
List of Exemplary Diels-Alder Adduct Compounds
| Structure | Name | Species | Molecular Formula | M.W. |
|---|---|---|---|---|
| 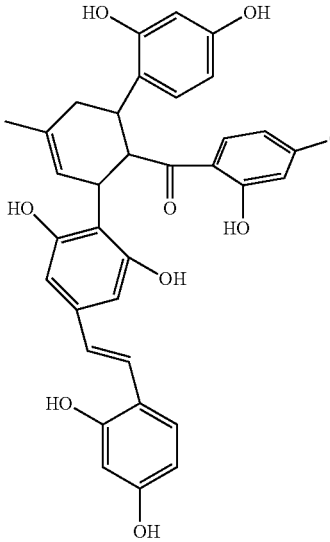 | Kuwanon X; 3"-Epimer | *Morus alba* (white mulberry) | $C_{34}H_{30}O_9$ | 582.606 |
| 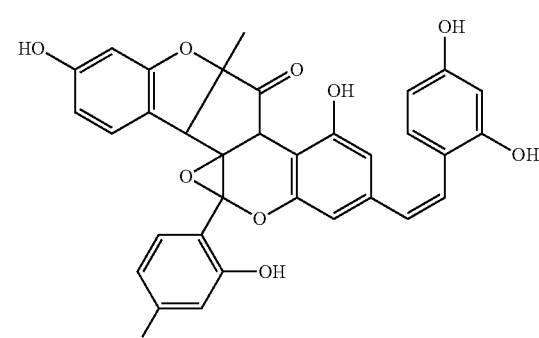 | Kuwanon Z | *Morus alba* (white mulberry) | $C_{34}H_{26}O_{10}$ | 594.573 |
| 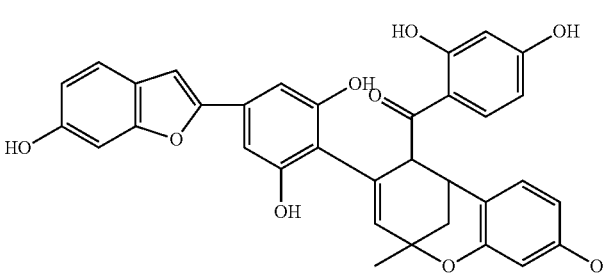 | Mongolicin C | *Morus mongolica* | $C_{34}H_{26}O_9$ | 578.574 |
| 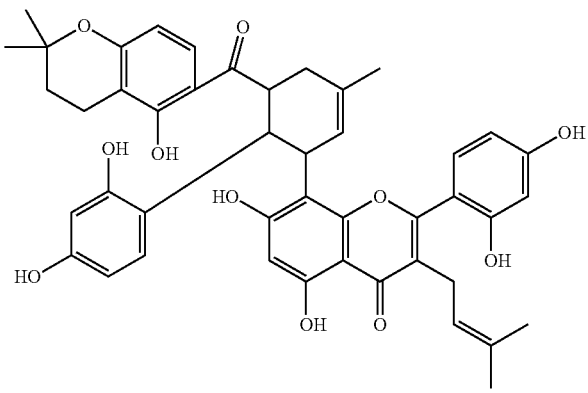 [SMILES: CC(C)=CCc1c(-c2ccc(O)cc2O)oc2c(C3C=C(C)CC(C(=O)c4ccc5c(c4O)CCC(C)(C)O5)C3c3ccc(O)cc3O)c(O)cc(O)c2c1=O] | Moracenin C | *Morus* sp. | $C_{45}H_{44}O_{11}$ | 760.836 |

TABLE A-continued
List of Exemplary Diels-Alder Adduct Compounds
| Structure | Name | Species | Molecular Formula | M.W. |
|---|---|---|---|---|
| 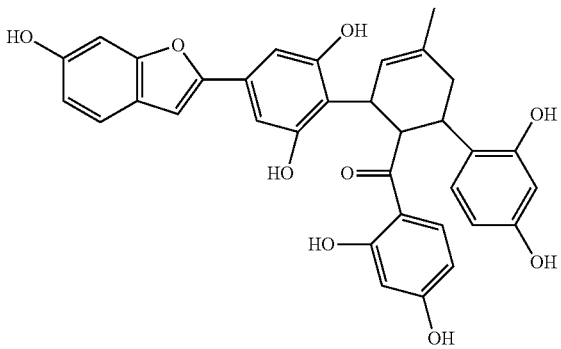 [SMILES: CC1=CC(c2c(O)cc(-c3cc4ccc(O)cc4o3)cc2O)C(C(=O)c2ccc(O)cc2O)C(c2ccc(O)cc2O)C1] | Mulberrofuran C | *Morus bombycis* (*Moraceae*) | | |
| 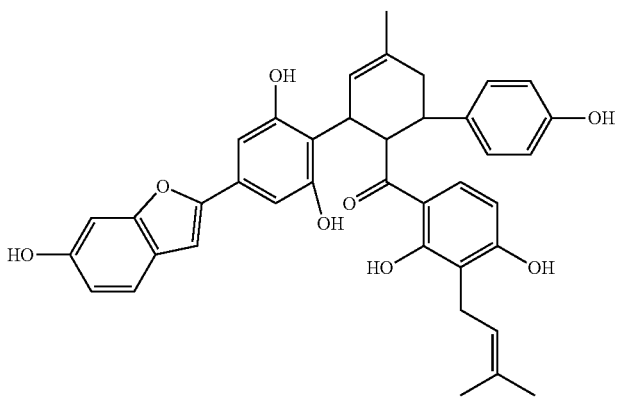 [SMILES: CC(C)=CCc1c(O)ccc(C(=O)C2C(c3c(O)cc(-c4cc5ccc(O)cc5o4)cc3O)C=C(C)CC2c2ccc(O)cc2)c1O] | Mulberrofuran E | *Morus alba* (white mulberry) (Moraceae) | $C_{39}H_{36}O_8$ | 632.709 |
| 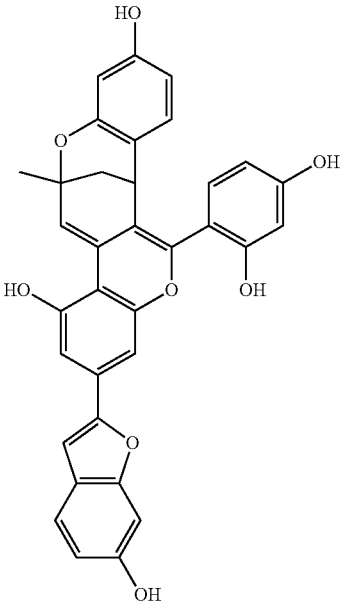 [SMILES: CC12C=C3C(=C(c4ccc(O)cc4O)Oc4cc(-c5cc6ccc(O)cc6o5)cc(O)c43)C(C1)c1ccc(O)cc1O2] | Mulberrofuran I | *Morus bombycis* | $C_{34}H_{24}O_8$ | 560.559 |

TABLE A-continued
List of Exemplary Diels-Alder Adduct Compounds
| Structure | Name | Species | Molecular Formula | M.W. |
|---|---|---|---|---|
| 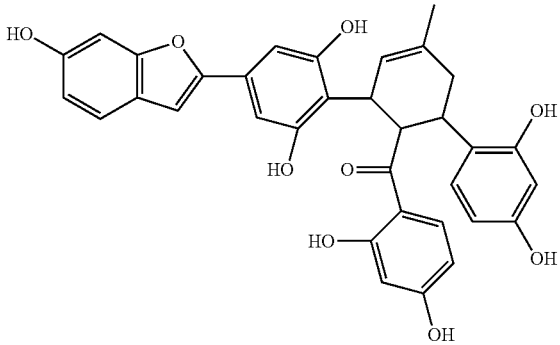 [SMILES: CC1=CC(c2c(O)cc(-c3cc4ccc(O)cc4o3)cc2O)C(C(=O)c2ccc(O)cc2O)C(c2ccc(O)cc2O)C1] | Mulberrofuran J | *Morus lhou* | $C_{34}H_{28}O_9$ | 580.590 |
| 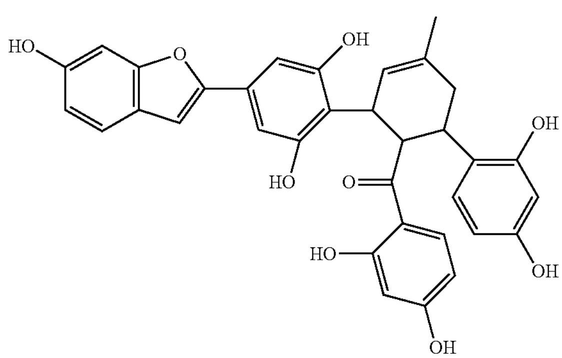 [SMILES: CC1=CC(c2c(O)cc(-c3cc4ccc(O)cc4o3)cc2O)C(C(=O)c2ccc(O)cc2O)C(c2ccc(O)cc2O)C1] | Mulberrofuran J, 2-Epimer | *Morus bombycis* | | |
| 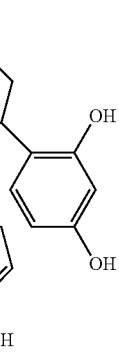 | | | | |
| 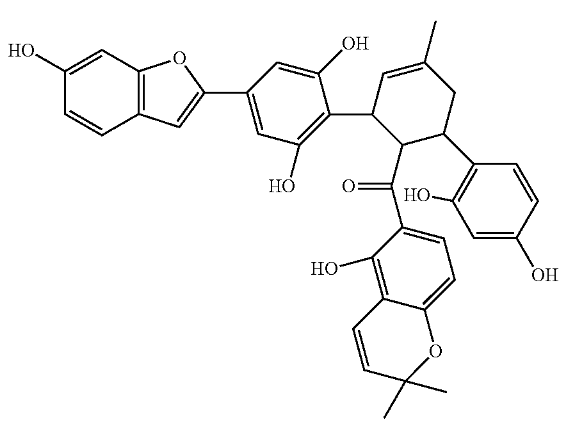 [SMILES: CC1=CC(c2c(O)cc(-c3cc4ccc(O)cc4o3)cc2O)C(C(=O)c2ccc3c(c2O)C=CC(C)(C)O3)C(c2ccc(O)cc2O)C1] | Mulberrofuran O | *Morus alba* | | 646.692 |
| 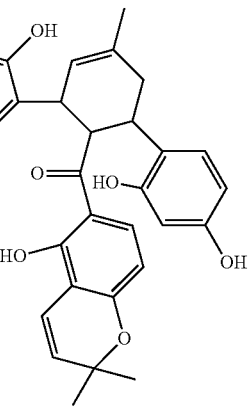 | | | | |

TABLE A-continued
List of Exemplary Diels-Alder Adduct Compounds
| Structure | Name | Species | Molecular Formula | M.W. |
|---|---|---|---|---|
| 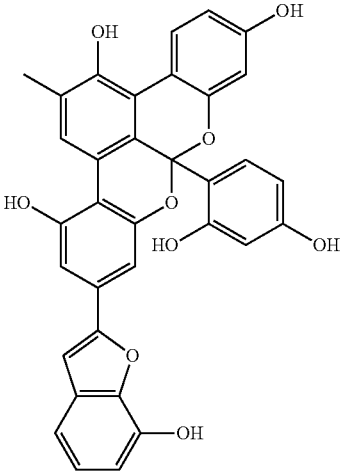 [SMILES: Cc1cc2c3c(c1O)-c1ccc(O)cc1OC3(c1ccc(O)cc1O)Oc1cc(-c3cc4cccc(O)c4o3)cc(O)c1-2] | Mulberrofuran P | *Morus alba* (white mulberry) | $C_{34}H_{22}O_9$ | 574.542 |
| 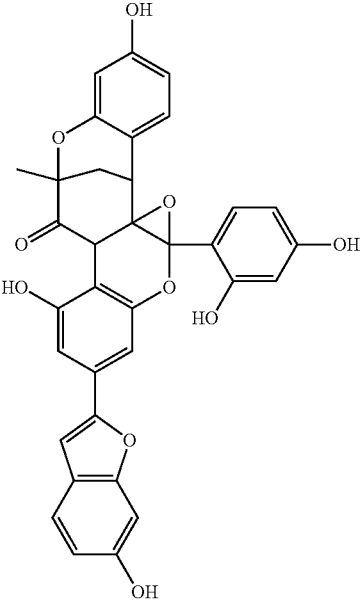 [SMILES: CC12CC(c3ccc(O)cc3O1)C13OC1(c1ccc(O)cc1O)Oc1cc(-c4cc5ccc(O)cc5o4)cc(O)c1C3C2=O] | Mulberrofuran Q | *Morus alba* (white mulberry) | $C_{34}H_{24}O_{10}$ | 592.558 |

TABLE A-continued
List of Exemplary Diels-Alder Adduct Compounds
| Structure | Name | Species | Molecular Formula | M.W. |
|---|---|---|---|---|
| 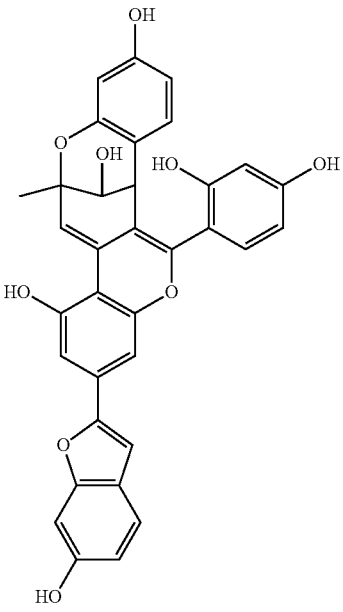 [SMILES: CC12C=C3C(=C(c4ccc(O)cc4O)Oc4cc(-c5cc6ccc(O)cc6o5)cc(O)c43)C(c3ccc(O)cc3O1)C2O] | Mulberrofuran S | *Morus alba* (white mulberry) | $C_{34}H_{24}O_9$ | 576.558 |
| 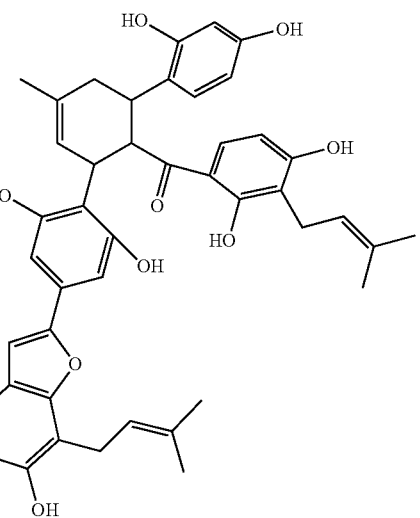 | Mulberrofuran T | *Morus alba* (white mulberry) | $C_{44}H_{44}O_9$ | 716.826 |

TABLE A-continued
List of Exemplary Diels-Alder Adduct Compounds
| Structure | Name | Species | Molecular Formula | M.W. |
|---|---|---|---|---|
| 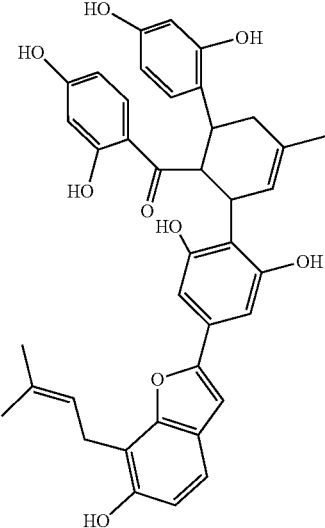 [SMILES: CC(C)=CCc1c(O)ccc2cc(-c3cc(O)c(C4C=C(C)C[C@@H](c5ccc(O)cc5O)C4C(=O)c4ccc(O)cc4O)c(O)c3)oc12] | Mulberrofuran U | *Morus insignis* | $C_{39}H_{36}O_9$ | 648.708 |
| 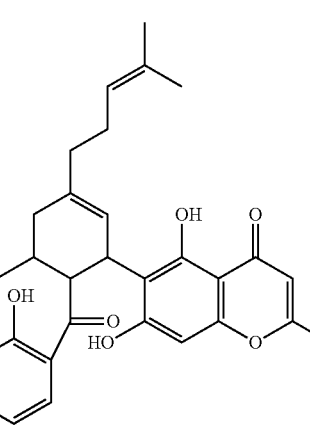 | Multicaulisin | *Morus multicaulis* | $C_{40}H_{36}O_{11}$ | 692.718 |
| 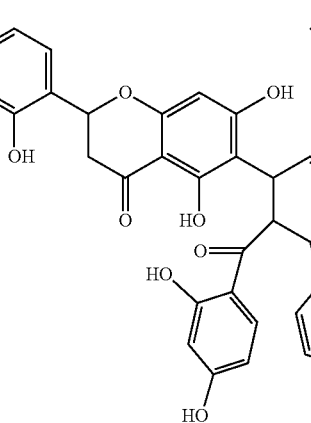 | Sanggenol G | *Morus cathayana* | $C_{30}H_{34}O_7$ | 694.734 |

TABLE A-continued
List of Exemplary Diels-Alder Adduct Compounds
| Structure | Name | Species | Molecular Formula | M.W. |
|---|---|---|---|---|
| 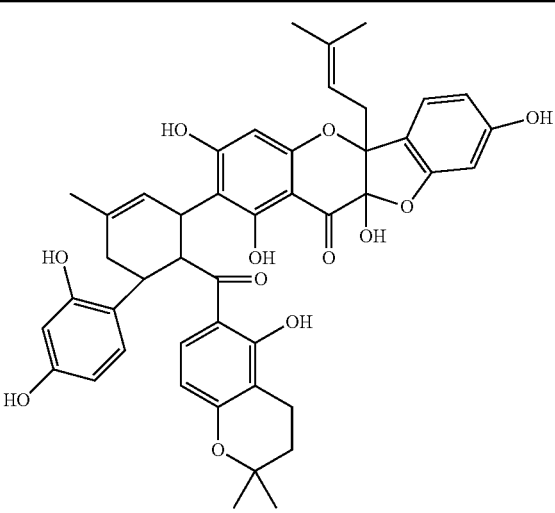 | Sanggenol J | Morus cathayana | $C_{45}H_{44}O_{12}$ | 776.835 |
| 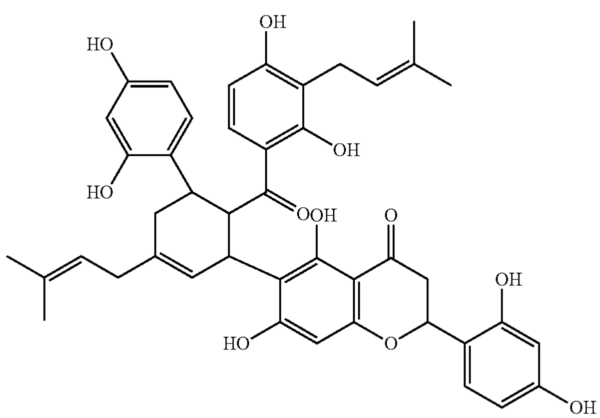 [SMILES: CC(C)=CCC1=CC(c2c(O)cc3c(c2O)C(=O)CC(c2ccc(O)cc2O)O3)C(C(=O)c2ccc(O)c(CC=C(C)C)c2O)C(c2ccc(O)cc2O)C1] | Sanggenol M | Morus mongolica | $C_{44}H_{44}O_{11}$ | 748.825 |
| 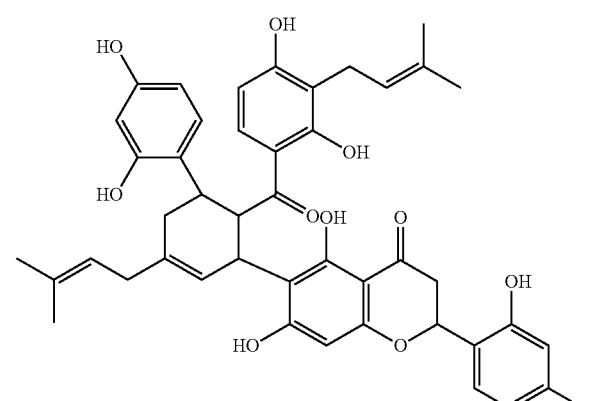 | | | | |
| 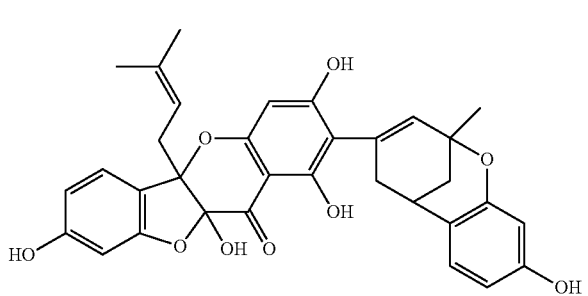 [SMILES: CC(C)=CCC12Oc3cc(O)c(C4=CC5(C)CC(C4)c4ccc(O)cc4O5)c(O)c3C(=O)C1(O)Oc1cc(O)ccc12] | Sanggenon B | Morus | $C_{33}H_{30}O_9$ | 570.595 |

TABLE A-continued

List of Exemplary Diels-Alder Adduct Compounds

| Structure | Name | Species | Molecular Formula | M.W. |
|---|---|---|---|---|
| 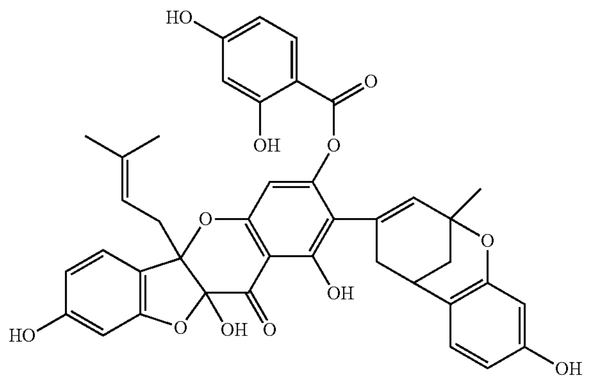 [SMILES: CC(C)=CCC12Oc3cc(OC(=O)c4ccc(O)cc4O)c(C4=CC5(C)CC(C4)c4ccc(O)cc4O5)c(O)c3C(=O)C1(O)Oc1cc(O)ccc12] | Sanggenon B; 7-O-(2,4-Dihydroxybenzoyl) (Sanggenon S) | *Morus* sp | $C_{40}H_{34}O_{12}$ | 706.701 |
| 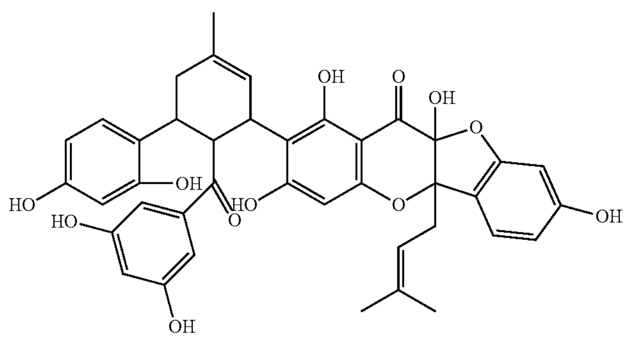 [SMILES: CC(C)=CCC12Oc3cc(O)c(C4C=C(C)CC(c5ccc(O)cc5O)C4C(=O)c4cc(O)cc(O)c4)c(O)c3C(=O)C1(O)Oc1cc(O)ccc12] | Sanggenon D | *Morus cathayana* | $C_{40}H_{36}O_{12}$ | 708.717 |
| 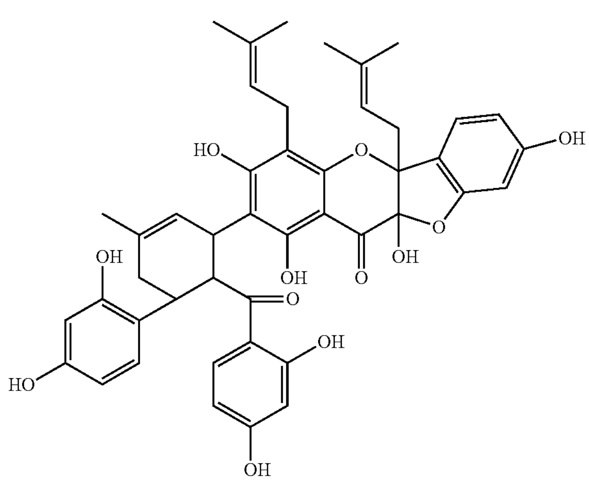 [SMILES: CC(C)=CCc1c(O)c(C2C=C(C)CC(c3ccc(O)cc3O)C2C(=O)c2ccc(O)cc2O)c(O)c2c1OC1(CC=C(C)C)c3ccc(O)cc3OC1(O)C2=O] | Sanggenon E | *Morus* Spp. | $C_{45}H_{44}O_{12}$ | 776.835 |

TABLE A-continued

List of Exemplary Diels-Alder Adduct Compounds

| Structure | Name | Species | Molecular Formula | M.W. |
|---|---|---|---|---|
| 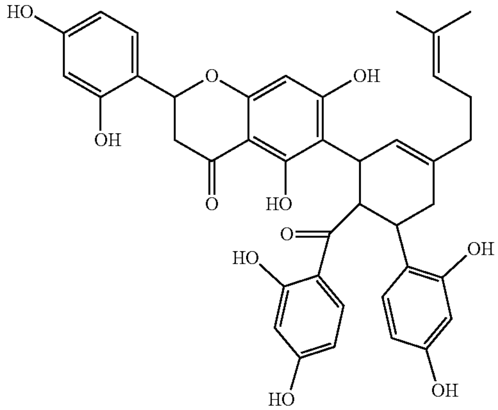 [SMILES: CC(C)=CCCC1=CC(c2c(O)cc3c(c2O)C(=O)CC(c2ccc(O)cc2O)O3)C(C(=O)c2ccc(O)cc2O)C(c2ccc(O)cc2O)C1] | Sanggenon G | Morus alba | $C_{40}H_{38}O_{11}$ | 694.734 |
| 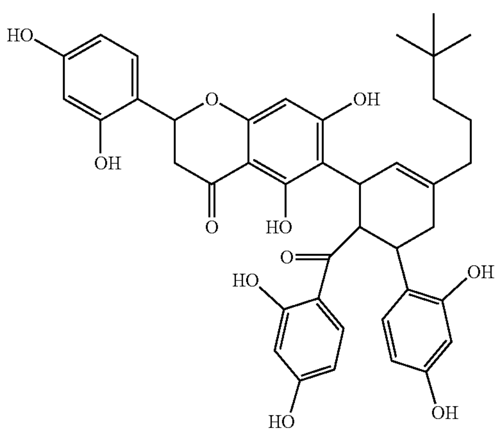 [SMILES: CC(C)(C)CCCC1=CC(c2c(O)cc3c(c2O)C(=O)CC(c2ccc(O)cc2O)O3)C(C(=O)c2ccc(O)cc2O)C(c2ccc(O)cc2O)C1] | Sanggenon G; 14,15-Dihydro, 15-hydroxy | Morus sp. | $C_{40}H_{40}O_{12}$ | 712.749 |
| 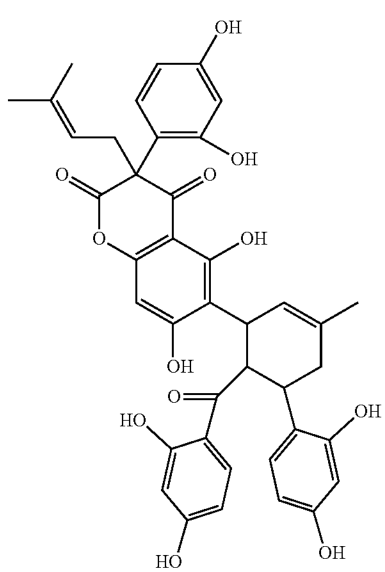 [SMILES: CC(C)=CCC1(c2ccc(O)cc2O)C(=O)Oc2cc(O)c(C3C=C(C)CC(c4ccc(O)cc4O)C3C(=O)c3ccc(O)cc3O)c(O)c2C1=O] | Sanggenon Q | Morus mongolica | $C_{40}H_{36}O_{12}$ | 708.717 |

TABLE A-continued

List of Exemplary Diels-Alder Adduct Compounds

| Structure | Name | Species | Molecular Formula | M.W. |
|---|---|---|---|---|
| 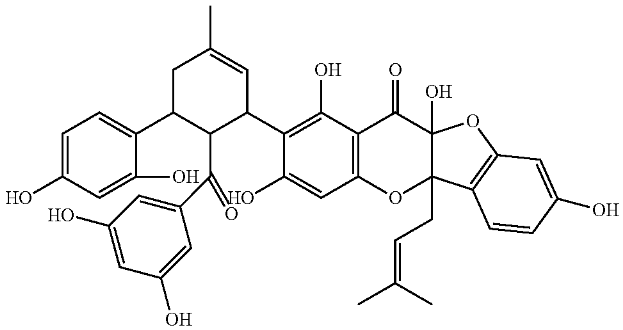 [SMILES: CC(C)=CCC12Oc3cc(O)c(C4C=C(C)CC(c5ccc(O)cc5O)C4C(=O)c4cc(O)cc(O)c4)c(O)c3C(=O)C1(O)Oc1cc(O)ccc12] | Sanggenon D; 3'-Epimer | *Morus cathayana* | $C_{40}H_{36}O_{12}$ | 708.717 |
| 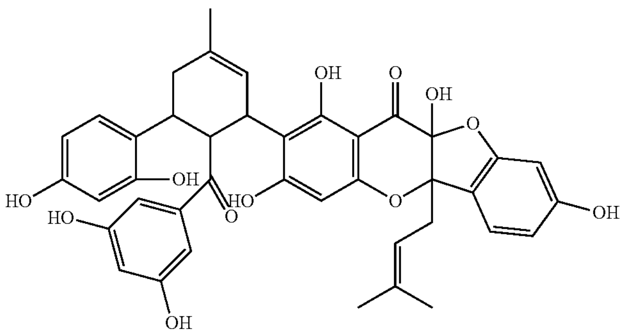 [SMILES: CC(C)=CCC12Oc3cc(O)c(C4C=C(C)CC(c5ccc(O)cc5O)C4C(=O)c4cc(O)cc(O)c4)c(O)c3C(=O)C1(O)Oc1cc(O)ccc12] | Sanggenon D; 2,3,3'-Triepimer | *Morus cathayana* | $C_{40}H_{36}O_{12}$ | 708.717 |
| 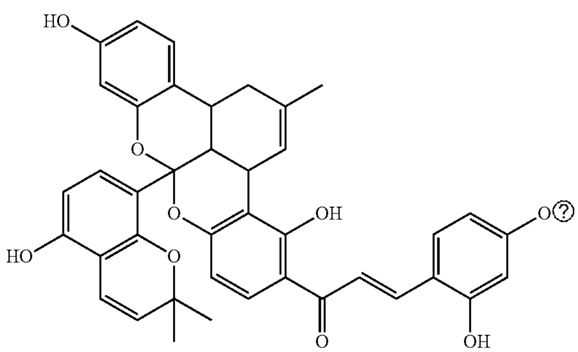 [SMILES: CC1=CC2c3c(ccc(C(=O)/C=C/c4ccc(O)cc4O)c3O)OC3(c4ccc(O)c5c4OC(C)(C)C=C5)Oc4cc(O)ccc4C(C1)C23] | Sorocein B | *Sorocea bonplandii* | $C_{40}H_{34}O_9$ | 658.703 |
| 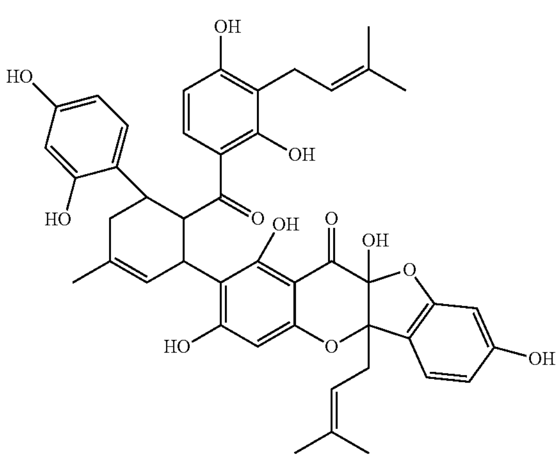 [SMILES: CC(C)=CCc1c(O)ccc(C(=O)C2C(c3c(O)cc4c(c3O)C(=O)C3(O)Oc5cc(O)ccc5C3(CC=C(C)C)O4)C=C(C)CC2c2ccc(O)cc2O)c1O] | Sorocein H | *Sorocea bonplandii* (*Moraceae*) and *Morus* spp. | $C_{45}H_{44}O_{12}$ | 776.835 |

TABLE A-continued
List of Exemplary Diels-Alder Adduct Compounds
| Structure | Name | Species | Molecular Formula | M.W. |
|---|---|---|---|---|
| 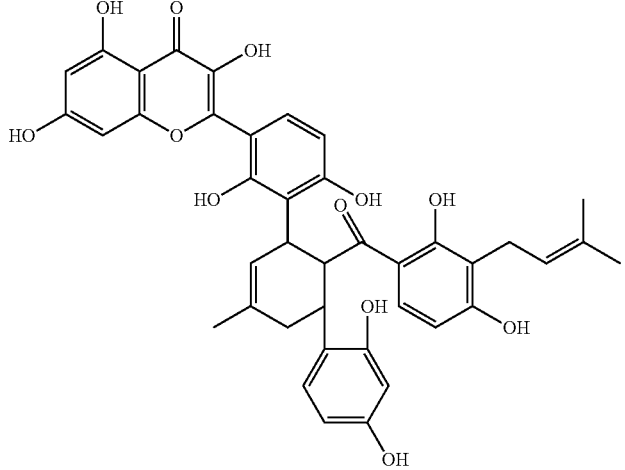 [SMILES: CC(C)=CCc1c(O)ccc(C(=O)C2C(c3c(O)ccc(-c4oc5cc(O)cc(O)c5c(=O)c4O)c3O)C=C(C)CC2c2ccc(O)cc2O)c1O] | Wittiorumin B | *Morus wittiorum* | $C_{40}H_{36}O_{12}$ | 708.717 |
| 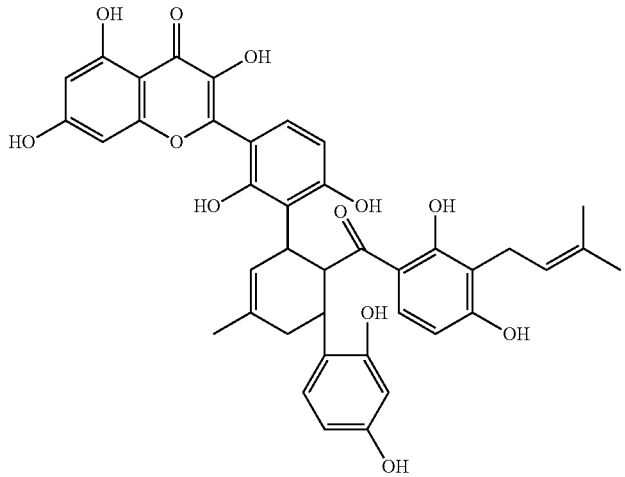 [SMILES: CC(C)=CCc1c(O)ccc(C(=O)C2C(c3c(O)ccc(-c4oc5cc(O)cc(O)c5c(=O)c4O)c3O)C=C(C)CC2c2ccc(O)cc2O)c1O] | Wittiorumin B; 1″-Epimer, 2′-deoxy | *Morus wittiorum* | $C_{40}H_{36}O_{11}$ | 692.718 |
| 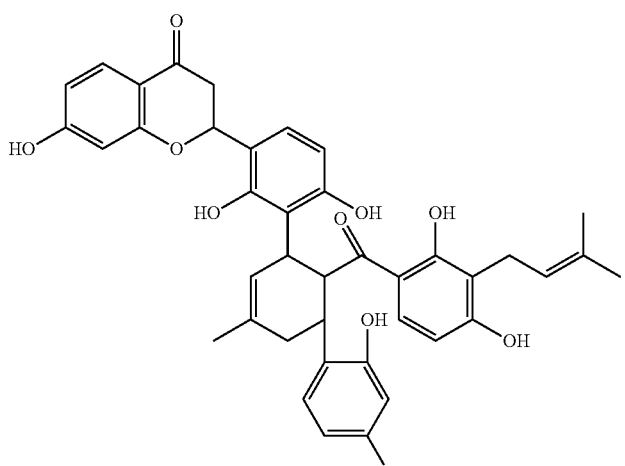 | Wittiorumin E | *Morus wittiorum* | $C_{40}H_{38}O_{10}$ | 678.734 |

TABLE A-continued

List of Exemplary Diels-Alder Adduct Compounds

| Structure | Name | Species | Molecular Formula | M.W. |
|---|---|---|---|---|
| 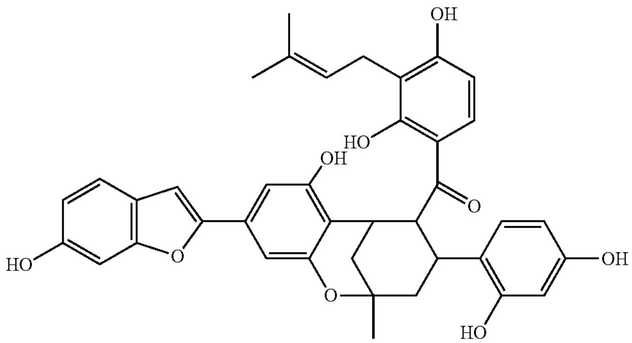 [SMILES: CC(C)=CCc1c(O)ccc(C(=O)C2C(c3ccc(O)cc3O)CC3(C)CC2c2c(O)cc(-c4cc5ccc(O)cc5o4)cc2O3)c1O] | Wittiorumin F | Morus wittiorum | $C_{39}H_{36}O_9$ | 648.708 |
| 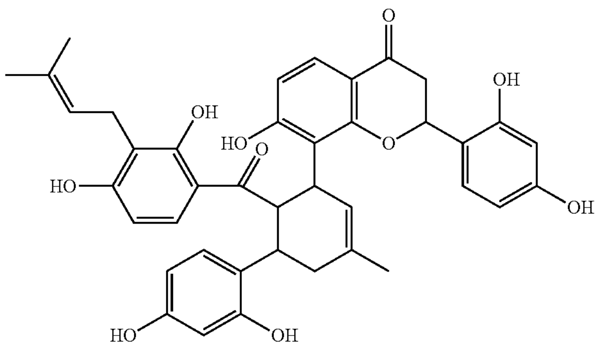 [SMILES: CC(C)=CCc1c(O)ccc(C(=O)C2C(c3c(O)ccc4c3OC(c3ccc(O)cc3O)CC4=O)C=C(C)CC2c2ccc(O)cc2O)c1O] | Wittiorumin G | Morus wittiorum | $C_{40}H_{38}O_{10}$ | 678.734 |
| 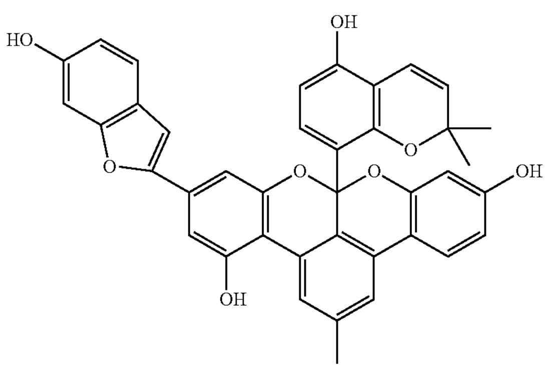 [SMILES: Cc1cc2c3c(c1)-c1c(O)cc(-c4cc5ccc(O)cc5o4)cc1OC3(c1ccc(O)c3c1OC(C)(C)C=C3)Oc1cc(O)ccc1-2] | Yunanensin A | Morus yunnanensis | $C_{39}H_{28}O_8$ | 624.645 |

Compounds in Table A and Examples 3, 5, 6 and 68 can be extracted, isolated or purified from the indicated plant species or certain plant parts (e.g., from the bark, trunk, trunk bark, stem bark, root, root bark, bark surface (such as periderm or polyderm, which may include phellem, phellogen, phelloderm, or any combination thereof), leaves, fruits, flowers, other plant parts, or any combination thereof) or can be prepared synthetically or semi-synthetically as described in more detail in PCT Application No. PCT/US2013/43188, which methods of synthesis are incorporated herein by reference. In certain embodiments, one or more compounds of Table A and Examples 3, 5, 6 and 68 are enriched for or are the major active ingredients in an extract of the indicated plant species, wherein the enriched extract is obtained from a whole plant or certain plant parts, such as leaves, bark, trunk, trunk bark, stems, stem bark, twigs, tubers, root, root bark, bark surface (such as periderm or polyderm, which may include phellem, phellogen, phelloderm, or any combination thereof), young shoots, rhizomes, seed, fruit, androecium, gynoecium, calyx, stamen, petal, sepal, carpel (pistil), flower, or any combination thereof.

In further embodiments, major active ingredients in an extract of *Morus* comprise prenylated flavonoids and stilbenes (such as those provided in Table A and Examples 3, 5, 6 and 68), wherein the extract is enriched for these active ingredients from root bark, leaves, twigs, or a combination thereof. In certain embodiments, a *Morus* extract is enriched for prenylated flavonoids and stilbenes, wherein the extract comprises from about 1% to about 25% prenylated flavonoids and from about 1% to about 25% stilbenes, or wherein the extract comprises from about 2% to about 6% prenylated flavonoids and from about 2% to about 6% stilbenes, or wherein the extract comprises at least 3% prenylated flavonoids and at least 3% stilbenes (weight to weight).

In certain embodiments, provided herein are *Morus* extracts enriched for one or more prenylated flavonoids or chalconoids and one or more stilbenes, wherein the one or more prenylated flavonoids are compounds having a structure of Formula (III) or (IV):

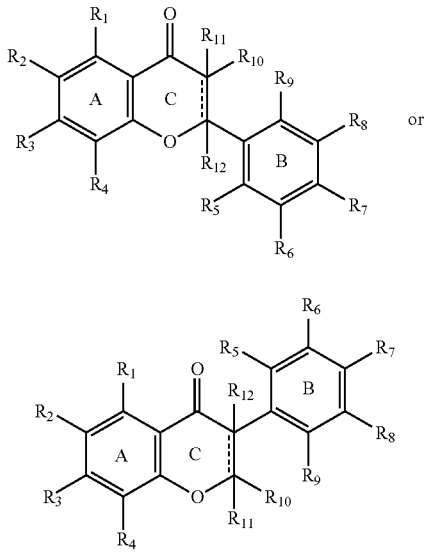

or a pharmaceutically or nutraceutically acceptable salt, tautomer, glycoside, prodrug or stereoisomer thereof, wherein $R_1$-$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkyl carbonyl, aralkylcarbonyl or a bond to a compound of structure (III) or (IV); or one of $R_1$-$R_{12}$ joins with another one of $R_1$-$R_{12}$ to form a ring, and the remaining $R_1$-$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl or a bond to a compound of structure (III) or (IV), provided that all valencies are satisfied;

the chalcanoid is a compound of structure (V):

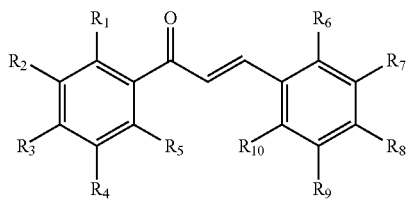

or a pharmaceutically or nutraceutically acceptable salt, tautomer, glycoside, prodrug or stereoisomer thereof, wherein $R_1$-$R_{10}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, alkyl carbonyl, or aralkylcarbonyl, provided that all valencies are satisfied; and the one or more stilbenes are compounds having a structure of Formula (I) or (II):

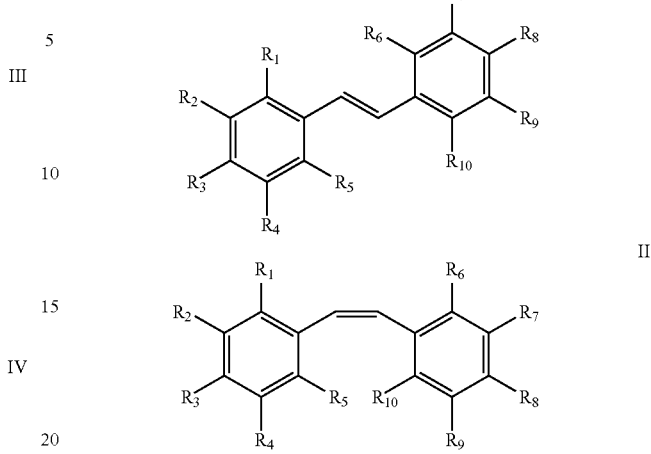

wherein $R_1$-$R_{10}$ are each independently a H, hydroxyl, glycoside, prenyl, flavonoid, chalcone, halogen, sulfhydryl, amino, aldehyde, $C_{1-12}$ alkyl, $C_{1-12}$ alkenyl, $C_{1-12}$ alkoxy, $C_{1-12}$ alkthio, $C_{1-12}$ alkyamino, aryl, heteroaryl, aralkyl, alkylcarbonyl, or aralkylcarbonyl.

In further embodiments, the one or more prenylayted flavonoids are compounds having a structure of Formula (III), (IV) or (V), wherein the optional double bond is present in ring C, $R_{11}$ and $R_{12}$ are absent, and $R_{10}$ is a prenyl group. In still further embodiments, the one or more prenylayted flavonoids are compounds having a structure of Formula (III), (IV) or (V), wherein the at least one of $R_1$-$R_9$ is a prenyl group and $R_{10}$-$R_{12}$ are independently H or hydroxyl. In certain specific embodiments, the prenylated flavonoids include Albanin G, Kuwanon G, Morusin, morusinol, Sanggenon, isoxanthoumol, glabridin, cathayanon A, or any combination thereof. In certain embodiments, the one or more stilbenes are compounds having a structure of Formula (I) or (II), wherein $R_1$-$R_{10}$ are each independently a H, hydroxyl, glycoside, or $C_{1-4}$ alkoxy. In further embodiments, the one or more stilbenes are compounds having a structure of Formula (I) or (II), wherein $R_1$, $R_5$, $R_6$ and $R_{10}$ are H. In still further embodiments, the one or more stilbenes are compounds having a structure of Formula (I) or (II), wherein $R_2$ is a glucoside, or $R_2$ and $R_8$ are glycosides, and one or more of $R_4$, $R_9$, and $R_{10}$ are hydroxyl. In yet further embodiments, the one or more stilbenes are compounds having a structure of Formula (I) or (II), wherein $R_1$, $R_5$, and $R_6$ are H, and one or more of $R_2$-$R_4$ and $R_7$-$R_{10}$ are independently hydroxyl, $C_{1-3}$ alkoxy, or any combination thereof. In certain specific embodiments, a stilbene compound includes oxyresveratrol, resveratrol, piceatannol, pinosylvin, 3,4'-dihydroxystilbene, combretastatin A-1, pterostilbene, rhapontigenin, and a stilbene glycoside includes mulberroside A, rhaponticin, piceid, astringin, or any combination of these stilbenes or stilbene glycosides.

In some embodiments, the flavonoid is a compound of structure (III) and in other embodiments the flavonoid is a compound of structure (IV). In some other embodiments, at least one of $R_1$-$R_{12}$, such as $R_{10}$ is prenyl. In other embodiments, polyflavonoids are provided and at least one of $R_1$-$R_{12}$ in the compounds of structure (III) or (IV) is a bond to a compounds of structure of (III) or (IV) (i.e., the compound comprises more than one flavonoid of structure (III) and/or (IV)).

In some other embodiments of the compounds of structure (III) or (IV), $R_1$-$R_{12}$ is H, hydroxyl, a prenyl group or cycloalkyl. For example, in some embodiments the cycloalkyl is substituted and/or comprises one or more carbon-carbon double bonds (i.e., is unsaturated). The optional substitutents are typically selected from aryl, such as phenyl, and aryl carbonyl. Accordingly, in some further embodiments, the flavonoid has one of the following structures (IIIa) or (IVa):

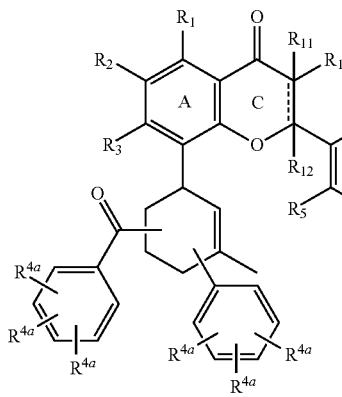

IIIa

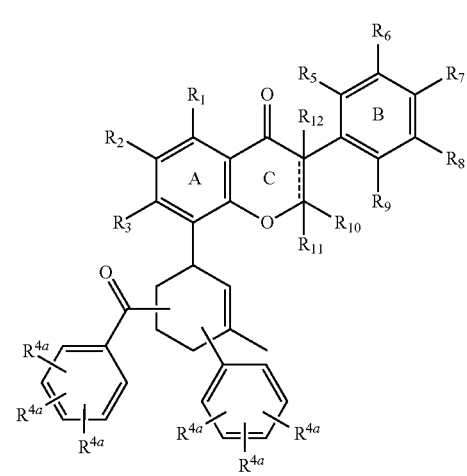

IVa wherein $R^{4a}$ is, at each occurrence, independently H, hydroxyl or a prenyl group.

In certain embodiments of the compounds of structure (IIIa) or (IVa), $R_1$-$R_3$ and $R_5$-$R_{12}$ are each independently selected from H, hydroxyl and a prenyl group. In certain embodiments, at least one of $R_1$-$R_3$, $R_{4a}$ or $R_5$-$R_{12}$ is prenyl, for example in some embodiments, $R_{10}$ is prenyl. In other embodiments of the compounds of structure (IIIa) or (IVa), at least two of $R_1$-$R_3$, $R_{4a}$ or $R_5$-$R_{12}$ is hydroxyl.

In some more specific embodiments, the flavonoid has one of the following structures:

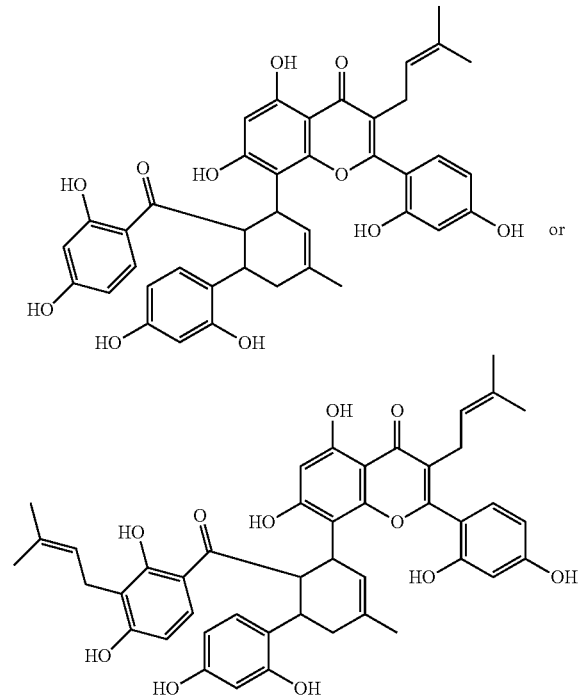

In other embodiments, one of $R_1$-$R_{12}$ joins with another one of $R_1$-$R_{12}$ to form a ring and the remaining $R_1$-$R_{12}$ are H, hydroxyl or a prenyl group. In certain of these embodiments, the ring is a heterocyclic ring, for example a cyclic ether ring. Accordingly, in certain embodiments the flavonoid has one of the following structures (IIIb) or (IVb):

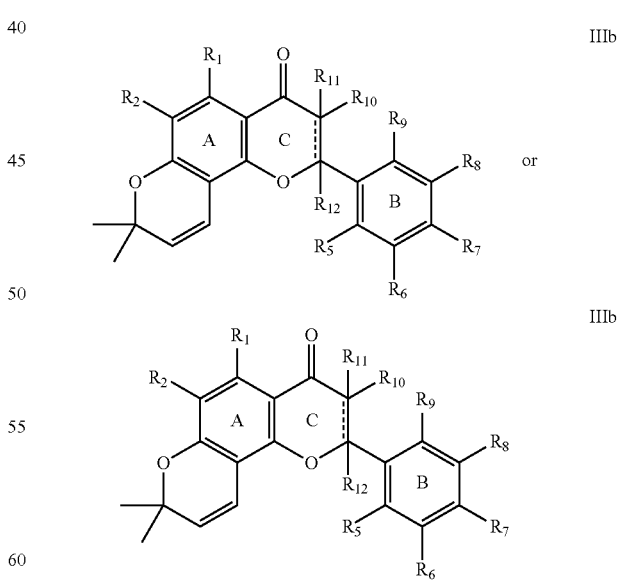

In certain embodiments of the compounds of structure (IIIb) or (IVb), $R_1$, $R_2$ and $R_5$-$R_{12}$ are each independently selected from H, hydroxyl and a prenyl group. In certain embodiments, at least one of $R_1$, $R_2$ or $R_5$-$R_{12}$ is prenyl, for example in some embodiments, $R_{10}$ is prenyl. In other embodiments of the compounds of structure (IIIb) or (IVb), at least two of $R_1$, $R_2$ or $R_5$-$R_{12}$ is hydroxyl. In certain embodiments, the flavonoid has the following structure:

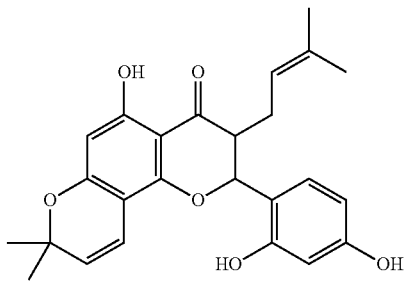 [SMILES: CC(C)=CCC1C(=O)c2c(O)cc3c(c2OC1c1ccc(O)cc1O)C=CC(C)(C)O3]

In various other embodiments, $R_1$-$R_{10}$ of the chalcanoid of structure (V) are each independently selected from H, hydroxyl, a prenyl group, and $C_{1-12}$ alkoxy.

The biologically active flavans of this disclosure may be obtained by synthetic methods or extracted from one or more plants, such as Acacia, Uncaria, or both. In certain embodiments, an Acacia plant species is selected from A. angustifolia, A. ataxacantha, A. berlandieri, A. bonariensis, A. brevispica, A. catechu, A. chundra, A. concinna, A. floribunda, A. greggii, A. interior, A. macilenta, A. mellifera, A. merrallii, A. occidentalis, A. peninsularis, A. pennata, A. pennatula, A. polyacantha, A. polyphylla, A. riparia, A. roemeriana, A. senegal, A. sinuata, A. tamarindifolia, A. tenuifolia, A. victoriae, A. visco, or any combination thereof (for exemplary Acacia extracts and flavans, see U.S. Pat. No. 8,124,134). In certain embodiments, an Uncaria plant species is selected from U. acida, U. africana, U. attenuate, U. bernaysii, U. borneensis, U. callophylla, U. cordata, U. elliptica, Uncaria gambir, U. guianensis, U. hirsute, U. homomalla, U. lanosa, U. longiflora, U. macrophylla, U. orientalis, U. rhynchophylla, U. scandens, U. sessilifructus, U. setiloba, U. sinensis, U. sterrophylla, U. tomentosa, U. wangii, or any combination thereof (for exemplary Uncaria extracts and flavans, see U.S. Patent Publication No. 2007/0264361).

In further embodiments, a composition of this disclosure comprises an Acacia catechu extract enriched for flavans containing catechin, epicatechin, or a combination thereof. In still further embodiments, a composition of this disclosure comprises an Uncaria gambir extract enriched for flavans containing catechin, epicatechin, or a combination thereof. In yet further embodiments, an Acacia extract enriched for flavans is from Acacia catechu, or an Acacia extract enriched for flavans is a mixture of extracts from one, two, three, four, five or more different Acacia species, Uncaria species, or from other sources. In other embodiments, an Uncaria extract enriched for flavans is from Uncaria gambir, or an Uncaria extract enriched for flavans is a mixture of extracts from one, two, three, four, five or more different Uncaria species, Acacia species, other sources (e.g., different plant such as green tea, synthetic), or any combination thereof. For example, a composition of this disclosure comprises a mixture of an Acacia catechu extract enriched for flavans containing catechin, epicatechin, or both and an Uncaria gambir extract enriched for flavans containing catechin, epicatechin, or both.

In certain embodiments, major active ingredients in an extract of Acacia comprise flavans containing catechin, epicatechin, or both, wherein the extract is enriched for these active ingredients from roots, bark, or a combination thereof. In certain embodiments, major active ingredients in an extract of Uncaria comprise flavans containing catechin, epicatechin, or both, wherein the extract is enriched for these active ingredients from leaves.

In certain embodiments, provided herein are Acacia or Uncaria extracts enriched for one or more flavans containing catechin, epicatechin, or both, wherein the flavans are compounds having a structure of Formula (VI):

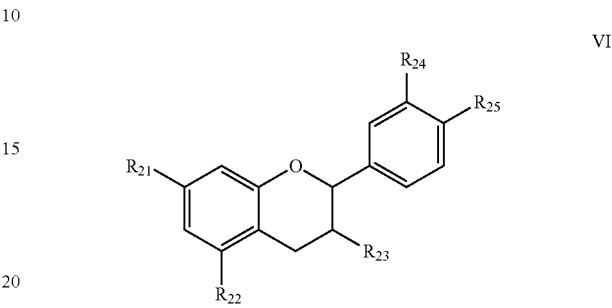

wherein $R_{21}$, $R_{22}$, $R_{23}$, $R_{24}$ and $R_{25}$ are independently selected from a H, —OH, —SH, —OCH$_3$, —SCH$_3$, —OR, —SR, —NH$_2$, —NRH, —NR$_2$, —NR$_3^+$X$^-$, esters of substitution groups, independently selected from the group consisting of gallate, acetate, cinnamoyl and hydroxylcinnamoyl esters, trihydroxybenzoyl esters and caffeoyl esters; a carbon, oxygen, nitrogen or sulfur glycoside of a single or a combination of multiple sugars including aldopentose, methyl aldopentose, aldohexose, ketohexose; dimer, trimer or other polymerized flavans;

wherein R is a $C_{1-10}$ alkyl group; and

X is a pharmaceutically acceptable counter anion of hydroxyl, chloride, iodide, sulfate, phosphate, acetate, fluoride, or carbonate.

In certain embodiments, there are provided herein Curcuma extracts comprising curcuminoids. In further embodiments, a Curcuma longa extract is enriched for curcuminoids, such as curcumin (diferuloylmethane), demethoxycurcumin, bisdemethoxy-curcumin, casumunin A, cassumunin B, or any combination thereof. The biologically active curcuminoids and analogues therof of this disclosure may be obtained by synthetic methods (see Anand et al., Biochem. Pharmacol. 76:1590, 2008) or extracted from one or more plants, such as Curcuma plants, Zingiber plants, or both.

Exemplary species of the Curcuma genus of the instant disclosure include C. aeruginosa, C. albicoma, C. albiflora, C. alismatifolia, C. amada, C. amarissima, C. americana, C. angustifolia, C. aromatics, C. attenuata, C. aurantiaca, C. australasica, C. bakeriana, C. bicolor, C. bhatii, C. brog, C. burttii, C. caesia, C. candida, C. cannanorensis, C. caulina, C. careyana, C. ceratotheca, C. chuanezhu, C. chuanhuangjiang, C. chuanyujin, C. coccinea, C. cochinchinensis, C. codonantha, C. coerulea, C. colorata, C. comosa, C. cordata, C. cordifolia, C. coriacea, C. decipiens, C. domestica, C. ecalcarata, C. ecomata, C. elata, C. erubescens, C. euchroma, C. exigua, C. ferruginea, C. flaviflora, C. glans, C. glaucophylla, C. gracillima, C. grahamiana, C. grandiflora, C. haritha, C. harmandii, C. heyneana, C. inodora, C. karnatakensis, C. kuchoor, C. kudagensis, C. künstleri, C. kurzii, C. kwangsiensis, C. lanceolata, C. larsenii, C. latiflora, C. latifolia, C. leucorhiza, C. leucorrhiza, C. loerzingii, C. longa, C. longiflora, C. longispica, C. lutea, C. malabarica, C. mangga, C. meraukensis, C. montana, C. musacea, C. mutabilis, C. neilgherrensis, C. nilamburensis,

*C. ochrorhiza, C. officinalis, C. oligantha, C. ornata, C. pallida, C. parviflora, C. parvula, C. peethapushpa, C. petiolata, C. phaeocaulis, C. picta-C. pierreana, C. plicata, C. porphyrotaenia, C. prakasha, C. pseudomontana, C. purpurascens, C. purpurea, C. raktakanta, C. ranadei, C. reclinata, C. rhabdota, C. rhomba, C. roscoeana, C. rotunda, C. rubescens, C. rubricaulis, C. rubrobracteata, C. sattayasaii, C. sessilis, C. sichuanensis, C. singularis, C. soloensis, C. sparganiifolia, C. speciosa, C. spicata, C. stenochila, C. strobilifera, C. sulcata, C. sumatrana, C. sylvatica, C. sylvestris, C. thalakaveriensis, C. thorelii, C. trichosantha, C. vamana, C. vellanikkarensis, C. viridiflora, C. vitellina-C. wenchowensis, C. wenyujin, C. xanthorrhiza, C. yunnanensis, C. zedoaria, C. zedoaroides, C. zerumbet.*

In certain embodiments, a *Curcuma* extract enriched for curcuminoids is from *Curcuma longa*, or a *Curcuma* extract enriched for curcuminoids is a mixture of extracts from one, two, three, four, five or more different *Curcuma* species or from other sources. For example, a composition comprising curcuminoids may be a *Curcuma* extract (e.g., *Curcuma longa*) mixed with synthetic curcuminoids, or a mixture of a *Curcuma* extract (e.g., *Curcuma longa*) enriched for curcuminoids with a *Zingiber cassumunar* extract enriched for curcuminoids, *Curcuma phaeocaulis* extract enriched for curcuminoids, *Curcuma. xanthorrhiza* extract enriched for curcuminoids, or any combination thereof. In other embodiments, a *Curcuma* extract enriched for one or more curcuminoids (e.g., curcumin, demethoxy-curcumin, bisdemethoxy-curcumin, casumunin A, cassumunin B, or any combination thereof) may be from root, rhizome, or a combination thereof.

In certain embodiments, a composition of this disclosure comprises an *Acacia* extract containing or enriched for one or more flavans as described herein or in U.S. Pat. No. 8,124,134, and a *Morus* extract containing or enriched for at least one Diels-Alder adduct of a chalcone and a prenylphenyl moiety, prenylated flavonoid, stilbene, or any combination thereof. In certain embodiments, a composition comprises an *Acacia* extract containing or enriched for one or more flavans as described herein or in U.S. Pat. No. 8,124,134 and a *Morus* extract containing or enriched for one or more compounds listed in Table A and Examples 3, 5, 6 and 68. In still further embodiments, a composition comprises an *Acacia* extract containing or enriched for catechin, epicatichin, or both, and a *Morus* extract containing or enriched for one or more prenylated flavonoids, one or more stilbenes, or any combination thereof. In other embodiments, a composition comprises a mixture of a *Morus* extract enriched for one or more prenylated flavonoids and one or more stilbenes, and an *Acacia* extract enriched for flavans.

In further embodiments, a composition of this disclosure comprises a mixture of a *Morus* extract enriched for one or more prenylated flavonoids and one or more stilbenes, and an *Acacia* extract enriched for one or more flavans, wherein the one or more prenylated flavonoids are compounds having a structure of Formula (III) or (IV):

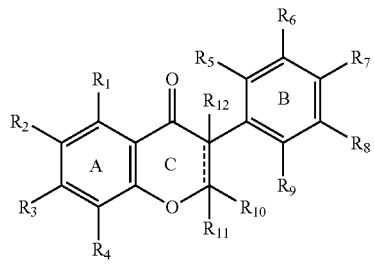

or a pharmaceutically or nutraceutically acceptable salt, tautomer, glycoside, prodrug or stereoisomer thereof, wherein $R_1$-$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkyl carbonyl, aralkylcarbonyl or a bond to a compound of structure (III) or (IV); or one of $R_1$-$R_{12}$ joins with another one of $R_1$-$R_{12}$ to form a ring, and the remaining $R_1$-$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl or a bond to a compound of structure (III) or (IV), provided that all valencies are satisfied;

the chalcanoid is a compound of structure (V):

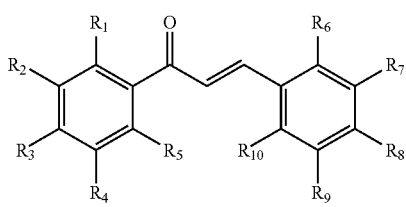

or a pharmaceutically or nutraceutically acceptable salt, tautomer, glycoside, prodrug or stereoisomer thereof, wherein $R_1$-$R_{10}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, or aralkylcarbonyl, provided that all valencies are satisfied; and the one or more stilbenes are compounds having a structure of Formula (I) or (II):

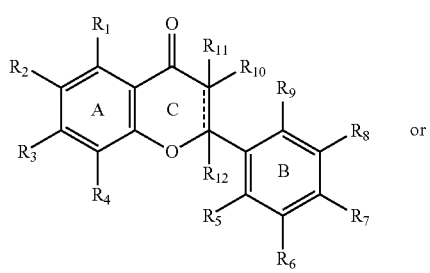

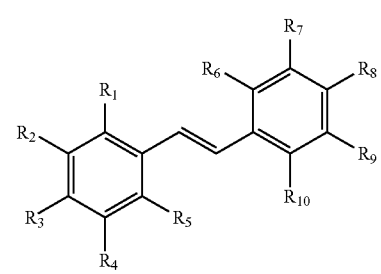

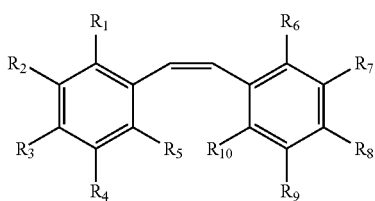

wherein $R_1$-$R_{10}$ are each independently a H, hydroxyl, glycoside, prenyl, flavonoid, chalcone, halogen, sulfhydryl, amino, aldehyde, $C_{1-12}$ alkyl, $C_{1-12}$ alkenyl, $C_{1-12}$ alkoxy, $C_{1-12}$ alkthio, $C_{1-12}$ alkyamino, aryl, heteroaryl, aralkyl, alkylcarbonyl, or aralkylcarbonyl; and wherein the flavans are compounds having a structure of Formula (VI):

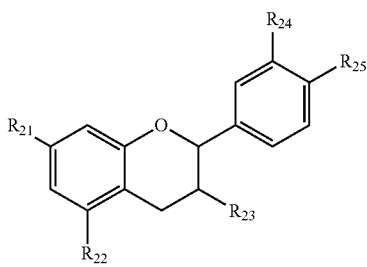

wherein $R_{21}$, $R_{22}$, $R_{23}$, $R_{24}$ and $R_{25}$ are independently selected from a H, —OH, —SH, —OCH$_3$, —SCH$_3$, —OR, —SR, —NH$_2$, —NRH, —NR$_2$, —NR$_3^+$X$^-$, esters of substitution groups, independently selected from the group consisting of gallate, acetate, cinnamoyl and hydroxylcinnamoyl esters, trihydroxybenzoyl esters and caffeoyl esters; a carbon, oxygen, nitrogen or sulfur glycoside of a single or a combination of multiple sugars including aldopentose, methyl aldopentose, aldohexose, ketohexose; dimer, trimer or other polymerized flavans;

wherein R is a $C_{1-10}$ alkyl group; and

X is a pharmaceutically acceptable counter anion of hydroxyl, chloride, iodide, sulfate, phosphate, acetate, fluoride, or carbonate.

In any of the aforementioned compositions, a *Morus* extract is from *Morus alba*, and an *Acacia* extract is from *Acacia catechu*. In further embodiments of these compositions, a major active ingredient in a *Morus* extract is Albanin G, Kuwanon G, Morusin, oxyresveratrol, mulberroside A or any combination thereof, and a major active ingredient in an *Acacia* extract is catechin, epicatechin, or both.

In further embodiments, any of the aforementioned compostions comprise one or more prenylayted flavonoids are compounds having a structure of Formula (III), (IV) or (V), wherein the optional double bond is present in ring C, $R_{11}$ and $R_{12}$ are absent, and $R_{10}$ is a prenyl group. In still further embodiments, any of the aforementioned compostions comprise one or more prenylayted flavonoids are compounds having a structure of Formula (III), (IV) or (V), wherein the at least one of $R_1$-$R_9$ is a prenyl group and $R_{10}$-$R_{12}$ are independently H or hydroxyl. In certain embodiments, any of the aforementioned compostions comprise one or more stilbenes having a structure of Formula (I) or (II), wherein $R_1$-$R_{10}$ are each independently a H, hydroxyl, glycoside, or $C_{1-4}$ alkoxy. In certain other embodiments, any of the aforementioned compostions comprise one or more stilbenes are compounds having a structure of Formula (I) or (II), wherein $R_1$-$R_{10}$ are each independently a H, hydroxyl, glycoside, or $C_{1-4}$ alkoxy. In further embodiments, any of the aforementioned compostions comprise one or more stilbenes are compounds having a structure of Formula (I) or (II), wherein $R_1$, $R_5$, $R_6$ and $R_{10}$ are H. In still further embodiments, any of the aforementioned compositions comprise one or more stilbenes are compounds having a structure of Formula (I) or (II), wherein $R_2$ is a glucoside, or $R_2$ and $R_8$ are glycosides, and one or more of $R_4$, $R_9$, and $R_{10}$ are hydroxyl. In yet further embodiments, any of the aforementioned compostions comprise one or more stilbenes are compounds having a structure of Formula (I) or (II), wherein $R_1$, $R_5$, and $R_6$ are H, and one or more of $R_2$-$R_4$ and $R_7$-$R_{10}$ are independently hydroxyl, $C_{1-3}$ alkoxy, or any combination thereof. In certain specific embodiments, a stilbene compound includes oxyresveratrol, resveratrol, piceatannol, pinosylvin, 3,4'-dihydroxystilbene, combretastatin A-1, pterostilbene, rhapontigenin, and a stilbene glycoside includes mulberroside A, rhaponticin, piceid, astringin, or any combination of these stilbenes or stilbene glycosides.

Any of the aforementioned *Morus* extract mixed with *Acacia* extract compositions are useful for promoting, managing or improving joint health, or for treating a joint disorder or disease (e.g., osteoarthritis, rheumatoid arthritis, juvenile rheumatoid arthritis, Still's disease, psoriatic arthritis, reactive arthritis, septic arthritis, Reiter's syndrome, Behcet's syndrome, Felty's syndrome, systemic lupus erythematosus, ankylosing spondylitis, diffuse idiopathic skeletal hyperostosis (DISH), sacroiliac joint dysfunction, polymyalgia rheumatic, carpal tunnel syndrome, gout, bursitis, tendenitis, synovitis, SAPHO (synovitis, acne, pustulosis, hyperostosis, osteitis) syndrome, patella chondromalacia, repetitive strain injury, sprain, dislocation).

In certain aspects, a composition of this disclosure comprises a mixture of a *Morus* extract enriched for one or more prenylated flavonoids and one or more stilbenes, and an *Acacia* extract enriched for flavans, wherein the composition inhibits cartilage degradation. Cartialge degradation is measured as the level of sulphated GAGs (e.g., released from proteoglycans) released into a medium at the end of a GAG release assay reaction, which reflects the amount of articular cartilage degradation "Inhibition of cartilage degradation" is established when there is a statistically significant reduction in sulphated GAG release as measured in, for example, a Blyscan™ assay (Accurate Chemical and Scientific Corp., Westbury, N.Y.) and described herein in Example 27.

In certain embodiments, a composition of this disclosure comprises an *Uncaria* extract containing or enriched for one or more flavans as described herein or in U.S. Pat. No. 8,034,387, and a *Morus* extract containing or enriched for at least one Diels-Alder adduct of a chalcone and a prenylphenyl moiety, prenylated flavonoid, stilbene, or any combination thereof. In certain embodiments, a composition comprises an *Uncaria* extract containing or enriched for one or more flavans as described herein or in U.S. Pat. No. 8,034, 387 and a *Morus* extract containing or enriched for one or more compounds listed in Table A and Examples 3, 5, 6 and 68. In still further embodiments, a composition comprises an *Acacia* extract containing or enriched for catechin, epicatichin, or both, and a *Morus* extract containing or enriched for one or more prenylated flavonoids, one or more stilbenes, or any combination thereof. In other embodiments, a composition comprises a mixture of a *Morus* extract enriched for prenylated flavonoids, and an *Uncaria* extract enriched for flavans.

In further embodiments, a composition of this disclosure comprises a mixture of a *Morus* extract enriched for one or more prenylated flavonoids and one or more stilbenes, and an *Uncaria* extract enriched for one or more flavans, wherein the one or more prenylated flavonoids are compounds having a structure of Formula (III) or (IV):

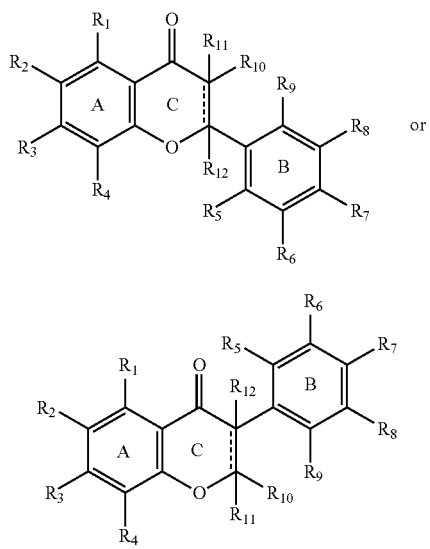

or a pharmaceutically or nutraceutically acceptable salt, tautomer, glycoside, prodrug or stereoisomer thereof, wherein $R_1$-$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkyl carbonyl, aralkylcarbonyl or a bond to a compound of structure (III) or (IV); or one of $R_1$-$R_{12}$ joins with another one of $R_1$-$R_{12}$ to form a ring, and the remaining $R_1$-$R_{12}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkylcarbonyl, aralkylcarbonyl or a bond to a compound of structure (III) or (IV), provided that all valencies are satisfied;

the chalcanoid is a compound of structure (V):

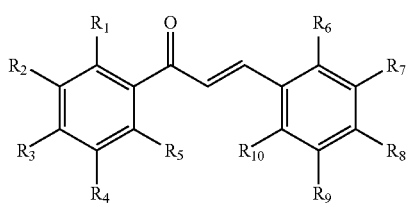

or a pharmaceutically or nutraceutically acceptable salt, tautomer, glycoside, prodrug or stereoisomer thereof, wherein $R_1$-$R_{10}$ are each independently H, hydroxyl, a prenyl group, flavonoid, chalcone, glycoside, halogen, sulfhydryl, amino, aldehyde, $C_{1-12}$ alkyl, $C_{1-12}$ alkoxy, $C_{1-12}$ alkthio, $C_{1-12}$ alkyamino, cycloalkyl, heterocyclyl, aryl, heteroaryl, aralkyl, alkyl carbonyl, or aralkylcarbonyl, provided that all valencies are satisfied; and the one or more stilbenes are compounds having a structure of Formula (I) or (II):

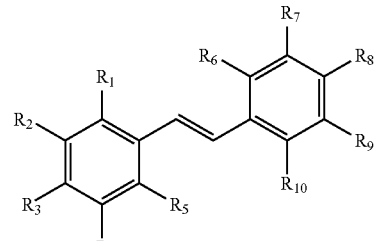

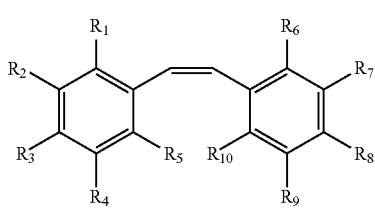

wherein $R_1$-$R_{10}$ are each independently a H, hydroxyl, glycoside, prenyl, flavonoid, chalcone, halogen, sulfhydryl, amino, aldehyde, $C_{1-12}$ alkyl, $C_{1-12}$ alkenyl, $C_{1-12}$ alkoxy, $C_{1-12}$ alkthio, $C_{1-12}$ alkyamino, aryl, heteroaryl, aralkyl, alkylcarbonyl, or aralkylcarbonyl; and wherein the flavans are compounds having a structure of Formula (VI):

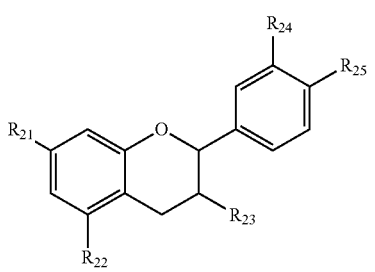

wherein $R_{21}$, $R_{22}$, $R_{23}$, $R_{24}$ and $R_{25}$ are independently selected from a H, —OH, —SH, —OCH$_3$, —SCH$_3$, —OR, —SR, —NH$_2$, —NRH, —NR$_2$, —NR$_3^+$X$^-$, esters of substitution groups, independently selected from the group consisting of gallate, acetate, cinnamoyl and hydroxylcinnamoyl esters, trihydroxybenzoyl esters and caffeoyl esters; a carbon, oxygen, nitrogen or sulfur glycoside of a single or a combination of multiple sugars including aldopentose, methyl aldopentose, aldohexose, ketohexose; dimer, trimer or other polymerized flavans;

wherein R is a $C_{1-10}$ alkyl group; and

X is a pharmaceutically acceptable counter anion of hydroxyl, chloride, iodide, sulfate, phosphate, acetate, fluoride, or carbonate.

In any of the aforementioned compositions, the *Morus* extract is from *Morus alba*, and the *Uncaria* extract is from *Uncaria gambir*. In further embodiments, a major active ingredient in the *Morus* extract is Albanin G, Kuwanon G, Morusin, oxyresveratrol, mulberroside A or any combination thereof, and a major active ingredient in the *Uncaria* extract is catechin, epicatechin, or a combination thereof.

In further embodiments, the one or more prenylayted flavonoids are compounds having a structure of Formula (III), (IV) or (V), wherein the optional double bond is present in ring C, $R_{11}$ and $R_{12}$ are absent, and $R_{10}$ is a prenyl group. In still further embodiments, the one or more prenylayted flavonoids are compounds having a structure of Formula (III), (IV) or (V), wherein the at least one of $R_1$-$R_9$ is a prenyl group and $R_{10}$-$R_{12}$ are independently H or hydroxyl. In certain specific embodiments, the prenylated flavonoids include Albanin G, Kuwanon G, Morusin, morusinol, Sanggenon, isoxanthoumol, glabridin, cathayanon A, or any combination thereof. In certain embodiments, the one or more stilbenes are compounds having a structure of Formula (I) or (II), wherein $R_1$-$R_{10}$ are each independently a H, hydroxyl, glycoside, or $C_{1-4}$ alkoxy. In further embodiments, the one or more stilbenes are compounds having a structure of Formula (I) or (II), wherein $R_1$, $R_5$, $R_6$ and $R_{10}$ are H. In still further embodiments, the one or more stilbenes are compounds having a structure of Formula (I) or (II), wherein $R_2$ is a glucoside, or $R_2$ and $R_8$ are glycosides, and one or more of $R_4$, $R_9$, and $R_{10}$ are hydroxyl. In yet further embodiments, the one or more stilbenes are compounds having a structure of Formula (I) or (II), wherein $R_1$, $R_5$, and $R_6$ are H, and one or more of $R_2$-$R_4$ and $R_7$-$R_{10}$ are independently hydroxyl, $C_{1-3}$ alkoxy, or any combination thereof. In certain specific embodiments, a stilbene compound includes oxyresveratrol, resveratrol, piceatannol, pinosylvin, 3,4'-dihydroxystilbene, combretastatin A-1, pterostilbene, rhapontigenin, and a stilbene glycoside includes mulberroside A, rhaponticin, piceid, astringin, or any combination of these stilbenes or stilbene glycosides.

In some embodiments, the flavonoid is a compound of structure (III) and in other embodiments the flavonoid is a compound of structure (IV). In some other embodiments, at least one of $R_1$-$R_{12}$, such as $R_{10}$ is prenyl. In other embodiments, polyflavonoids are provided and at least one of $R_1$-$R_{12}$ in the compounds of structure (III) or (IV) is a bond to a compounds of structure of (III) or (IV) (i.e., the compound comprises more than one flavonoid of structure (III) and/or (IV)).

In some other embodiments of the compounds of structure (III) or (IV), $R_1$-$R_{12}$ is H, hydroxyl, a prenyl group or cycloalkyl. For example, in some embodiments the cycloalkyl is substituted and/or comprises one or more carbon-carbon double bonds (i.e., is unsaturated). The optional substitutents are typically selected from aryl, such as phenyl, and aryl carbonyl. Accordingly, in some further embodiments, the flavonoid has one of the following structures (IIIa) or (IVa):

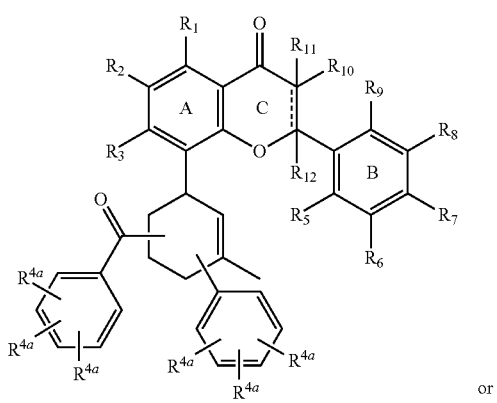

IIIa

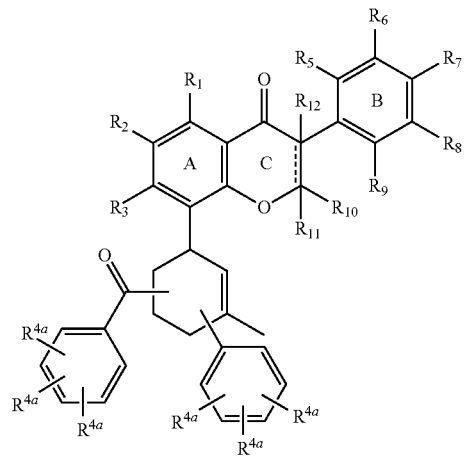

IVa wherein $R^{4a}$ is, at each occurrence, independently H, hydroxyl or a prenyl group.

In certain embodiments of the compounds of structure (IIIa) or (IVa), $R_1$-$R_3$ and $R_5$-$R_{12}$ are each independently selected from H, hydroxyl and a prenyl group. In certain embodiments, at least one of $R_1$-$R_3$, $R_{4a}$ or $R_5$-$R_{12}$ is prenyl, for example in some embodiments, $R_{10}$ is prenyl. In other embodiments of the compounds of structure (IIIa) or (IVa), at least two of $R_1$-$R_3$, $R_{4a}$ or $R_5$-$R_{12}$ is hydroxyl.

In some more specific embodiments, the flavonoid has one of the following structures:

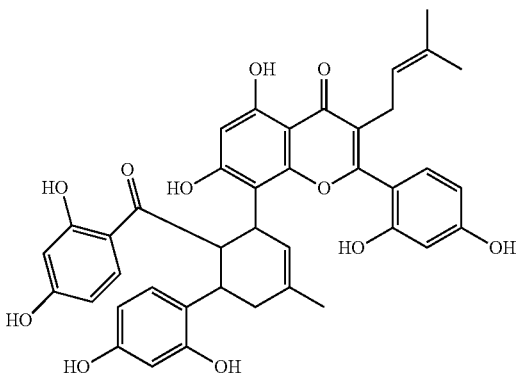

or

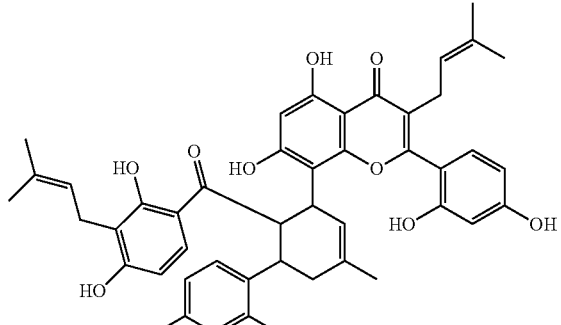

In other embodiments, one of $R_1$-$R_{12}$ joins with another one of $R_1$-$R_{12}$ to form a ring and the remaining $R_1$-$R_{12}$ are H, hydroxyl or a prenyl group. In certain of these embodiments, the ring is a heterocyclic ring, for example a cyclic ether ring. Accordingly, in certain embodiments the flavonoid has one of the following structures (IIIb) or (IVb):

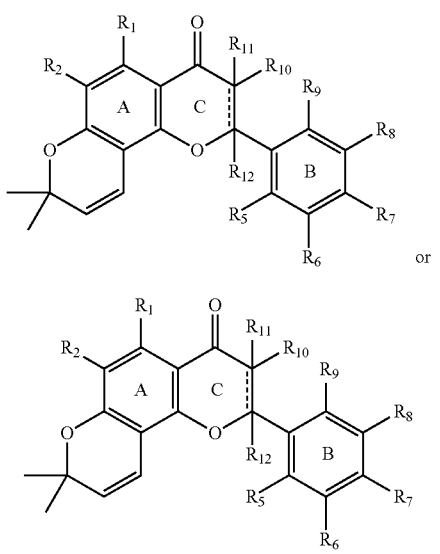

In certain embodiments of the compounds of structure (IIIb) or (IVb), $R_1$, $R_2$ and $R_5$-$R_{12}$ are each independently selected from H, hydroxyl and a prenyl group. In certain embodiments, at least one of $R_1$, $R_2$ or $R_5$-$R_{12}$ is prenyl, for example in some embodiments, $R_{10}$ is prenyl. In other embodiments of the compounds of structure (IIIb) or (IVb), at least two of $R_1$, $R_2$ or $R_5$-$R_{12}$ is hydroxyl. In certain embodiments, the flavonoid has the following structure:

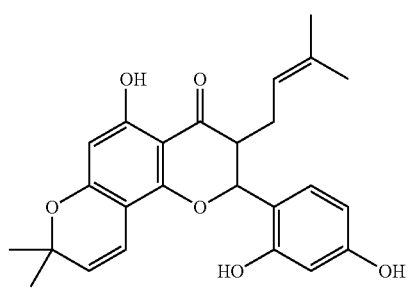 [SMILES: CC(C)=CCC1C(=O)c2c(O)cc3c(c2OC1c1ccc(O)cc1O)C=CC(C)(C)O3]

In various other embodiments, $R_1$-$R_{10}$ of the chalcanoid of structure (V) are each independently selected from H, hydroxyl, a prenyl group, and $C_{1-12}$ alkoxy.

Any of the aforementioned *Morus* extract mixed with *Uncaria* extract compositions are useful for promoting, managing or improving joint health, or for treating a joint disorder or disease (e.g., osteoarthritis, rheumatoid arthritis, juvenile rheumatoid arthritis, Still's disease, psoriatic arthritis, reactive arthritis, septic arthritis, Reiter's syndrome, Behcet's syndrome, Felty's syndrome, systemic lupus erythematosus, ankylosing spondylitis, diffuse idiopathic skeletal hyperostosis (DISH), sacroiliac joint dysfunction, polymyalgia rheumatic, carpal tunnel syndrome, gout, bursitis, tendenitis, synovitis, SAPHO (synovitis, acne, pustulosis, hyperostosis, osteitis) syndrome, patella chondromalacia, repetitive strain injury, sprain, dislocation). In certain embodiments, a composition of this disclosure comprises a mixture of a *Morus* extract enriched for one or more prenylated flavonoids and one or more stilbenes, and an *Uncaria* extract enriched for flavans, wherein the composition inhibits cartilage degradation.

In certain embodiments, a composition comprises a mixture of a *Morus* extract enriched for prenylated flavonoids, an *Uncaria* extract enriched for flavans, and an *Acacia* extract enriched for flavans. In further embodiments, a composition comprises a mixture of a *Morus* extract enriched for one or more prenylated flavonoids and one or more stilbenes, an *Uncaria* extract enriched for flavans including catechin, epicatechin or both, and an *Acacia* extract enriched for flavans including catechin, epicatechin or both. In certain embodiments, the *Morus* extract is from *Morus alba*, the *Uncaria* extract is from *Uncaria gambir*, and the *Acacia* extract is from *Acacia catechu*. In further embodiments, a major active ingredient in the *Morus* extract is Albanin G, Kuwanon G, Morusin, oxyresveratrol, mulberroside A or any combination thereof, and a major active ingredient in the *Uncaria* and *Acacia* extracts is catechin, epicatechin, or a combination thereof. Any of these three extract compositions (*Morus, Uncaria, Acacia*) are useful for promoting, managing or improving joint health, or for treating a joint disorder or disease (e.g., osteoarthritis, rheumatoid arthritis, juvenile rheumatoid arthritis, Still's disease, psoriatic arthritis, reactive arthritis, septic arthritis, Reiter's syndrome, Behcet's syndrome, Felty's syndrome, systemic lupus erythematosus, ankylosing spondylitis, diffuse idiopathic skeletal hyperostosis (DISH), sacroiliac joint dysfunction, polymyalgia rheumatic, carpal tunnel syndrome, gout, bursitis, tendenitis, synovitis, SAPHO (synovitis, acne, pustulosis, hyperostosis, osteitis) syndrome, patella chondromalacia, repetitive strain injury, sprain, dislocation).

In certain embodiments, a composition of this disclosure comprises a mixture of a *Morus* extract containing or enriched for at least one Diels-Alder adduct of a chalcone and a prenylphenyl moiety, prenylated flavonoid, stilbene or any combination thereof, and a *Curcuma* extract enriched for curcuminoids. In further embodiments, a composition comprises a mixture of a *Morus* extract containing or enriched for one or more compounds listed in Table A and Examples 3, 5, 6 and 68, and a *Curcuma* extract enriched for one or more curcuminoids. In still further embodiments, a composition comprises a *Morus* extract containing or enriched for one or more prenylated flavonoids, one or more stilbenes or any combination thereof, and a *Curcuma* extract enriched for one or more curcuminoids. In certain embodiments, the *Morus* extract is from *Morus alba*, and the *Curcuma* extract is from *Curcuma longa*. In any of the aforementioned compositions, a major active ingredient in the *Morus* extract is Albanin G, Kuwanon G, Morusin, oxyresveratrol, mulberroside A or any combination thereof, and a major active ingredient in the *Curcuma* extract is curcumin, demethoxy-curcumin, bisdemethoxy-curcumin or any combination thereof.

Any of the aforementioned *Morus* extract mixed with *Curcuma* extract compositions are useful for promoting, managing or improving joint health, or for treating a joint disorder or disease (e.g., osteoarthritis, rheumatoid arthritis, juvenile rheumatoid arthritis, Still's disease, psoriatic arthritis, reactive arthritis, septic arthritis, Reiter's syndrome, Behcet's syndrome, Felty's syndrome, systemic lupus erythematosus, ankylosing spondylitis, diffuse idiopathic skeletal hyperostosis (DISH), sacroiliac joint dysfunction, polymyalgia rheumatic, carpal tunnel syndrome, gout, bursitis, tendenitis, synovitis, SAPHO (synovitis, acne, pustulosis, hyperostosis, osteitis) syndrome, patella chondromalacia, repetitive strain injury, sprain, dislocation). In certain embodiments, a composition of this disclosure comprises a mixture of a *Morus* extract enriched for one or more prenylated flavonoids and one or more stilbenes, and an *Curcuma* extract enriched for one or more curcuminoids, wherein the composition inhibits cartilage degradation.

In certain embodiments, a composition comprises a mixture of a *Morus* extract enriched for prenylated flavonoids, an *Acacia* extract enriched for flavans, and a *Curcuma* extract enriched for curcuminoids. In further embodiments, a composition comprises a mixture of a *Morus* extract enriched for one or more prenylated flavonoids and one or more stilbenes, an *Acacia* extract enriched for flavans including catechin, epicatechin or both, and a *Curcuma* extract enriched for one or more curcuminoids. In certain embodiments, the *Morus* extract is from *Morus alba*, the *Acacia* extract is from *Acacia catechu*, and the *Curcuma* extract is from *Curcuma longa*. In further embodiments, a major active ingredient in the *Morus* extract is Albanin G, Kuwanon G, Morusin, oxyresveratrol, mulberroside A or any combination thereof, and a major active ingredient in the *Curcuma* extract is curcumin (diferuloylmethane), demethoxy-curcumin, bisdemethoxy-curcumin or any combination thereof.

In certain embodiments, a composition comprises a mixture of a *Morus* extract enriched for prenylated flavonoids, an *Uncaria* extract enriched for flavans, and a *Curcuma* extract enriched for curcuminoids. In further embodiments, a composition comprises a mixture of a *Morus* extract enriched for one or more prenylated flavonoids and one or more stilbenes, an *Uncaria* extract enriched for flavans including catechin, epicatechin or both, and a *Curcuma* extract enriched for one or more curcuminoids. In certain embodiments, the *Morus* extract is from *Morus alba*, the *Uncaria* extract is from *Uncaria gambir*, and the *Curcuma* extract is from *Curcuma longa*.

Any of these three extract compositions (*Morus, Morus, Acacia, Curcuma* or *Morus, Uncaria, Curcuma*) are useful for promoting, managing or improving joint health, or for treating a joint disorder or disease (e.g., osteoarthritis, rheumatoid arthritis, juvenile rheumatoid arthritis, Still's disease, psoriatic arthritis, reactive arthritis, septic arthritis, Reiter's syndrome, Behcet's syndrome, Felty's syndrome, systemic lupus erythematosus, ankylosing spondylitis, diffuse idiopathic skeletal hyperostosis (DISH), sacroiliac joint dysfunction, polymyalgia rheumatic, carpal tunnel syndrome, gout, bursitis, tendenitis, synovitis, SAPHO (synovitis, acne, pustulosis, hyperostosis, osteitis) syndrome, patella chondromalacia, repetitive strain injury, sprain, dislocation).

In any of the aforementioned compositions, a *Morus* extract is enriched for prenylated flavonoids, such as Albanin G, Kuwanon G, Morusin, or any combination thereof. In certain embodiments, a *Morus* extract is enriched for stilbenes, such as oxyresveratrol, mulberroside A, or any combination thereof. In further embodiments, a *Morus* extract is enriched for prenylated flavonoids and stilbenes, including Albanin G, Kuwanon G, Morusin, oxyresveratrol, mulberroside A, or any combination thereof. In still further embodiments, a *Morus* extract is enriched for prenylated flavonoids and stilbenes, wherein the extract comprises from about 2% to about 25% prenylated flavonoids and from about 1% to about 8% stilbenes, or wherein the extract comprises at least 3% prenylated flavonoids and at least 3% stilbenes (weight to weight). In other embodiments, prenylated flavonoids, stilbenes, or both are isolated or purified from a *Morus* extract and used in the compositions of this disclosure. Exemplary active ingredients that can be isolated or purified from a *Morus* extract and used in the compositions of this disclosure include Albanin G, Kuwanon G, Morusin, oxyresveratrol, mulberroside A, or any combination thereof. In any of the aforementioned compositions, the *Morus* extract is from *Morus alba*.

In any of the aforementioned embodiments, the compositions comprising mixtures of extracts or compounds may be mixed at a particular ratio by weight. For example, a *Morus* extract and an *Acacia* extract may be blended in a 2:1 weight ratio, respectively. In certain embodiments, the ratio (by weight) of two extracts or compounds of this disclosure ranges from about 0.5:5 to about 5:0.5. Similar ranges apply when more than two extracts or compounds (e.g., three, four, five) are used. Exemplary ratios include 0.5:1, 0.5:2, 0.5:3, 0.5:4, 0.5:5, 1:1, 1:2, 1:3, 1:4, 1:5, 2:1, 2:2, 2:3, 2:4, 2:5, 3:1, 3:2, 3:3, 3:4, 3:5, 4:1, 4:2, 4:3, 4:4, 4:5, 5:1, 5:2, 5:3, 5:4, 5:5, 1:0.5, 2:0.5, 3:0.5, 4:0.5, or 5:0.5. In certain embodiments, *Morus* and *Acacia* extracts are blended in a 1:1, 2:1, 3:1, 4:1, 5:1, 1:2, 1:3, 1:4, or 1:5 weight ratio, respectively. In further embodiments, *Morus* and *Acacia* extracts are blended in a range of 1:2 to 4:1 weight ratio, respectively. In certain embodiments, *Morus* and *Uncaria* extracts are blended in a 1:1, 2:1, 3:1, 4:1, 5:1, 1:2, 1:3, 1:4, or 1:5 weight ratio, respectively. In further embodiments, *Morus* and *Uncaria* extracts are blended in a range of 1:4 to 4:1 weight ratio, respectively. In certain embodiments, *Morus* and *Curcuma* extracts are blended in a 1:1, 2:1, 3:1, 4:1, 5:1, 1:2, 1:3, 1:4, or 1:5 weight ratio, respectively. In further embodiments, *Morus* and *Curcuma* extracts are blended in a range of 1:1 to 4:1 weight ratio, respectively.

In any of the aforementioned embodiments, the compositions comprising mixtures of extracts or compounds may be present at certain percentage levels or ratios. In certain embodiments, a composition comprising a *Morus* extract can include 0.1% to 49.9% or about 1% to about 10% or about 0.5% to about 3% of prenylated flavonoids, 0.1% to 49.9% or about 1% to about 10% or about 0.5% to about 3% of stilbenes, or a combination thereof. In certain embodiments, a composition comprising an *Acacia* extract can include from about 0.01% to about 99.9% flavans or include at least 1%, 2%, 3%, 4%, 5%, 6%, 7%, 8%, 9%, 10%, 11%, 12%, 13%, 14%, 15%, 16%, 17%, 18%, 19%, 20%, 30%, 35%, 40%, 45%, 50%, 55%, 60%, 65%, 70%, 75%, or 80% flavans (e.g., catechin, epicatechin, or both)

In certain examples, a composition of this disclosure may be formulated to further comprise a pharmaceutically or nutraceutically acceptable carrier, diluent, or excipient, wherein the pharmaceutical or nutraceutical formulation comprises from about 0.5 weight percent (wt %) to about 90 wt % of active or major active ingredients of an extract mixture. In further embodiments, the pharmaceutical or nutraceutical formulation comprises from about 0.5 weight percent (wt %) to about 90 wt %, about 0.5 wt % to about 80 wt %, about 0.5 wt % to about 75 wt %, about 0.5 wt % to about 70 wt %, about 0.5 wt % to about 50 wt %, about 1.0 wt % to about 40 wt %, about 1.0 wt % to about 20 wt %, about 1.0 wt % to about 10 wt %, about 3.0 wt % to about 9.0 wt %, about 5.0 wt % to about 10 wt %, about 3.0 wt % to about 6 wt % of the major active ingredients in an extract mixture, or the like. In any of the aforementioned formulations, a composition of this disclosure is formulated as a tablet, hard capsule, softgel capsule, powder, or granule.

In certain embodiments, a composition comprising a *Morus* extract with a pharmaceutically or nutraceutically acceptable carrier, diluent, or excipient will contain at least 6 wt % or at least 5 wt % or at least 3 wt % or at least 2 wt % or at least 1 wt % active *Morus* ingredients, such as prenylated flavonoids, stilbenes, or a combination thereof. For example, a pharmaceutical or nutraceutical composition comprising a *Morus* extract will include at least 3 wt % prenylated flavonoids or from about at least 0.5 wt % to about at least 2.5 wt % or from about at least 1 wt % to about at least 2.5 wt % or from about at least 1.5 wt % to about at least 2.5 wt % (e.g., Albanin G, Kuwanon G, Morusin, or any combination thereof) and at least 3% stilbenes (e.g., oxyresveratrol, mulberroside A, or both). In certain embodiments, a composition comprising an *Acacia* or *Uncaria* extract with a pharmaceutically or nutraceutically acceptable carrier, diluent, or excipient will contain at least 20 wt % active *Acacia* or *Uncaria* ingredients, such as flavans. For example, a pharmaceutical or nutraceutical composition comprising an *Acacia* or *Uncaria* extract will include at least about 3.5 wt % to about at least 14 wt % or at least about 6 wt % to about at least 16.5 wt % (e.g., catechin, epicatechin, or both). In certain embodiments, a composition comprising a *Curcuma* extract with a pharmaceutically or nutraceutically acceptable carrier, diluent, or excipient will contain at least 25 wt % active *Curcuma* ingredients, such as cucuminoids. For example, a pharmaceutical or nutraceutical composition comprising a *Curcuma* extract will include at least about 4.5 wt % to at least about 13 wt % curcuminoids (e.g., curcumin, demethoxy-curcumin, bisdemethoxy-curcumin, or any combination thereof). In any of the aforementioned formulations, a composition of this disclosure is formulated as a tablet, hard capsule, softgel capsule, powder, or granule.

In certain embodiments, a composition of this disclosure comprises *Morus* and *Acacia* extracts, wherein the composition comprises from about 1 wt % to about 2.5 wt % prenylated flavonoids including Albanin G, Kuwanon G and Morusin, from about 1 wt % to about 2.5 wt % stilbenes including oxyresveratrol and mulberroside A, and about 3.5 wt % to about 14 wt % flavans including catechin and epicatechin. In certain other embodiments, a composition of this disclosure comprises *Morus* and *Uncaria* extracts, wherein the composition comprises from about 0.5 wt % to about 2.5 wt % prenylated flavonoids including Albanin G, Kuwanon G and Morusin, from about 0.5 wt % to about 2.5 wt % stilbenes including oxyresveratrol and mulberroside A, and about 6 wt % to about 16.5 wt % flavans including catechin and epicatechin. In certain further embodiments, a composition of this disclosure comprises *Morus* and *Curcuma* extracts, wherein the composition comprises from about 1.5 wt % to about 2.5 wt % prenylated flavonoids including Albanin G, Kuwanon G and Morusin, from about 1.5 wt % to about 2.5 wt % stilbenes including oxyresveratrol and mulberroside A, and about 4.5 wt % to about 13 wt % curcuminoids including curcumin.

Any of these compositions may be used to promote joint health; improve joint health; maintain joint health; treat or manage joint health; support joint health; support a normal and comfortable range of motion and/or flexibility; improve range of motion and/or flexibility; reduce the action of harmful enzymes that break down protective joint tissues; alter the action of enzymes that affect joint health; improve joint movement and/or joint function; improve physical mobility; manage and/or maintain physical mobility; alleviate joint pain and/or joint stiffness; improve joint physical function; promote or enhance flexibility and comfortable movement; promote healthy joint function and joint comfort; relieve joint discomfort; relieve joint discomfort caused by exercise, work, overexertion or any combination thereof; promote healthy joints by protecting cartilage integrity; maintain joint cartilage; support joint cartilage; treat, prevent, or manage cartilage degradation; minimize cartilage degradation; promote joint health or comfort by maintaining synovial fluid for joint lubrication; support joint stability and joint flexibility; revitalize joints and promote mobility; promote flexible joints and strong cartilage; maintain steady blood flow to joints to support enhanced flexibility and/or strength; promote joint comfort and a wide range of motion after exercise, work, overexertion, or any combination thereof.

In other embodiments, any of these compositions may be used to treat osteoarthritis, rheumatoid arthritis, juvenile rheumatoid arthritis, Still's disease, psoriatic arthritis, reactive arthritis, septic arthritis, Reiter's syndrome, Behcet's syndrome, Felty's syndrome, systemic lupus erythematosus, ankylosing spondylitis, diffuse idiopathic skeletal hyperostosis (DISH), sacroiliac joint dysfunction, polymyalgia rheumatic, carpal tunnel syndrome, gout, bursitis, tendenitis, synovitis, SAPHO (synovitis, acne, pustulosis, hyperostosis, osteitis) syndrome, patella chondromalacia, repetitive strain injury, sprain, dislocation, or any other associated indication, and generally with acceptable toxicity to a patient.

In other embodiments of the present disclosure, a composition can also include an adjuvant or a carrier. Adjuvants include substances that generally enhance the function of the formula in promoting, maintaining, or improving joint health. Suitable adjuvants include Freund's adjuvant; other bacterial cell wall components; aluminum-based salts; calcium-based salts; silica; boron, histidine, glucosamine sulfates, Chondroitin sulfate, copper gluconate, polynucleotides; vitamin D, vitamin K, toxoids; shark and bovine cartilage; serum proteins; viral coat proteins; other bacterial-derived preparations; γ-interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers include compounds that increase the half-life of a therapeutic or neutraceutical composition in a treated subject. Suitable carriers include polymeric controlled release formulations, biodegradable implants, liposomes, bacteria, viruses, oils, esters, or glycols.

Additional adjunctive agents useful with the compositions of this disclosure include glucosamine (including glucosamine sulfate, glucosamine hydrochloride, N-acetylglucosamine), glycosaminoglycans (GAGs), hyaluronic acid (HA), elastin, collagen, chicken collagen Type II, hyaluronic acid and collagen blend, chondroitin sulfate, methylsulfonylmethane (MSM), bovine cartilage, amino acids (including desmosine, isodesmosine, L-glutamine), *Boswellia serrata* extract, piperine (e.g., *Piper nigrum* L (black pepper) extract or *Piper longum* L (long pepper) extract), bromelain (pineapple extract), trypsin, rutin, emu oil, transforming growth factor(TGF)-β, carotenoids (such as lutein, carotene, canthaxanthin); vitamins (such as Vitamin D3), ω-3 fatty acids (such as eicosapentaenoic acid, EPA; docosahexaenoic acid, DHA), calcium fructoborate, eggshell membrane, astaxanthin, *Hydrilla verticillata* extract (leaf and bud), ginger extract (root), grapefruit extract (seed), non-steroidal anti-inflammatory drugs (NSAIDs), or any combination thereof.

Exemplary NSAIDS include salicylates, such as aspirin (acetylsalicylic acid), diflusinal, salsalate; propionic acid derivatives, such as ibuprofen, dexibuprofen, naproxen, fenoprofen, ketoprofen, dexketoprofen, flurbiprofen, oxprozin, loxoprofen; acetic acid derivatives, such as indometacin, tolmetin, sulindac, etodolac, ketorolac, diclofenac, nabumetone; enolic acid derivatives, such as piroxicam, meloxicam, tenoxicam, droxicam, lornoxicam, isoxicam; fenamic acid derivatives, such as mefenamic acid, meclofenamic acid, flufenamic acid, tolfenamic acid; selective COX-2 inhibitors, such s celecoxib, parecoxib, lumiracoxib, etoricoxib, firocoxib, paracetamol, H-harpagide; suphonanilides, such as nimesulide; nicotinic acid derivatives, such as lysine clonixinate; dual COX/LX inhibitors, such as licofelone. A related drug, paracetamol or "acetaminophen" is often considered in the same category as NSAIDS due to its use as a non-narcotic analgesic and fever-reducing agent, but is not classified as a NSAID because it only exerts weak anti-inflammatory.

In certain embodiments, compositions of the instant disclosure further comprise an injectable anticoagulant, an oral anticoagulant, an antiplatelet agent, an anti-angina agent, or a COX-2 selective inhibitor. Examplary injectable anticoagulants include heparin, dalteparin, enoxaparin and tinzaparin. Examples of oral anticoagulants include, but are not limited to warfarin, vitamin K antagonists and vitamin K reductase inhibitors. Examples of antiplatelet agents include aspirin, clodipogrel and dipyridamole. Examplary anti-angina drugs include nitrates, beta-blockers, calcium blockers, angiotensin-converting enzyme inhibitors, and potassium channel activators. Finally, examples of COX-2 selective inhibitors include rofecoxib, celecoxib, etodolac and meloxicam.

In certain embodiments, a composition comprises a mixture of a *Morus* extract enriched for one or more prenylated flavonoids and one or more stilbenes, an *Acacia* extract enriched for flavans, and a glucosamine-type compound. In further embodiments, the *Morus* extract is a *Morus alba* extract, the *Acacia* extract is an *Acacia catechu* extract, and the glucosamine-type compound is glucosamine sulfate, glucosamine hydrochloride, N-acetylglucosamine, chondroitin sulfate, methylsulfonylmethane, or hyaluronic acid. In certain embodiments, *Morus* extract, *Acacia* extract, and NAG are blended in a 1:1:1, 2:1:1, 3:1:1, 4:1:1, 5:1:1, 1:2:1, 1:3:1, 1:4:1, 1:5:1, 1:1:2, 1:1:3, 1:1:4, or 1:1:5 weight ratio, respectively. In certain embodiments, *Morus* extract, *Uncaria* extract, and NAG are blended in a 1:1:1, 2:1:1, 3:1:1, 4:1:1, 5:1:1, 1:2:1, 1:3:1, 1:4:1, 1:5:1, 1:1:2, 1:1:3, 1:1:4, or 1:1:5 weight ratio, respectively. In certain embodiments, *Morus* extract, *Curcuma* extract, and NAG are blended in a 1:1:1, 2:1:1, 3:1:1, 4:1:1, 5:1:1, 1:2:1, 1:3:1, 1:4:1, 1:5:1, 1:1:2, 1:1:3, 1:1:4, or 1:1:5 weight ratio, respectively. In certain embodiments, a composition comprises a mixture of a *Morus* extract enriched for prenylated flavonoids, an *Uncaria* extract enriched for flavans, and a glucosamine-type compound. In further embodiments, the *Morus* extract is a *Morus alba* extract, the *Uncaria* extract is an *Uncaria gambir* extract, and the glucosamine-type compound is glucosamine sulfate, glucosamine hydrochloride, N-acetylglucosamine, chondroitin sulfate, methylsulfonylmethane, or hyaluronic acid.

In certain embodiments, a composition comprises a mixture of a *Morus* extract enriched for prenylated flavonoids, a *Curcuma* extract enriched for curcuminoids, and a glucosamine-type compound. In further embodiments, the *Morus* extract is a *Morus alba* extract, the *Curcuma* extract is a *Curcuma longa* extract, and the glucosamine-type compound is glucosamine sulfate, glucosamine hydrochloride, N-acetylglucosamine, chondroitin sulfate, methylsulfonylmethane, or hyaluronic acid.

In any of the aforementioned compositions, the compositions may additionally comprise *Mentha* extract enriched for rosmarinic acid, eriocitrin, or both. Rosmarinic acid accumulation is found most notably in many plants of the Lamiaceae family (dicotyledons), especially in the subfamily Nepetoideae, inlcuding plants commonly used as culinary herbs, such as *Ocimum basilicum* (basil), *Ocimum tenuiflorumcum* (holy basil), *Melissa officinalis* (lemon balm), *Rosmarinus officinalis* (rosemary), *Origanum majorana* (marjoram), *Salvia officinalis* (sage), *Thymus vulgaris* (thyme) and *Mentha piperita* (peppermint). Rosmarinic acid is also found in plants with medicinal properties, such as common self-heal (*Prunella vulgaris*) or species in the genus *Stachy*. Other exemplary plants that contain rosmarinic acid include *Heliotropium foertherianum* (a plant in the family Boraginaceae), species in the genera *Maranta* (*Maranta leuconeura, Maranta depressa*, which are plants in the family Marantaceae, monocotyledons), species in the genera *Thalia* (*Thalia geniculata*), and *Anthoceros agrestis* (hornwort).

Exemplary mint plants containing rosmarinic acid or eriocitrin or both include *Mentha aquatica* (Water mint or Marsh mint); *Mentha arvensis* (Corn Mint, Wild Mint, Japanese Peppermint, Field Mint, Pudina, Banana mint); *Mentha asiatica* (Asian Mint); *Mentha australis* (Australian mint); *Mentha canadensis; Mentha cervina* (Hart's Pennyroyal); *Mentha citrata* (Bergamot mint, Orange mint); *Mentha crispata* (Wrinkled-leaf mint); *Mentha dahurica* (Dahurian Thyme); *Mentha diemenica* (Slender mint); *Mentha laxiflora* (Forest mint); *Mentha longifolia* (*Mentha sylvestris*, Horse Mint); *Mentha piperita* (Peppermint); *Mentha pulegium* (Pennyroyal); *Mentha requienii* (Corsican mint); *Mentha sachalinensis* (Garden mint); *Mentha satureioides* (Native Pennyroyal); *Mentha spicata* (*M. viridis*, syn *M. cordifolia* Spearmint, Curly mint); *Mentha suaveolens* (Apple mint, Pineapple mint (a variegated cultivar of Apple mint)); *Mentha vagans* (Gray mint).

In certain embodiments, a composition comprises a mixture of a *Morus* extract enriched for prenylated flavonoids, an *Acacia* extract enriched for flavans, and a *Mentha* extract enriched for rosmarinic acid, eriocitrin, or both. In further embodiments, the *Morus* extract is a *Morus alba* extract, the *Acacia* extract is an *Acacia catechu* extract, and the *Mentha* extract is a *Mentha piperita* extract. In certain embodiments, *Morus, Acacia* and *Mentha* extracts are blended in a 1:1:0.5, 2:1:0.5, 3:1:0.5, 4:1:0.5, 5:1:0.5, 1:2:0.5, 1:3:0.5, 1:4:0.5, 1:5:0.5, 1:1:1, 1:1:2, 1:1:3, 1:1:4, or 1:1:5 weight ratio, respectively.

In certain embodiments, a composition comprises a mixture of a *Morus* extract enriched for prenylated flavonoids, an *Uncaria* extract enriched for flavans, and a *Mentha* extract enriched for rosmarinic acid, eriocitrin, or both. In further embodiments, the *Morus* extract is a *Morus alba* extract, the *Uncaria* extract is an *Uncaria gambir* extract, and the *Mentha* extract is a *Mentha piperita* extract. In certain embodiments, *Morus, Uncaria* and *Mentha* extracts are blended in a 1:1:0.5, 2:1:0.5, 3:1:0.5, 4:1:0.5, 5:1:0.5, 1:2:0.5, 1:3:0.5, 1:4:0.5, 1:5:0.5, 1:1:1, 1:1:2, 1:1:3, 1:1:4, or 1:1:5 weight ratio, respectively.

In certain embodiments, a composition comprises a mixture of a *Morus* extract enriched for prenylated flavonoids, a *Curcuma* extract enriched for curcuminoids, and a *Mentha* extract enriched for rosmarinic acid, eriocitrin, or both. In further embodiments, the *Morus* extract is a *Morus alba* extract, the *Curcuma* extract is a *Curcuma longa* extract, and the *Mentha* extract is a *Mentha piperita* extract. In certain embodiments, *Morus, Curcuma* and *Mentha* extracts are blended in a 1:1:0.5, 2:1:0.5, 3:1:0.5, 4:1:0.5, 5:1:0.5, 1:2:0.5, 1:3:0.5, 1:4:0.5, 1:5:0.5, 1:1:1, 1:1:2, 1:1:3, 1:1:4, or 1:1:5 weight ratio, respectively.

Any of the aforementioned compositions are useful for promoting joint health; improving joint health; maintaining joint health; treating or managing joint health; supporting joint health; supporting a normal and comfortable range of motion and/or flexibility; improving range of motion and/or flexibility; reducing the action of harmful enzymes that break down protective joint tissues; altering the action of enzymes that affect joint health; improving joint movement and/or joint function; improving physical mobility; managing and/or maintaining physical mobility; alleviating joint pain and/or joint stiffness; improving joint physical function; promoting or enhancing flexibility and comfortable movement; promoting healthy joint function and joint comfort; relieving joint discomfort; relieving joint discomfort caused by oxidative stress, harmful free radicals, aging, wear and tear, exercise, work, overexertion or any combination thereof; managing or reducing joint damage caused by oxidative stress, harmful free radicals, aging, wear and tear, exercise, work, overexertion or any combination thereof; promoting healthy joints by protecting cartilage integrity; maintaining joint cartilage; supporting joint cartilage; treating, preventing, or managing cartilage degradation; minimizing cartilage degradation; promoting joint health or comfort by maintaining synovial fluid for joint lubrication; supporting joint stability and joint flexibility; revitalizing joints and promoting mobility; promoting flexible joints and strong cartilage; maintaining steady blood flow to joints to support enhanced flexibility and/or strength; promoting joint comfort and a wide range of motion after exercise, work, overexertion or any combination thereof; or any combination thereof.

In further embodiments, any of the aforementioned compositions are useful for treating, preventing, or ameliorating joint disorders or disease, such as osteoarthritis, rheumatoid arthritis, juvenile rheumatoid arthritis, Still's disease, psoriatic arthritis, reactive arthritis, septic arthritis, Reiter's syndrome, Behcet's syndrome, Felty's syndrome, systemic lupus erythematosus, ankylosing spondylitis, diffuse idiopathic skeletal hyperostosis (DISH), sacroiliac joint dysfunction, polymyalgia rheumatic, carpal tunnel syndrome, gout, bursitis, tendenitis, synovitis, SAPHO (synovitis, acne, pustulosis, hyperostosis, osteitis) syndrome, patella chondromalacia, repetitive strain injury, sprain, dislocation, or any combination thereof.

EXAMPLES

Example 1

Preparation of Organic and Aqueous Extracts from *Morus alba*

Plant material from *Morus alba* L. root barks was ground to a particle size of no larger than two millimeters (mm). Dried ground plant material (60 grams (g)) was then transferred to an Erlenmeyer flask and Methanol:Dichloromethane (1:1 volume ratio) (600 milliliters (mL)) was added. The mixture was shaken for one hour, filtered and the biomass was extracted again with Methanol:Dichloromethane (1:1 volume ratio) (600 mL). These organic extracts were combined and evaporated under vacuum to provide 3.55 g of organic extract (OE). After organic extraction, the biomass was air dried and extracted once with ultrapure water (600 mL). The aqueous solution was filtered and freeze-dried to provide 4.44 g of aqueous extract (AE).

Similar results were obtained using the same procedure or reflex in flasks, but with the organic solvent being replaced with methanol or ethanol to provide a methanol extract (ME) or ethanol extract (EE), respectively. Other species and parts of plants and marine sample were extracted using this same procedure.

Example 2

High Throughput Purification (HTP) of Active Plant Extracts

Organic extract material (400 mg) from the *Morus alba* root bark extract obtained in Example 1 was loaded onto a prepacked (2 cm ID×8.2 cm, 10 g silica gel) column. The column was then eluted using a Hitachi® High Throughput Purification (HTP) system with a gradient mobile phase of (A) 50:50 volume ratio of EtOAc:Hexane and (B) Methanol from 100% A to 100% B in 30 minutes at a flow rate of 5 mL/min. The separation was monitored using a broadband wavelength UV detector and the fractions were collected in a 96-deep-well plate at 1.9 mL/well using a Gilson fraction collector. The sample plate was dried under low vacuum and centrifugation and then the samples were dissolved with 1.5 mL dimethyl sulfoxide (DMSO) per well. A portion (100 µL) was taken and combined (based on UV trace) for the function assay. Column fractions having significant biological activity were retained for further testing.

Example 3

Isolation, Purification, and Identification of Prenylated Flavonoids from *Morus alba* Extracts An organic extract (11 g) from the root barks of *Morus alba*, obtained as described in Example 1, was divided and loaded separately onto two pre-packed flash columns (120 g silica, particle size 32-60 µm, 4 cm×19 cm), and then eluted with Hexane, EtOAc and Methanol (as the mobile phase) at a flow rate of 20 mL/minutes. The gradients started with 95% Hexane/EtOAC for 5 minutes, then increased EtOAC from 5% to 100% over the duration of 25 minutes, and then held at 100% EtOAc for additional five minutes, before increasing MeOH from 0% to 50% MeOH/EtOAC over a next period of 15 minutes, finally changed the elution solution to 100% MeOH and eluted the column for another 16 minutes. The total run time was 66 minutes and 88 fractions were generated for each column. The fractions were analyzed by silica gel thin layer chromatography (TLC) and pooled together to generate eight column eluent pools.

The resulting best active pool (containing 300 mg of material) was fractionated on a preparative C18 column (30 cm×250 cm) with a gradient mobile phase of water (A) and methanol (B) over 60 minutes at a flow rate of 20 mL/minute to generate 22 fraction pools. Mass Spectrometry (MS) analysis showed that these pooled fractions of material contain three related compounds, described in more detail below.

Compound 1 (28.2 mg) was identified as a Diels-Alder adduct of a chalcone and prenylphenyl moiety called Kuwanon G, also known as Moracenin B or Albanin F, by High Resolution Electron Spray Ionization Mass Spectroscopy (HRESIMS) (m/z) [M+H]$^-$=693.2329; UV $\lambda_{max}$ (MeOH): 265, 320 nm; $^1$H NMR (600 MHz, DMSO-d$_6$, 100° C.) δ ppm 1.44 (s, 3H) 1.52 (br. s., 3H) 1.58 (s, 3H) 1.92 (m, 2H) 3.08 (d, 3H) 3.56 (m, 2H) 4.29 (d, J=10.02 Hz, 1H) 4.48 (m, 1H) 5.07 (m, 1H) 5.14 (br. s, 1H) 5.93 (s, 2H) 5.96 (dd, J=8.35, 2.23 Hz, 1H) 6.02 (br s, 1H) 6.11 (d, J=2.23 Hz, 1H) 6.41 (dd, J=8.35, 2.23 Hz, 1H) 6.51 (s, 1H)

6.60 (m, 1H) 7.13 (d, J=8.35 Hz, 1H) 7.28 (br s, 1H); $^{13}$C NMR (126 MHz, METHANOL-d$_4$) δ ppm 16.35 (1C) 21.78 (1C) 23.35 (1C) 24.53 (1C) 37.72 (1C) 97.14 (1C) 101.57 (1C) 102.22 (1C) 102.33 (1C) 104.28 (1C) 106.55 (2C) 107.00 (1C) 107.21 (1C) 112.37 (1C) 114.47 (1C) 120.27 (1C) 121.62 (2C) 123.27 (1C) 131.05 (1C) 131.35 (2C) 132.62 (1C) 132.99 (1C) 155.16 (1C) 155.56 (1C) 156.38 (1C) 159.66 (1C) 160.39 (2C) 161.13 (1C) 161.88 (1C) 164.51 (1C) 164.63 (1C) 182.46 (1C) 208.68 (1C).

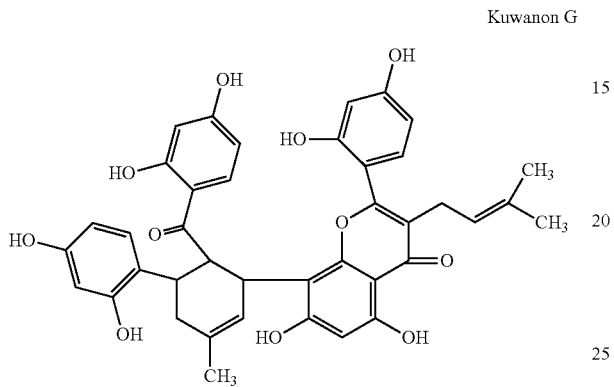

Kuwanon G

Compound 2 (10.5 mg) was identified as Albanin G, also known as Kuwanon H or Moracenin A, another Diels-Alder adduct of a chalcone and prenylphenyl moiety by HRESIMS (m/z) [M−H]$^−$=759; UV λ$_{max}$ (MeOH): 265, 320 nm; $^{13}$C NMR (126 MHz, METHANOL-d$_4$) δ ppm 16.35 (1C) 16.47 (1C) 20.96 (1C) 21.79 (1C) 23.32 (1C) 24.51 (1C) 24.53 (1C) 33.74 (1C) 35.61 (1C) 36.81 (1C) 37.77 (1C) 97.19 (1C) 102.27 (1C) 102.33 (1C) 104.24 (1C) 106.07 (1C) 106.53 (2C) 107.34 (1C) 112.37 (1C) 113.94 (1C) 114.35 (1C) 120.17 (1C) 121.60 (1C) 122.31 (2C) 123.25 (1C) 130.21 (2C) 131.33 (2C) 132.96 (1C) 156.37 (3C) 157.07 (1C) 159.59 (1C) 160.37 (1C) 161.23 (1C) 161.77 (1C) 161.96 (1C) 162.21 (1C) 182.45 (1C) 208.82 (1C).

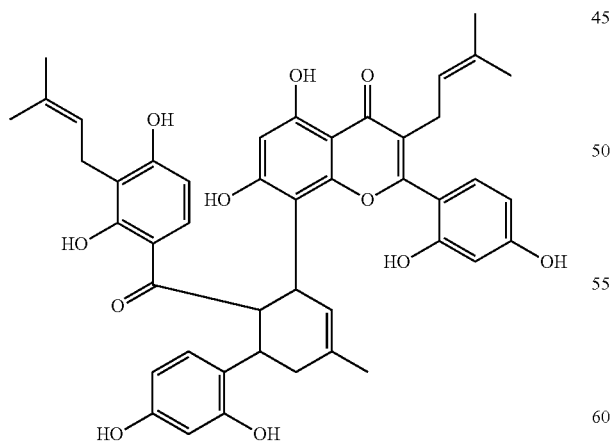

Albanin G

Compound 3 (12.9 mg) was identified as Morusinol by ESIMS (m/z) [M−H]$^−$=437; UV λ$_{max}$ (MeOH): 269, 317 nm; $^1$H NMR (500 MHz, METHANOL-d$_4$) δ ppm 1.08 (s, 6H) 1.43 (s, 6H) 1.60 (m, 2H) 2.43 (m, 2H) 5.59 (d, J=9.97 Hz, 1H) 6.16 (s, 1H) 6.43 (m, 2H) 6.59 (d, J=10.26 Hz, 1H) 7.15 (d, J=9.09 Hz, 1H); $^{13}$C NMR (126 MHz, METHANOL-d$_4$) δ ppm 21.52 (t, 1C) 28.54 (q, 2C) 28.88 (q, 2C) 43.19 (t, 1C) 71.56 (s, 1C) 79.28 (s, 1C) 100.28 (d, 1C) 102.35 (s, 1C) 104.06 (d, 1C) 106.05 (s, 1C) 108.26 (d, 1C) 113.14 (s, 1C) 115.89 (d, 1C) 122.99 (s, 1C) 128.36 (d, 1C) 132.37 (d, 1C) 153.97 (s, 1C) 157.96 (s, 1C) 160.62 (s, 1C) 162.13 (s, 1C) 162.88 (s, 1C) 163.63 (s, 1C) 184.09 (s, 1C)

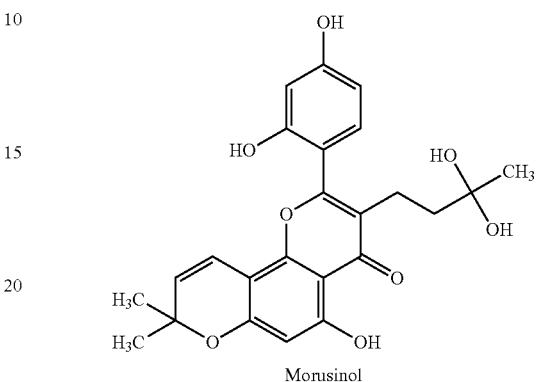

Morusinol

Another best active pool (containing 538 mg of material) was fractionated on a preparative C18 column (30 cm×250 cm) with a gradient mobile phase of water (A) and methanol (B) over 60 minutes at a flow rate of 20 mL/minute to generate 16 fraction pools. A prenylphenylated Compound 4, called Morusin (80 mg), also known as Mulberrochromene was isolated. The structure and spectroscopy data were as follows: ESIMS (m/z) [M−H]$^−$ 419; UV λmax (MeOH): 269.4 nm; 1H NMR (500 MHz, METHANOL-d4) δ ppm 1.41 (m, 9H) 1.58 (s, 3H) 3.10 (d, J=7.15 Hz, 2H) 5.09 (m, 1H) 5.57 (d, J=10.49 Hz, 1H) 6.14 (s, 1H) 6.40 (m, 2H) 6.59 (d, J=10.01 Hz, 1H) 7.10 (d, J=8.11 Hz, 1H); 13C NMR (126 MHz, METHANOL-d4) δ ppm 16.25 (q, 1C) 23.48 (t, 1C) 24.42 (q, 1C) 26.99 (q, 2C) 77.70 (s, 1C) 98.69 (d, 1C) 100.79 (s, 1C) 102.43 (d, 1C) 104.51 (s, 1C) 106.63 (d, 1C) 111.67 (s, 1C) 114.35 (d, 1C) 120.63 (d, 1C) 121.30 (d, 1C) 126.73 (d, 1C) 131.02 (d, 1C) 131.42 (s, 1C) 152.36 (s, 1C) 156.51 (s, 1C) 159.04 (s, 1C) 160.61 (s, 1C) 161.27 (s, 1C) 162.14 (s, 1C) 182.44 (s, 1C).

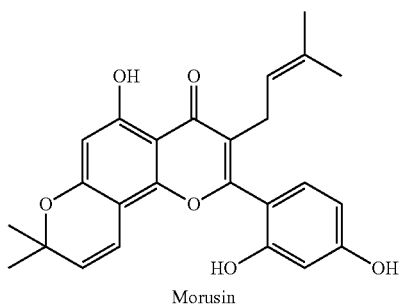 [SMILES: CC(C)=CCc1c(-c2ccc(O)cc2O)oc2c3c(cc(O)c2c1=O)OC(C)(C)C=C3]

Morusin

Example 4

Preparation of Organic 70% EtOH Extracts from *Morus alba*

2 kg of dried *Morus alba* roots and root barks were cut, crushed, and then extracted with approximately ten-fold volume (20 L) of 70% ethyl alcohol in water (v/v); the extraction was carried on at 80° C. for 5 hrs. The ethanol solution was filtered to obtain the supernatant which was then concentrated with an evaporator under vacuum at 40° C. This extraction and concentration procedure was repeated two times. The extraction solutions were then combined together and concentrated until the volume become 1/25 of the original volume. The concentrated solution was dried by vacuum freeze-drying to obtain 283.5 g of *Morus alba* 70% EtOH extract powder 1-01. The extraction yield was about 14.7% (w/w).

Example 5

Isolation of Mulberroside a from *Morus ALBA* EtOH Extracts

A 20 g amount of *Morus alba* 70% ethyl alcohol extract 1-01 from Example 4 was loaded onto silica gel column and the column was eluted with a stepwise application of solvent mixture containing linear gradient of hexane:EtOAc (5:1 to 1:5) to give eight sub-fractions. Among the eight subfractions, the 8$^{th}$ fraction was subjected to a RP-HPLC column (YMC-ODS) 5 µm, C18 (250×30 mm) by injection onto a preparative HPLC system (JAI, LC-9104, Japan) eluted with 15% Acetonitrile in H$_2$O in 16.2 min with UV wavelength 330 nm to afford Compound 5 (mulberroside A) (191 mg).

Compound 5 (mulberroside A, C$_{26}$H$_{32}$O$_{14}$): APCI-MS (m/z) [M+H]$^+$ 569.58; UV $\lambda_{max}$ (MeOH): 217.9, 325.6 nm; $^1$H NMR (400 MHz, DMSO-d$_6$) δ ppm 6.34 (brs, 1H) 6.52 (dd, J=8.6, 2.4 Hz, 1H) 6.54 (d, J=2.4 Hz, 1H) 6.57 (s, 1H) 6.64 (s, 1H) 6.94 (d, J=16.4 Hz, 1H) 7.22 (d, J=16.4 Hz, 1H) 7.45 (d, J=8.6 Hz, 1H); $^{13}$C NMR (125 MHz, DMSO-d$_6$) δ ppm 60.58 (t, G-6') 60.62 (d, G-6) 69.56 (d, G-4) 69.63 (d, G-4' 73.20 (d, G-2') 73.29 (d, G-2) 76.61 (d, G-3') 76.61 (d, G-3) 77.00 (d, G-5') 77.04 (d, G-5) 100.39 (s, G-1') 100.76 (s, G-1) 102.65 (d, C-2') 103.86 (d, C-3) 105.35 (d, C-4' 106.52 (d, C-5) 107.46 (d, C-6') 117.86 (s, C-1) 123.47 (d, C-6) 126.00 (d, a) 127.27 (d, b) 139.77 (s, C-1') 155.86 (s, C-2) 157.96 (s, C-4) 158.40 (s, C-5') 158.92 (s, C-3')

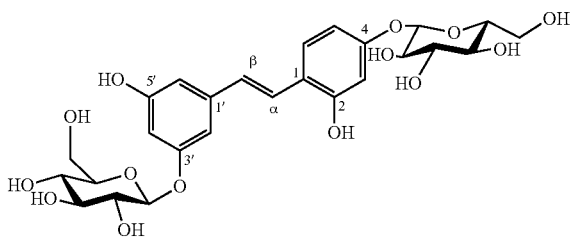

Example 6

Compounds Purified from *Milicia excelsa* (African Teak)

The organic extract (8 g) from the stem barks of *Milicia excelsa*, obtained using the methods described in Example 1, was divided and loaded separately onto two pre-packed flash columns (120 g silica, particle size 32-60 µm, 4 cm×19 cm), then the column was eluted with the gradient as described in Example 4. A prenylated flavonoid—Compound 6—was isolated from one of the active fractions and identified as Sanggenon C/D/O.

The structure and spectroscopy data of Compound 6 was as follows: ESIMS (m/z) [M−2H]_ 706; UV $\lambda_{max}$ (MeOH): 265, 320 nm; $^1$H NMR (500 MHz, METHANOL-d$_4$) ppm 1.55 (s, CH$_3$, 3 H) 1.58 (s, CH$_3$, 3 H) 1.82 (m, CH$_3$, 3 H) 2.28 (dd, J=18.65, 5.09 Hz, 1H) 2.39 (dd, J=17.80, 5.09 Hz, 1H) 2.69 (m, 1H) 2.94 (m, 1H) 3.87 (d, J=6.78 Hz, CH, 1H) 4.16 (br. s., CH, 1H) 4.49 (br. s., CH, 1H) 5.19 (br. s., 1H) 5.45 (br. s., 1H) 5.64 (s, 1H) 6.11 (d, J=2.26 Hz, 1H) 6.17 (dd, J=8.48, 2.26 Hz, 1H) 6.23-6.34 (m, 3H) 6.42 (dd, J=8.20, 1.70 Hz, 1H) 6.86 (d, J=8.19 Hz, 1H) 7.21 (d, J=8.48 Hz, 1H) 8.08 (d, J=8.76 Hz, 1H).

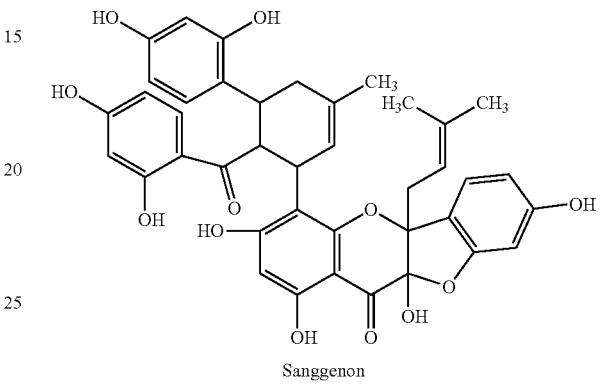

Sanggenon

Example 7

Preparation of Various *Milicia excelsa* Extracts

*Milicia* EtOAc extract fraction 7 was produced as follows: 5 kg of dried *Milicia excelsa* stem barks were cut, crushed, and extracted with approximately 4-fold volume (20 L) of ethyl alcohol (Food grade, Korea Ethanol Supplies Company, Korea) in water (v/v). The extraction solvent was treated at 80° C., for 4 hrs and the resulting extraction was filtered to obtain a supernatant that was concentrated with evaporator at 40° C. The above-described extraction procedure was repeated two times. The resulting extraction solutions were combined together and concentrated until the volume become 1/25 of the original volumes. The concentrated solution was then dried by vacuum freeze-drying to obtain 200 g of crude *Milicia excelsa* EtOH extract powder.

196 g of crude *Milicia excelsa* EtOH extract powder prepared in the above procedure was suspended in 2 L of distilled water and the suspension was vigorously mixed with 2 L of n-hexane to obtain an n-hexane soluble fraction and water-soluble fraction. The n-hexane soluble fraction was collected and the residual solution was subjected to a second n-hexane extraction. The above-described procedure was repeated four times and the resulting n-hexane soluble fractions were combined and evaporated under vacuum to obtain 74.8 g of n-hexane soluble extract 7-1 of *Milicia excelsa* stem bark.

The water-soluble fraction of *Milicia excelsa* stem bark prepared in the above procedure was vigorously mixed with an equivalent volume of ethyl acetate to obtain an ethyl acetate soluble fraction and a water-soluble fraction. The ethyl acetate soluble fraction was collected and the residual solution was subjected to the ethyl acetate extraction again. This procedure was repeated four times. The ethyl acetate soluble fractions and water-soluble fractions were respectively evaporated under vacuum to obtain 63.9 g of ethyl acetate soluble extract fraction 7 and 35.34 g of water-soluble extract 7-2 of *Milicia excelsa* stem bark.

Example 8

Preparation and HPLC Quantification of Extracts from *Morus* Plants

*Morus* samples were collected from different plant parts in different geological locations in S. Korea. The dry plant materials were ground into powder. Mixed 20 grams of *Morus* plant powder with enough Diatomaceous earth to fill up a 100 mL extraction cell, and extracted with 70% Ethanol/water by using ASE 350 Extractor (Extraction condition: Heat=5 minutes, Static=5 minutes, Flush=80 volume, Purge=900 seconds, Cycles=3, Pressure=1500 psi, Temperature=60° C.). After extraction, the solution was concentrated with an evaporator at 50° C. to produce a solid extract.

The target components Mulberroside A, Oxyresveratrol, Kuwanon G, Albanin G and Morusin in the *Morus* extracts were quantified with a Luna C18 reversed-phase column (Phenomenex, 10 µm, 250 mm×4.6 mm) in a Hitachi HPLC system at 325 nm. The column was eluted with a binary gradient of 0.1% Formic acid in water (mobile phase A) and acetonitrile (mobile phase B) at 1 ml/min flow rate and 30° C. column temperature.

TABLE 1

Gradient Table of HPLC Analytical Method

| Time (min) | Mobile phase A | Mobile phase B |
|---|---|---|
| 0.0 | 90 | 10 |
| 8.0 | 85 | 15 |
| 35.0 | 10 | 90 |
| 35.1 | 0 | 100 |
| 38.0 | 0 | 100 |
| 38.1 | 90 | 10 |
| 45.0 | 90 | 10 |

Reference Standard Material 72-1 (*Morus* 70% EtOH extract 1-01) produced according to Example 4 was utilized as the quantification standard. All extract samples were prepared in a concentration around 5 mg/ml in MeOH. After sonicating for approximately 15 minutes, the sample solution was cooled in a flask to room temperature and filtered through a 0.45 um nylon syringe filter and 20 µl of the sample was injected into the column.

*Morus* plants were collected from South Korea and China from different geological locations in both countries. The HPLC quantification of Mulberroside A, Oxyresveratrol, Kuwanon G, Albanin G and Morusin content in different species, different plant parts, collected from different locations, and at different age of plants, are listed in Tables 2 and 3. The actives have been qualified from *Morus* root bark, root wood, fine roots, stem bark, branch, branch bark, branch wood, and twigs. There are small amounts of stilbene-type compounds—Mulberroside A and Oxyresveratrol—detected in *Morus* leaf.

TABLE 2

Quantification of Active Compounds in *Morus* Collected from S. Korea.

| | | Active Content in Extract (%) | | | | | |
|---|---|---|---|---|---|---|---|
| *Morus* No. | Plant Part | Mulberroside A | Oxy-resveratrol | Kuwanon G | Albanin G | Morusin | Extraction Yield (%) |
| MK-1 | Root bark | 10.93 | 0.07 | 1.66 | 0.82 | 0.55 | 23% |
| MK-2 | Root bark | 11.58 | 0.75 | 2.79 | 1.18 | 1.21 | 19% |
| MK-3 | Root wood | 6.40 | 2.26 | 0.58 | 0.20 | 0.24 | 8% |
| MK-4 | Fine root | 9.58 | 2.15 | 2.98 | 1.73 | 1.35 | 15% |
| MK-5 | Stem bark | 2.89 | 0.16 | 0.27 | 0.42 | 0.48 | 19% |
| MK-6 | Root bark | 0.36 | 0.16 | 0.23 | 0.00 | 0.09 | 18% |
| MK-7 | Root bark | 13.28 | 0.00 | 0.25 | 0.00 | 0.00 | 27% |
| MK-8 | Root bark | 11.71 | 0.08 | 0.63 | 0.25 | 0.15 | 21% |
| MK-9 | Root bark | 17.63 | 0.48 | 2.80 | 0.66 | 1.56 | 21% |
| MK10 | Root bark | 0.28 | 0.19 | 1.70 | 0.06 | 0.05 | 16% |
| MK-11 | Leaves | 0.54 | 0.06 | 0.00 | 0.00 | 0.00 | 23% |
| MK-12 | Fruit | 0.00 | 0.00 | 0.00 | 0.00 | 0.00 | 35% |
| MK-13 | Branch | 3.31 | 4.07 | 0.14 | 0.00 | 0.18 | 9% |
| MK-14 | Root bark | 12.51 | 0.39 | 5.73 | 2.48 | 2.42 | 22% |
| MK-15 | Root wood | 1.58 | 2.52 | 0.36 | 0.14 | 0.12 | 7% |
| MK-16 | Branch bark | 22.46 | 0.09 | 0.58 | 0.00 | 0.57 | 15% |
| MK-17 | Branch wood | 4.95 | 1.78 | 0.17 | 0.00 | 0.00 | 5% |
| MK-18 | Root bark | 0.41 | 0.28 | 3.36 | 0.11 | 0.18 | 14% |

TABLE 3

Quantification of Active Compounds in *Morus* Collected from China

| Morus No. | Plant Part | Active Content in Extract (%) | | | | | Extraction Yield (%) |
|---|---|---|---|---|---|---|---|
| | | Mulberroside A | Oxy-resveratrol | Kuwanon G | Albanin G | Morusin | |
| MC-1 | Root bark | 1.74 | 0.10 | 7.29 | 6.31 | 5.38 | 17% |
| MC-2 | Root bark | 3.42 | 0.37 | 4.69 | 1.00 | 1.97 | 18% |
| MC-3 | Root bark | 0.04 | 0.05 | 0.34 | 0.00 | 0.12 | 8% |
| MC-4 | Root bark | 0.11 | 0.60 | 0.39 | 0.00 | 0.14 | 8% |
| MC-5 | Root bark | 0.24 | 0.22 | 0.73 | 0.00 | 0.18 | 9% |
| MC-6 | Root bark | 14.07 | 0.36 | 2.06 | 1.29 | 1.42 | 20% |
| MC-7 | Root bark | 9.96 | 1.01 | 2.51 | 0.73 | 0.78 | 12% |
| MC-8 | Root bark | 0.21 | 2.64 | 0.06 | 0.46 | 1.40 | 12% |
| MC-9 | Root bark | 5.85 | 1.44 | 5.11 | 2.41 | 8.70 | 19% |
| MC-10 | Root bark | 2.81 | 0.76 | 11.43 | 4.21 | 3.82 | 11% |
| MC-11 | Root bark | 0.03 | 0.01 | 0.40 | 0.75 | 0.10 | 11% |
| MC-12 | Fruit | 0.00 | 0.00 | 0.00 | 0.00 | 0.00 | 74% |
| MC-13 | Leaves | 0.00 | 0.00 | 0.13 | 0.00 | 0.00 | 20% |
| MC-14 | Twigs | 2.67 | 0.90 | 0.06 | 0.17 | 0.03 | 4% |

Example 9

HPLC Quantification of Extracts from *Morus* Root Bark

Ethanol extracts of *Morus* root barks were obtained from different geological locations in China. The contents of four active components—Mulberroside A, Kuwanon G, Albanin G and Morusin—in those *Morus* extracts were quantified with the HPLC method described in Example 8. As shown in the Table 4, two *Morus* extracts (ME-10 and ME-12) contained none of the four active compounds. Three *Morus* extracts (ME-6, ME-7 and ME-8) contained no Mulberroside A and very small amounts of prenylated flavonoids (less than 4% as a total of the 3 compounds present). Another four *Morus* extracts (ME-3, ME-4, ME-5, and ME-14) contained small amounts of prenylated flavonoids (less than 2% as a total of the 3 compounds present) and variable amount of Mulberroside A. This example clearly demonstrates the lack of enrichment and standardization of stilbene and prenylated flavonoids in regular *Morus* root bark extracts.

TABLE 4

Quantification of Active Compounds in *Morus* Extracts from China

| Morus Extract | Active Content in Extract (%) | | | |
|---|---|---|---|---|
| | Mulberroside A | Kuwanon G | Albanin G | Morusin |
| ME-1 | 20.4 | 2.17 | 0.77 | 1.31 |
| ME-2 | 22.26 | 2.57 | 0.83 | 1.49 |
| ME-3 | 10.86 | 0.42 | 0.17 | 0.22 |
| ME-4 | 1.07 | 0.22 | 0.13 | 0.13 |
| ME-5 | 2.3 | 0.54 | 0.27 | 0.23 |
| ME-6 | 0 | 0.45 | 0.15 | 0.95 |
| ME-7 | 0 | 0.47 | 0.16 | 0.99 |
| ME-8 | 0 | 1.32 | 0.35 | 2.08 |
| ME-9 | 6.7 | 2.29 | 0.99 | 0.91 |
| ME-10 | 0 | 0 | 0 | 0 |
| ME-11 | 6.13 | 2.15 | 1.02 | 0.93 |
| ME-12 | 0 | 0 | 0 | 0 |
| ME-13 | 8 | 2.8 | 1.01 | 1.06 |
| ME-14 | 6.49 | 0.85 | 0.22 | 0.21 |

Example 10

Preparation of *Morus alba* 70% EtOH Extract 10

Dried *Morus alba* roots and root barks (93.3 kg) were cut, crushed, and then extracted with approximately seven-fold volume (700 L) of 70% ethyl alcohol in water (v/v); the extraction was carried out at 100° C. for 4 hrs. The ethanol solution was filtered to obtain the supernatant, which was then concentrated with an evaporator under vacuum at 40° C. This extraction and concentration procedure was repeated two times. The extraction solutions were then combined together and concentrated until the volume become 1/25 of the original volume. The concentrated solution was dried by vacuum freeze-drying to obtain 18.3 kg of *Morus alba* 70% EtOH extract powder 10. The extraction yield was about 19.6% (w/w). The major active component content is listed in Table 4 of Example 14.

Example 11

Preparation of *Morus alba* EtOAC Fraction 11

*Morus alba* EtOH extract produced according to Example 10 was extracted with approximately two-fold volume of ethyl alcohol (EP grade, Ducksan Chemical, Korea) from 4 kg of dried *Morus alba* root bark yielded 570 g of *Morus alba* EtOH extract powder. The EtOH extract was partitioned with hexane and water followed by extraction with ethyl acetate. Extraction was performed by homogenization of the extraction solution at 15,000 rpm for five minutes with homogenizer (IKA T25D, Germany). The well homogenized extraction solution was then separated by centrifuge (Beckman J-20XP, Germany) at 3,000 rpm (rotor #JLA 8.1000) for five minutes. Corresponding n-hexane soluble and water soluble extracts were prepared from 570 g of the crude *Morus alba* EtOH powder. This resulted in production of 80.5 g of the n-hexane soluble extract and 156 g of the water-soluble extract of *Morus alba*. After solvent partition with EtOAc, the upper layer (EtOAc soluble layer) was filtered by filter paper (Hyundai Micro, No. 20, Korea) and the EtOAc solution was collected. The residue (precipitate material) collected from the centrifugation was re-extracted with two-fold volume (300 L) of ethyl acetate (EP grade, Ducksan Chemical, Korea). The re-extracted solution was agitated at 150 rpm for 2 hours. The resulting mixture was then filtered (Hyundai Micro, No. 20, Korea) to obtain an additional EtOAc extract solution. The above-described procedure was repeated two times. The three resulting EtOAc extract solutions were combined and concentrated by evaporator at 40° C. to obtain the final EtOAc extract 11. The final amount of *Morus alba* EtOAc fraction 11, obtained from this process was 327 g. The major active component content is provided in Table 4 (Example 14).

Example 12

Preparation of *Morus alba* 70% EtOH Precipitate Extract 12

*Morus alba* EtOH precipitate extract 12 was produced by follows; 634 kilograms (KG) of dried *Morus alba* roots and root barks were cut, crushed and extracted with approximately 7 fold volume (3600 liters (L)) of 70% ethyl alcohol in water (v/v); the extraction solvent was treated at 80° C., for 4 hrs; the residue was filtered to obtain the supernatant which was then concentrated with an evaporator at 40° C. The above-described procedure was repeated three times. The extraction solutions were then concentrated until the volume become about 1/30 the original starting volumes. Then the concentrated solutions were combined to evaporate again in order to reduce volume of concentrated solution until 1/90 volume of the original extraction solution. The concentrated solution was rested at room temperature for 24 hours (hr) to allow separation into two layers (supernatant and precipitate-layer). The precipitate was filtered and dried by vacuum freeze-drying to obtain *M. alba* 70% EtOH precipitate powder. A total of 24 kg of the resulting product was obtained from 634 kg of raw plant material. The extraction yield was about 3.79% (w/w). The major active component content is listed in Table 4 (Example 14).

Example 13

Preparation of *Morus alba* 70% EtOH Extract (13-1), Precipitate (13-2), and Supernatant (13-3) Extracts

*Morus alba* EtOH precipitate extract was produced as follows: 465 kg of dried *Morus alba* roots and root bark were cut, crushed, and extracted with approximately 10-fold volume (4500 L) of 70% ethyl alcohol in water (v/v); the extraction solvent was treated at 80° C. for 4 hrs; the residue was filtered to obtain the supernatant which was concentrated with an evaporator at 40° C. Above-described procedure was repeated three times. The extraction solutions were concentrated until the volume become 1/30 the original volume. The concentrated solutions were then combined and evaporated again to reduce the volume of the concentrated solution until 1/90 volume of the original extraction solution was achieved. The concentrated solution was left at room temperature for 24 hr to allow separation into a supernatant and precipitate layer. The precipitate layer was then dried by vacuum to obtain 12 kg of *Morus alba* 70% EtOH precipitate powder 13-2. The precipitate yield from *Morus* root barks was about 2.6% (w/w). The supernatant layer was dried by vacuum drying to obtain 24 kg *Morus* alba 70% EtOH supernatant powder 13-3. The extraction yield for the supernatant 13-3 was about 5.2%.

*Morus* alba 70% EtOH combination extract (13-1) was obtained by blending 2 kg of precipitate (13-2) and 4 kg of supernatant (13-3)). The major active component content in both *Morus alba* EtOH extract 13-1, precipitate 13-2 and supernatant 13-3 is listed in Table 4 (Example 14).

Example 14

HPLC Quantification of Active Content in Different *Morus alba* Extracts

The detailed HPLC quantification method for Mulberroside A, Oxyresveratrol, Kuwanon G, Albanin G and Morusin content was described in Example 8. Table 4 listed the active contents in different *Morus* root bark extracts as prepared in the Examples 10, 11, 12 and 13.

TABLE 5

Quantification of Active Compounds in *Morus* Extracts

| *Morus* Extracts | Stilbene in Extract (%) | | | Prenylated Flavonoid in Extract (%) | | | |
|---|---|---|---|---|---|---|---|
| | Mulberroside A | Oxy-resveratrol | Total Stilbenes | Kuwanon G | Albanin G | Morusin | Total Prenylated Flavonoids |
| 10 | | | | 2.88 | 1.64 | | |
| 11 | 1.55 | 0.33 | 1.89 | 9.31 | 6.74 | 6.84 | 22.89 |
| 12 | 1.27 | 0 | 1.27 | 5.30 | 4.28 | 4.25 | 13.83 |
| 13-1 | 7.31 | 0.26 | 7.57 | 3.12 | 1.71 | 2.01 | 6.84 |
| 13-2 | 0.76 | 0 | 0.76 | 5.51 | 3.98 | 4.48 | 13.97 |
| 13-3 | 7.50 | 0 | 7.50 | 1.27 | 0.36 | 0.48 | 2.11 |

Example 15

Preparation of Organic Extracts from *Curcuma longa*

A total of 20 grams of dried rhizome powder of *Curcuma longa* were loaded into two 100 ml stainless steel tube and extracted twice with an organic solvent mixture (methylene chloride/methanol in a ratio of 1:1) using an ASE 300 automatic extractor at 80° C. and under 1,500 psi of pressure. The extract solution was filtered, collected, and evaporated with a rotary evaporator to give crude organic extract (OE) (6.04 g, 30.2% yield).

Example 16

High Throughput Purification (HTP) of *Curcuma longa* Organic Extracts

The *Curcuma longa* organic extract (OE, 400 mg) as described in Example 15 was loaded onto a pre-packed flash column (2 cm ID×8.2 cm, 25 ml, 10 g silica gel), eluted using a Hitachi high throughput purification (HTP) system with an unique gradient mobile phase of (A) 50:50 EtOAc: hexanes and (B) methanol from 100% A to 100% B in 30 minutes at a flow rate of 5 mL/min. A total of 88 fractions were collected in a 96-deep-well plate at 1.9 mL per well using a Gilson fraction collector. The sample plate was dried under low vacuum and centrifugation, and then the dried samples were resuspended in 1.5 mL dimethyl sulfoxide (DMSO) per well. A portion (100 μL) from each well was taken and combined (based on UV trace) for the BKB1 inhibition assay.

Example 17

Bradykinin B1 Radioligand Binding Assay of *Curcuma* Extracts and Fractions Thereof Bradykinin B1 (BKB1) radioligand binding assay was conducted to determine the inhibition activity of *Curcuma longa* OE and extract fractions on BKB1 binding to BKB1 receptor (BKB1R). Membranes from human IMR-90 lung fibroblasts, stimulated with IL-1β in modified HEPES buffer (PH=7.4), were incubated with a test sample in the presence of 0.9 nM [$^3$H](Des-Arg$^{10}$)-Kallidin for 60 minutes at room temperature. After incubation, membranes were filtered and washed five times with modified DPBS buffer (pH=7.4). Samples were scintillation counted to determine the amount of specifically bound to the BKB1 receptor containing membrane.

The *Curcuma longa* OE was tested at a concentration of 166 μg/mL and IC$_{50}$ values were determined using the same method with serial dilutions at concentrations ranging from 400 μg/mL and 5 ng/mL to obtain a dose-response curve. Data showing inhibition of BKB1 binding to BKB1R by *Curcuma longa* OE extracts is provided in Table 6.

TABLE 6

| Inhibition of BKB1Receptor Binding by *Curcuma longa* OE | | |
|---|---|---|
| Sample | BKB1(166 μg/ml) POC (%) | BKB1 IC$_{50}$ (μg/mL) |
| OE extract | −0.14 | 9.6 |

*Curcuma longa* OE showed strong inhibition of BKB1 binding with an IC$_{50}$ of about 9.6 μg/mL. Furthermore, HTP fractions of the *Curcuma longa* OE were examined in the BKB1 binding assay (see FIG. 1). The activity profile of the HTP fractions indicates that fractions 11-22, 34, and 38 had the most potent BKB1 receptor binding inhibition, with a mean percentage of control (POC) below 10%. Curcuminoids were found to be the major active compounds associated with the activity of HTP fractions 11-22.

Example 18

BKB1 and BKB2R Binding Activity of *Curcuma* Compounds

BKB1 binding assay, as described in Example 17, was used to test curcumin compound isolated from a *Curcuma longa* extract (Compound 11), as well as commercially available curcumin purchased from Sigma-Aldrich (C1386). Curcumin was tested at final concentrations ranging from 200 μM to 5 nM. Binding curves were plotted by non-linear regression fit (using GraphPad Prizm software). K$_i$ values were computed using Cheng-Prusoff algorithm. In addition, inhibition of BKB2 receptor binding activity by curcumin was examined with methods similar to those described in Example 17 for the BKB1 receptor with some modifications. Bradykinin Radioligand Binding Assay (BKB2) was conducted using a standard assay under the following conditions:

1. Composition of Assay Buffer: 24 mM TES, pH 6.8, 1 mM 1.10-Phenanthrioline, 0.3% BSA.
2. Source of BKb2R: CHO-K1 cells expressing recombinant human BKb2R
3. Ligand: [$^3$H]-Bradykinin: 0.2 nM.
4. Incubation time: 90 min RT.
5. Reading: TopCount.

Commercial curcumin (Sigma, C1386) was tested at concentrations ranging from 200 μM to 5 nM. Binding curves for commercial curcumin does not conform to mass action law for competitive inhibitor. K$_1$ was manually calculated by using Cheng-Prusoff equation. The inhibition activity for BKB1 and BKB2 by curcumin is provided in Table 7.

TABLE 7

| Inhibition of BKB1 and BKB2 by Curcumin | | |
|---|---|---|
| Compound | BKB1 Ki (μg/ml) | BKB2 Ki (μg/ml) |
| Curcumin | 2.173 | 58 |

The data indicate that curcumin is a selective BKB1 antagonist since it shows much stronger inhibition of BKB1 binding activity as compared to BKB2 binding.

Example 19

Preparation of *Curcuma longa* Ethyl Alcohol Extract 19

*Curcuma* EtOH extract was produced as follows: 20 kg of dried *Curcuma longa* rhizomes (roots) were pulverized, and extracted with approximately 4-fold volume (80 L) of 100% ethyl alcohol and the extraction solvent held at 80-85° C. for 30 hrs. The residue was filtered to obtain a supernatant that was concentrated with an evaporator at 85-90° C. The extraction solutions were then concentrated until the volume was 1/25 of the original volume. The concentrated solution was dried by spray dry process (temperature I/P 200° C. and O/P 95° C.) to obtain about 1 kg of 25% *Curcuma* in EtOH extract powder 19 with reddish-orange color. The extraction yield was about 5% (w/w).

Example 20

Quantification of Curcumin in *Curcuma* Rhizome Extract

The following analytical method was used to determine the amount of Curcumin in the *Curcuma longa* rhizome extracts. An Agilent HPLC/PDA system was used with a C18 reversed-phase column (Phenomenex, USA, Luna 5 um, 250 mm×4.6 mm) for detection and quantitation of Curcumin and minor components. A binary 0.1% acetic acid in purified water (mobile phase A) and acetonitrile (mobile phase B) gradient was used for elution of Curcumin components as described in Table 7. The flow rate was set to 1 ml/min passing through the Luna C18 column with a column temperature of 35° C. The UV detector was set to read absorbance at 407 nm.

TABLE 7

Curcumin HPLC Gradient Elution Scheme

| Time (min) | Mobile phase A % | Mobile phase B % |
|---|---|---|
| 0 | 55 | 45 |
| 10.0 | 55 | 45 |
| 10.1 | 10 | 90 |
| 25.0 | 10 | 90 |
| 25.1 | 55 | 45 |
| 30.0 | 55 | 45 |

The quantification standard—Curcumin was purchased from Sigma-Aldrich Co. The highest concentration level of Curcumin was 0.05 mg/ml and diluted to L5 from L1 (0.0031 mg/ml) using methanol. Concentration of *Curcuma longa* rhizome extract samples were adjusted to about 1 mg/ml in methanol in a volumetric flask and sonicated until dissolved (approximately 20 minutes), then cooled to room temperature, mixed well and filtered through a 0.45 μm nylon syringe filter. Then 10 μl of sample was quantified by HPLC, which results for *Curcuma longa* rhizome extract are provided in Table 8.

TABLE 8

HPLC Quantification of *Curcuma longa* Rhizome Extract

| Sample | Curcumin % | Curcuminoids (total) % |
|---|---|---|
| 110 | 16.34 | 30.04 |
| 210 | 14.71 | 27.93 |
| 310 | 13.08 | 26.53 |

Example 21

Preparation of Gambir (*Uncaria gambir*) Extract 21

*Uncaria gambir* water extract was produced as follows. 100 kg of dried leaves of *Uncaria gambir* was cut, crushed, and extracted with 15-fold volume (1500 L) of 70% ethyl alcohol and the extraction solvent treated at 80° C. for 7 hrs. The resulting residue was filtered to obtain a supernatant. The above-described procedure was repeated for second time. The extraction supernatant solutions were combined together and concentrated with an evaporator at 46° C. under vacuum condition until the volume became $1/30^{th}$ of the original volume. The concentrated solution was evaporated further to reduce volume of concentrated solution until 1/90 volume of the original solution. The resulting concentrated solution was then rested at room temperature for 24 hrs to allow precipitate to form in the concentrated solution. The precipitate was filtered and dried under vacuum to obtain precipitate powder as *Uncaria gambir* extract powder 21. The yield from 100 kg of dried leaves of *Uncaria gambir* was about 6 kg of extract powder, so the extraction yield was about 6% (w/w).

Example 22

HPLC Quantification of *Uncaria gambir* Extracts

The following analytical method was used to determine the amount of catechin in the *Uncaria gambir* leaf extracts. An Agilent HPLC/PDA system with a C18 reversed-phase column (Phenomenex, USA, Luna 5 um, 250 mm×4.6 mm) was used for the detection and quantitation of catechin compound in Gambir extracts. A binary column gradient was used for elution of material from the column. Mobile Phase A: 0.1% phosphoric acid in purified water, and Mobile Phase B: acetonitrile gradient was used for elution (Table 9). The flow rate was set to 1.0 ml/min passing through the Luna C18 column with a column temperature of 35° C. The UV detector was set to record absorbance at 275 nm.

TABLE 9

Gradient Table of HPLC Analytical Method

| Time (min) | Mobile Phase A | Mobile Phase B |
|---|---|---|
| 0.0 | 85.0 | 15.0 |
| 7.0 | 85.0 | 15.0 |
| 12.0 | 10.0 | 90.0 |
| 16.5 | 10.0 | 90.0 |
| 16.6 | 85.0 | 15.0 |
| 24.0 | 85.0 | 15.0 |

Pure catechin reference sample was purchased from Sigma-Aldrich Co. The reference sample was dissolved in MeOH:0.1% $H_3PO_4$ (1:1). Highest level concentration range of catechin was 0.5 mg/ml and diluted to L5 from L1 (0.003 mg/ml) using 50% methanol in 0.1% $H_3PO_4$. Concentration of the Gambir extract samples were adjusted to 2 mg/ml in 50% methanol in 0.1% $H_3PO_4$ in a volumetric flask and sonicated until dissolved (approximately 10 minutes), and then cooled to room temperature, mixed well and filtered through a 0.45 μm nylon syringe filter. HPLC analysis was performed by injecting a 20 μl sample into the HPLC.

TABLE 10

HPLC Quantification of *Gambir* Extract

| Sample | Catechin % |
|---|---|
| 210 | 20.0 |
| 212 | 18.5 |

Example 23

Preparation of *Acacia catechu* 65% Catechin Extract

*Acacia catechu* 65% catechin extract was produced as follows: 500 kg of *Acacia catechu* (KATHA) was put into 750 L of 50% ethyl alcohol and stirred at room temperature for 90 min. After 500 L of ethyl acetate was put into the homogenized KATHA slurry, it was stirred smoothly for 30 min. The slurry was allowed to separate into two layers for 1 hr. The ethyl acetate layer was moved into a new bottle, and the partition was repeated with the water layer. Both the 1st and 2nd ethyl acetate layers were combined and concentrated at 60-62° C. until TDS 30%, and then spray dried (temp. I/P 190° C.-0/P 90° C.). A total of 72.5 kg *Acacia catechu* extract was obtained from 500 kg of raw material with catechin and epicatechin total content at not less than 65%. The extraction yield was 14.5% (w/w).

Example 24

Fractionation, Purification and Identification of Active Compounds from *Mentha piperita* Extracts A *Mentha piperita* methanol extract (ME) (10.6 g) as prepared in Example 26 was partitioned between hexane (100 mL) and water (150 mL) three times. The combined hexane solutions were vacuum dried to give a hexane extract (HE) of 2.19 g. The aqueous layer was extracted with ethyl acetate (100 mL) three times. The combined ethyl acetate layers were dried under vacuum to give an ethyl acetate extract (EA) of 1.26 g. The aqueous layer was then further extracted with butanol (100 mL) three times to give a butanol extract (BU) of 1.91 g. The remaining aqueous layer was freeze-dried to give an aqueous extract (WA) of 3.91 g. Each of the ME, HE, EA, BU and WA was tested for anti-nociceptive activity in an acetic acid-induced abdominal constriction model in mice. The active compounds partitioned into the EA and BU layers were further investigated. In vivo activity guided isolation led to the discovery of three active compounds.

The EA fraction (653.5 mg) was subjected to a RP-HPLC column (Phenomex) 10 μm Luna C18 (250×30 mm) by two injections on a HPLC system L6200A starting with 40% MeOH (B) in $H_2O$ (A) to 60% B in 8 min, from 60% to 100% MeOH in 27 min, and finally washed with 100% B for another 15 minutes at a flow rate of 20 mL/min with UV wavelength 230 nm to give Compound 1 (Rosmarinic acid) (136.3 mg).

Compound 7 (Rosmarinic acid): ESIMS (m/z) [M−H]⁻ 359; UV $\lambda_{max}$ (MeOH): 284, 328.6 nm; ¹H NMR (500 MHz, MeOH-d₄) δ ppm 3.00 (dd, J=14.31, 8.44 Hz, 1H) 3.09 (dd, J=14.43, 4.16 Hz, 1H) 5.18 (dd, J=8.44, 4.28 Hz, 1H) 6.26 (d, J=15.65 Hz, 1H) 6.61 (dd, J=7.95, 1.83 Hz, 1H) 6.70 (d, J=7.83 Hz, 1H) 6.75 (d, J=1.71 Hz, 1H) 6.78 (d, J=8.07 Hz, 1H) 6.95 (dd, J=8.31, 1.96 Hz, 1H) 7.04 (d, J=1.96 Hz, 1H) 7.55 (d, J=15.90 Hz, 1H); ¹³C NMR (126 MHz, MeOH-d₄) δ ppm 36.51 (t, 1C) 73.23 (d, 1C) 113.00 (d, 1C) 113.81 (d, 1C) 114.88 (d, 1C) 115.09 (d, 1C) 116.16 (d, 1C) 120.38 (d, 1C) 121.73 (d, 1C) 126.24 (s, 1C) 127.86 (s, 1C) 143.84 (s, 1C) 144.73 (s, 1C) 145.38 (s, 1C) 146.30 (d, 1C) 148.30 (s, 1C) 167.05 (s, 1C) 172.13 (s, 1C)

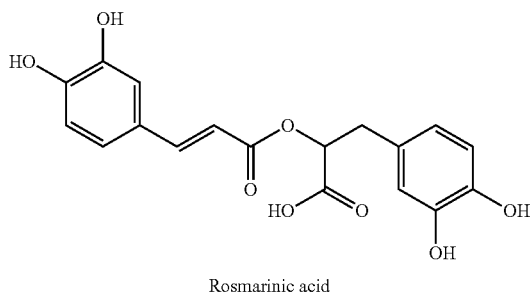 [SMILES: O=C(/C=C/c1ccc(O)c(O)c1)OC(Cc1ccc(O)c(O)c1)C(=O)O]

Rosmarinic acid

Separation of the BU fraction (1.1 g) was performed by RP-HPLC on the same column with two injections as described above starting with 30% MeOH (B) in $H_2O$ (A) for 5 min, 30% B to 50% B in 15 min, from 50% to 100% B in 20 min, and washed with 100% B for 15 minutes at a flow rate of 20 mL/min with UV wavelength 320 nm to give Compound 2 (Eriocitrin) (192.0 mg) and compound 3 (87.4 mg).

Compound 8 (Eriocitrin): ESIMS (m/z) [M−H]_ 595; UV λmax (MeOH): 228.4, 289.2, 335.5 nm; ¹H NMR (500 MHz, MeOH-d4) δ ppm 1.21 (m, 3H) 2.76 (d, J=15.41 Hz, 1H) 3.10 (m, 1H) 3.48 (m, 2H) 3.63 (m, 3H) 3.71 (m, 1H) 3.91 (m, 1H) 4.00 (d, J=9.54 Hz, 1H) 4.71 (br. s., 2H) 4.95 (d, J=6.11 Hz, 2H) 5.33 (m, 1H) 6.19 (d, J=7.58 Hz, 2H) 6.80 (br. s., 2H) 6.96 (m, 1H); ¹³C NMR (126 MHz, MeOH-d4) δ ppm 16.53 (q, 1C) 42.62 (t, 1C) 66.01 (t, 1C) 68.37 (d, 1C) 69.90 (d, 1C) 70.63 (d, 1C) 70.98 (d, 1C) 72.68 (d, 1C) 73.23 (d, 1C) 75.68 (d, 1C) 76.42 (d, 1C) 79.13 (d, 1C) 95.70 (d, 1C) 96.54 (d, 1C) 99.71 (d, 1C) 100.71 (d, 1C) 103.55 (s, 1C) 113.51 (d, 1C) 114.92 (d, 1C) 117.97 (d, 1C) 130.11 (s, 1C) 145.06 (s, 1C) 145.51 (s, 1C) 162.99 (s, 1C) 163.51 (s, 1C) 165.41 (s, 1C) 197.10 (s, 1C)

The in vivo activity of rosmarinic acid and eriocitrin were further confirmed in a carrageenan-induced paw edema and pain sensitivity model in rats. Rosmarinic acid and eriocitrin showed significant anti-inflammatory and analgesic activities at a dose of 200 mg/kg and 100 mg/kg level, respectively.

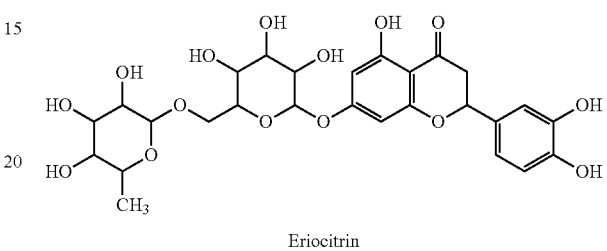

Eriocitrin

Compound 9 was assigned as Skolimoside: ESIMS (m/z) [M−H]⁻ 593; UV λmax (MeOH): 228.4, 258.1, 347.0 nm; ¹H NMR (500 MHz, METHANOL-d4) δ ppm 1.19 (d, J=6.11 Hz, 3H) 3.41 (br. s., 1H) 3.50 (br. s., 2H) 3.60-3.71 (m, 3H) 3.74 (dd, J=9.54, 3.18 Hz, 1H) 3.87-3.96 (m, 1H) 4.06 (d, J=9.78 Hz, 1H) 4.72 (s, 1H) 5.04 (br. s., 1H) 6.52 (s, 1H) 6.60 (s, 1H) 6.75 (br. s., 1H) 6.93 (d, J=8.07 Hz, 1H) 7.41 (br. s., 2H); ¹³C NMR (126 MHz, METHANOL-d4) δ ppm 16.48 (q, 1C) 66.07 (t, 1C) 68.39 (d, 1C) 69.91 (d, 1C) 70.67 (d, 1C) 71.01 (d, 1C) 72.64 (d, 1C) 73.33 (d, 1C) 75.74 (d, 1C) 76.40 (d, 1C) 94.73 (d, 1C) 99.72 (d, 1C) 100.19 (d, 1C) 100.68 (d, 1C) 102.84 (d, 1C) 105.69 (s, 1C) 112.92 (d, 1C) 115.48 (d, 1C) 119.20 (d, 1C) 122.11 (s, 1C) 145.58 (s, 1C) 149.76 (s, 1C) 157.49 (s, 1C) 161.52 (s, 1C) 163.31 (s, 1C) 165.54 (s, 1C) 182.60 (s, 1C)

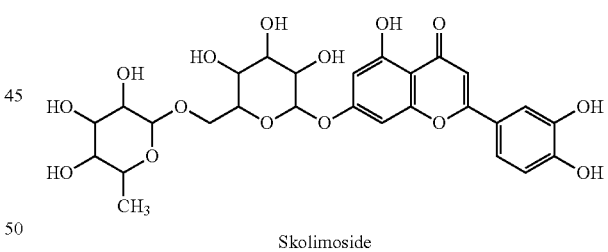

Skolimoside

Example 25

Preparation of Ethanol Extracts from *Mentha piperita*

Peppermint (*Mentha piperita*) 90% EtOH extract (lot #RM604-13002) was produced as follows: 73.4 kg of dried *Mentha piperita* was cut, crushed, and extracted with a 15-fold volume (1100 L) of 90% ethyl alcohol (v/v) at 85° C. for 3 hrs. The resulting residue was filtered to obtain a supernatant that was concentrated with a vacuum evaporator at 40° C. The resulting residue was extracted a second time with 13-fold volume (950 L) of 90% ethyl alcohol (v/v) at 40° C. for 1 hrs and filtered to obtain a second supernatant which was concentrated with a vacuum evaporator at 40° C. The resulting concentrated cake was dried under vacuum to obtain 19.3 kg of Peppermint 90% EtOH extract powder designated as Extract 25. The extraction yield was 25.3% (w/w).

Example 26

Preparation of Methanol and Other Organic Extracts from *Mentha piperita*

Dried ground peppermint leaf powder (*Mentha piperita*) (21.7 g) loaded into two 100 ml stainless steel tubes and extracted twice with an organic solvent mixture (methanol) using an ASE 300 automatic extractor at 80° C. under a pressure of 1,500 psi. The extract solution was automatically filtered, collected, and evaporated with a rotary evaporator to give a crude organic extract (ME 26-1) (4.48 g, 20.64% yield).

Alternatively, 252.3 g of dried ground leaf powder of *Mentha piperita* was extracted with methanol three times by refluxing one hour each time. The organic solution was combined and evaporated under vacuum to provide methanol extract (ME 26-2) 40.88 g with a yield of 16.20%.

Similar results were obtained using the same procedure, but with the organic solvent being replaced with methanol or ethanol to provide a methanol extract (ME) or ethanol extract (EE), Ethanol:$H_2O$ (7:3) extracts, Ethanol:$H_2O$ (1:1) extracts, Ethanol:$H_2O$ (3:7) extracts and water extracts respectively.

Example 27

Ex Vivo Glycosaminoglycans (GAG) Release Assay

Articular cartilage from hock joints of rabbits (2.5 kg body weight) was removed immediately after each animal was sacrificed and articular cartilage explants were obtained by following the method described by Sandy et al. (*Biochem. Biophy Acta* 543:36, 1978).

Briefly, after the articular surfaces were surgically exposed under sterile conditions, approximately 200-220 mg articular surfaces per joint were dissected and submerged into complete medium (DMEM, supplemented with heat inactivated 5% FBS; penicillin 100 U/ml; streptomycin 100 ug/ml). They were then rinsed several times with the complete medium and incubated for 1 to 2 days at 37° C. in a humidified 5% $CO_2$/95% air incubator for stabilization. The complete medium was replaced with a basal medium (DMEM, supplemented with heat-inactivated 1% FBS, 10 mM HEPES, and penicillin 100 U/ml streptomycin 100 μg/ml). Approximately 30 mg cartilage pieces (2×3×0.35 mm/piece) were placed in 24-well plates and treated with given concentrations of test agents. After pretreatment for 1 h, 5 ng/ml of rhIL-1α was added to the culture medium and further incubated at 37° C. in a humidified 5% $CO_2$/95% air incubator. The culture medium was collected 24 h later and stored at −20° C. until assay.

The amount of sulphated GAGs (e.g., released from proteoglycans) in the medium at the end of the reaction reflects the amount of articular cartilage degradation, which was determined using the commercially available 1,9-dimethy-methylene blue method according to the instructions of the manufacturer (Blyscan™ assay, Accurate Chemical and Scientific Corp., Westbury, N.Y.).

Example 28

Effect of Purified Compounds from *Morus* on Ex Vivo GAG Release

Rabbit cartilage explants were cultured with rhIL-1α (5 ng/ml) in the absence or presence of purified *Morus* compounds isolated according to Example 3 to examine the protective effects on proteoglycan (PG) degradation. Purified compound inhibited rhIL-1α-mediated degradation of PG in a concentration dependent manner. Especially, Mulberroside A, Oxyresveratrol and Morusin showed a strong inhibitory effect when compared with diclofenac treated group.

TABLE 12

Effect of *Morus* Compounds on Ex Vivo GAG Release

| Sample | Dose | % GAG release |
|---|---|---|
| Normal | — | 36.6 |
| IL-1α | 5 ng/ml | 100 |
| Diclofenac | 300 μg/ml | 34.6 |
| Mulberoside A | 25 μg/ml | 73.1 |
|  | 50 μg/ml | 75.8 |
|  | 100 μg/ml | 70.5 |
| Kuwanon G | 25 μg/ml | 56.6 |
|  | 50 μg/ml | 48 |
|  | 100 μg/ml | 44.4 |
| Oxyresveratrol | 25 μg/ml | 59.8 |
| Morusin | 25 μg/ml | 48.4 |
|  | 50 μg/ml | 49.9 |
|  | 100 μg/ml | 33.6 |

Example 29

*Morus* Extract Reduces Ex Vivo GAG Release

Rabbit cartilage explants were cultured with rhIL-1α (5 ng/ml) in the absence or presence of *Morus* extracts to examine the protective effects on PG degradation. *Morus* extracts inhibited rhIL-1α-mediated degradation of PG in a concentration dependent manner. All samples showed a strong effect as compared to that of IL-1α treated group.

TABLE 13

Effect of *Morus* Extracts on Ex Vivo GAG Release

| Sample | Dose | % GAG release |
|---|---|---|
| Normal | / | 36.6 |
| IL-1α | 5 ng/ml | 100 |
| Diclofenac | 300 μg/ml | 34.6 |
| 13-1 | 100 μg/ml | 50.2 |
|  | 200 μg/ml | 41.9 |
| 11 | 100 μg/ml | 49.9 |
|  | 200 μg/ml | 37.3 |
| 13-3 | 100 μg/ml | 67.20 |
|  | 200 μg/ml | 61.3 |

Example 30

Effect of *Curcuma* and *Uncaria* Extracts on Ex Vivo GAG Release

Rabbit cartilage explants were cultured with rhIL-1α (5 ng/ml) in the absence or presence of *Curcuma* extract from Example 19 or *Uncaria* extract from Example 21 to examine the protective effect on PG degradation. *Curcuma* extract 19 decreased rhIL-1α-mediated degradation of PG in a concentration dependent manner, while *Uncaria* extract 21 showed a weak protective effect on PG degradation.

TABLE 14

Effect of *Curcuma* and *Gambir* Extracts on Ex Vivo GAG Release

| Sample | Dose | % GAG release |
|---|---|---|
| (—) | — | 39.0 |
| IL-1α | 5 ng/ml | 100.0 |
| Diclofenac | 300 µg/ml | 45.6 |
| 19 | 30 µg/ml | 88.9 |
| (*Curcuma*) | 50 µg/ml | 65.0 |
| | 66.7 ug/ml | 59.2 |
| | 100 µg/ml | 38.2 |
| | 300 µg/ml | 50.4 |
| 21 | 66.7 µg/ml | 97.7 |
| (*Gambir*) | 80 µg/ml | 81.0 |
| | 100 µg/ml | 78.0 |
| | 120 µg/ml | 86.4 |
| | 200 µg/ml | 88.4 |
| | 300 ug/ml | 88.4 |

Example 31

Effect of Peppermint Extract on Ex Vivo GAG Release

Rabbit cartilage explants were cultured with rhIL-1α (5 ng/ml) in the absence or presence of Peppermint extract from Examples 25 and 26 to examine the protective effects on PG degradation.

TABLE 15

Effect of Peppermint Extracts on Ex Vivo GAG Release

| Sample | Dose | % GAG release |
|---|---|---|
| Normal | — | 34.5 |
| IL-1α | 5 ng/ml | 100 |
| Diclofenac | 300 µg/ml | 22.6 |
| 191-8 | 150 µg/ml | 110.9 |
| | 250 µg/ml | 84.1 |
| | 500 µg/ml | 73.0 |
| 622-9 | 150 µg/ml | 91.5 |
| | 250 µg/ml | 79.2 |
| | 500 µg/ml | 68.7 |

Peppermint extract inhibited rhIL-1α-mediated degradation of PG in a concentration dependent manner, although the effect of Peppermint extracts on PG degradation were weaker than the diclofenac treated group.

Example 32

Effect of N-Acetyl Glucosamine (Nag) on Ex Vivo GAG Release

Rabbit cartilage explants were cultured with rhIL-1α (5 ng/ml) in the absence or presence of NAG to examine the protective effects on PG degradation. NAG reduced rhIL-1α-mediated degradation of PG in a concentration dependent manner. However, the effects from NAG are marginal on the PG degradation when compared to the diclofenac treated group.

TABLE 16

Effect of N-Acetyl glucosamin on the Ex Vivo GAG releasing model

| Sample | Dose | % GAG release |
|---|---|---|
| Normal | — | 40.7 |
| IL-1α | 5 ng/ml | 100.0 |
| Diclofenac | 300 µg/ml | 30.1 |
| NAG | 25 µg/ml | 95.7 |
| | 50 µg/ml | 99.2 |
| | 100 µg/ml | 87.5 |
| | 150 µg/ml | 81.2 |

Example 33

Effect of *Curcuma longa* (C):*Morus* (M) Compositions on Ex Vivo GAG Release

Rabbit cartilage explants were cultured for 24 hr with rhIL-1α (5 ng/ml) in the absence or presence of a mixture of *Curcuma* and *Morus* extracts to examine the protective effects on PG degradation. The plant extracts from *Morus* and *Curcuma* were produced according Examples 10 and 19, respectively. *Curcuma* and *Morus* extracts were combined at different ratios, including 4:1, 2:1, 1:1, 1:2 and 1:4, respectively. The compositions were tested at four doses—50, 100, 200 and 300 µg/ml. As shown in Table 17, all compositions of plant extracts prevented rhIL-1α mediated degradation of articular cartilage in a concentration dependent manner.

TABLE 17

Effect of *Morus*/*Curcuma* Compositions on Ex Vivo GAG Release

| Sample | Dose (µg/ml) | % GAG release |
|---|---|---|
| (—) | — | 51.9 |
| IL-1α | 0.005 | 100.0 |
| Diclofenac | 300 | 36.8 |
| 4C:1M | 50 | 80.5 |
| | 100 | 58.1 |
| | 200 | 49.1 |
| | 300 | 61.8 |
| 2C:1M | 50 | 82.0 |
| | 100 | 57.5 |
| | 200 | 47.4 |
| | 300 | 68.4 |
| 1C:1M | 50 | 88.7 |
| | 100 | 62.0 |
| | 200 | 54.2 |
| | 300 | 59.7 |
| 1C:2M | 50 | 81.6 |
| | 100 | 59.5 |
| | 200 | 58.0 |
| | 300 | 57.2 |
| 1C:4M | 50 | 62.6 |
| | 100 | 63.3 |
| | 200 | 56.7 |
| | 300 | 32.7 |

Example 34

Evaluation of *Curcuma* (C):*Morus* (M) Composition Synergy on Ex Vivo GAG Release Rabbit cartilage explants were cultured for 24 hr with rhIL-1α (5 ng/ml) in the absence or presence of compositions of *Curcuma* extract, *Morus* extract, or a mixture thereof to examine the presence of a protective effect on PG degradation. The plant extracts from *Morus* and *Curcuma* were produced according Examples 10 and 19, respectively. *Curcuma* and *Morus* extracts were combined at different ratios, including 1:2 and 1:4. The compositions were tested at two doses—200 and 300 µg/ml, or at one dose—75 µg/ml to examine whether the combined extracts worked synergistically or additively. The individual extract compositions were tested at concentrations that were in proportion to the weight content of those extracts in the mixed composition.

TABLE 18

Synergistic Effect of C:M Composition versus C or M Alone

| Cmpsn | µg/ml | % Inhibition | Cmpsn | µg/ml | % Inhibition | Remark |
|---|---|---|---|---|---|---|
| 1C:4M | 200 | 85.1 | 1C:4M | 300 | 97.8 | Theoretical value |
| 1C:4M | 200 | 87.8 | 1C:4M | 300 | 100 | Experimental result |
| C | 40 | 49.1 | C | 60 | 72.6 | Individual |
| M | 160 | 70.7 | M | 240 | 92 | Individual |
| 1C:2M | 200 | 81.7 | 1C:2M | 300 | 95.6 | Theoretical value |
| 1C:2M | 200 | 95.8 | 1C:2M | 300 | 100 | Experimental result |
| C | 66.7 | 59.9 | C | 100 | 85 | Individual |
| M | 133.3 | 54.3 | M | 200 | 70.6 | Individual |
| 1C:1M | 75 | 53 | | | | Theoretical value |
| 1C:1M | 75 | 57.5 | | | | Experimental result |
| C | 37.5 | 33 | | | | Individual |
| M | 37.5 | 29.9 | | | | Individual |

Compositions of *Curcuma* and *Morus* extracts interfered with the rhIL-1α-mediated degradation of PG in a concentration dependent and synergistic manner. Especially, compositions 1C:4M (5 wt % curcuminoids, 2.4 wt % prenylated flavonoids, 2.4 wt % stilbenes) and 1C:2M (8.3 wt % curcuminoids, 2 wt % prenylated flavonoids, 2 wt % stilbenes) showed a synergistic effect at 200 and 300 µg/ml. Composition 1C:1M (12.5 wt % curcuminoids, 1.5 wt % prenylated flavonoids, 1.5 wt % stilbenes) also showed a synergistic effect at 75 µg/ml. Synergyvalues were calculated by using the COLBY formular (Colby, Weeds 15:20, 1967).

Example 35

Effect of *Curcuma* (C):*Morus* (M):N-Acetyl Glucosamin (NAG) Compositions on Ex Vivo GAG Release Rabbit cartilage explants were cultured for 24 hr with rhIL-1α (5 ng/ml) in absence or presence of composition of *Curcuma* and *Morus* extract to examine the protective effects on PG degradation. The plant extracts from *Morus* and *Curcuma* were produced according to Examples 10 and 19, respectively. *Curcuma* and *Morus* extracts were combined with N-Acetyl Glucosamine (NAG) at a ratio 1C:1M:2NAG. The compositions were tested at four doses-50, 100, 200 and 300 µg/ml. The individual extracts in the compositions were tested at concentrations that were in proportions of the weight contents of those extracts in the compositions. Synergy values were calculated by using the Colby formular (Colby, Weeds 15:20, 1967).

TABLE 19

Effect of *Curcuma*, *Morus*, and NAG Compositions

| Sample | Dose | % GAG release |
|---|---|---|
| Normal | — | 40.7 |
| IL-1α | 5 ng/ml | 100.0 |
| Diclofenac | 300 µg/ml | 30.1 |
| 1C:1M:2NAG | 50 µg/ml | 83.2 |
| | 100 µg/ml | 59.7 |
| | 200 µg/ml | 52.7 |
| | 300 µg/ml | 46.4 |
| *Curcuma* | 12.5 µg/ml | 71.8 |
| | 25 µg/ml | 74.9 |
| | 50 µg/ml | 50.8 |
| | 75 µg/ml | 58.4 |
| *Morus* | 12.5 µg/ml | 76.3 |
| | 25 µg/ml | 77.7 |
| | 50 µg/ml | 70.9 |
| | 75 µg/ml | 70.9 |
| NAG | 25 µg/ml | 95.7 |
| | 50 µg/ml | 99.2 |
| | 100 µg/ml | 87.5 |
| | 150 µg/ml | 81.2 |

As shown in the Table 19, the composition of plant extracts prevented with the rhIL-1α mediated degradation of articular cartilage in a concentration dependent manner. In particular, a 1C:1M:2NAG composition showed an unexpected synergistic effect at 300 µg/ml as compared to the three individual extracts alone (Table 20).

TABLE 20

Synergistic Effect of C:M:NAG Compositions

| Sample | Dose | % Inhibition | Remark |
|---|---|---|---|
| 1C:1M:2NAG | 300 µg/ml | 89.6 | Theoretical value |
| 1C:1M:2NAG | 300 µg/ml | 90.5 | Experimental result |
| C | 75 µg/ml | 70.1 | Individual |
| M | 75 µg/ml | 49.2 | Individual |
| NAG | 150 µg/ml | 31.8 | Individual |

Example 36

Effect of *Curcuma* (C):*Morus* (M):Peppermint (P) Compositions on Ex Vivo GAG Release Rabbit cartilage explants were cultured for 24 hr with rhIL-1α (5 ng/ml) in absence or presence of composition of *Curcuma* and *Morus* extract to examine the protective effects on PG degradation. The plant extracts from *Morus*, *Curcuma*, and Peppermint were produced according Examples 10, 19, and 24, respectively. *Curcuma*, *Morus*, and Peppermint extracts were combined at ratios of 1C:1M:0.5P, 1C:1M:1P, 1C:1M:1.5P, and 1C:1M:2P. The compositions were tested at four doses—50, 100, 200 and 300 µg/ml.

TABLE 21

Effect of C:M:P Compositions on Ex Vivo GAG Release

| Sample | Dose (µg/ml) | % GAG release |
|---|---|---|
| (—) | — | 39.5 |
| IL-1a | 0.005 | 100.0 |
| Diclofenac | 300 | 34.9 |
| 1C:1M:0.5P | 50 | 77.5 |
| | 100 | 67.1 |
| | 200 | 67.9 |
| | 300 | 39.2 |

TABLE 21-continued

Effect of C:M:P Compositions on Ex Vivo GAG Release

| Sample | Dose (µg/ml) | % GAG release |
|---|---|---|
| 1C:1M:1P | 50 | 76.7 |
| | 100 | 65.0 |
| | 200 | 51.7 |
| | 300 | 47.8 |
| 1C:1M:1.5P | 50 | 90.8 |
| | 100 | 90.6 |
| | 200 | 57.3 |
| | 300 | 49.1 |
| 1C:1M:2P | 50 | 105.2 |
| | 100 | 81.5 |
| | 200 | 64.3 |
| | 300 | 54.2 |

As shown in Table 21, all compositions of plant extracts prevented rhIL-1α induced degradation of articular cartilage in a concentration dependent manner.

Example 37

Animal Care and Housing

Animals were acclimated upon arrival for a week before being assigned randomly to their respective groups. CD-1 mice (5/cage) and Lewis rats (3/cage) were housed in a polypropylene cage and individually identified by numbers on their tail. Each cage was covered with wire bar lid and filtered top (Allentown, N.J.). Individual cage was identified with a cage card indicating project number, test article, dose level, group, and an animal number. The Harlan T7087 soft cob beddings was used and changed at least twice weekly. Animals were provided with fresh water and rodent chow diet #T2018 (Harlan Teklad, 370W, Kent, Wash.) ad libitum and were housed in a temperature controlled room (22.2° C.) on a 12 hour light-dark cycle. All animal experiments were conducted according to institutional guidelines congruent with guide for the care and use of laboratory animals.

Example 38

In Vivo Nociceptive Behavior Model Elicited by Intraplantar Injection of Formalin Mice (n=6 per group) were habituated under inverted Plexiglas observation chamber for 30 minutes to allow them to acclimatize to their surroundings. Animals were treated orally with respective treatment group 30 minutes before intraplantar injection of formalin (20 µl of 2.5% solution) into the right hind paw of restrained mice using a Hamilton syringe (Hamilton Company, Reno, Nev.) (Dubuisson et al., Pain 4:161, 1977). Mice were immediately transferred to their individual observational chamber. The duration of time spent flinching and/or licking of the inflamed hind paw was monitored and recorded over a period of 40 minutes in 10 minute time blocks. Mirrors positioned behind the chambers enabled observation of the right hind paw when it was obscured from direct view.

Example 39

Visceral Pain Perception Model (Writhing's Test)

Mice (n=6 per group) were habituated under an inverted Plexiglas observation chamber for 30 minutes to allow them to acclimatize to their surroundings. Animals were orally administered treatment articles at different doses, 100 mg/kg of ibuprofen, or vehicle control (propylene glycol) 30 minutes before intraperitoneal administration of freshly made acetic acid solution (0.7% in 0.9% NaCl) at 10 ml/kg using a 26 gauge needle. The experiment was carried out at room temperature. After the challenge, each animal was placed back into its own individual section of the observation chamber and the number of constrictions of the abdominal muscle together with stretching was counted cumulatively over a period of 30 minutes (Collier et al., Br. J. Pharmacol. Chemother. 32:295, 1968).

Example 40

Carrageenan-Induced Rat Paw Edema Model

Local inflammation was induced by intraplantar injection of carrageenan λ (Sigma, St. Louis, Mo.; 100 µl of 1% [w/v] in saline) into the plantar surface of right hind paw of sedated rat (with 2.5% isoflurane) at time 0 (T=0) (Gamache et al., J Neurosurg. 65:679, 1986; Guay et al., J. Biol. Chem. 279:24866, 2004; Chou et al., Anesth. Analg. 97:1724, 2003). Rats were acclimated in a procedure room for 20-30 minutes before each measurement was taken. Allodynia was evaluated by measuring responsiveness to the tip of a Randell-Selitto paw pressure test applied perpendicular to the central plantar surface of the right hind paw. A positive response to the applied pressure, noted by sharp withdrawal of the paw, was recorded automatically by an electronic Von Frey Anesthesiometer (2390 series Electrovonfrey, IITC, Woodland Hills, Calif.) (Vivancos et al., Braz. J. Med. Biol. Res. 37:391, 2004). Mechanical allodynia was evaluated before carrageenan inoculation, and thereafter at 1 hr, 2 hr, 4 hr and 6 hr. Paw edema volume was measured with the use of Plethysmometer (IITC, Woodland Hills, Calif.; Model 520) at time 0 (before carrageenan), and then 1 hr, 2 hr, 4 hr, and 6 hr after carrageenan injection. Animals (N=5 per group) were orally gavaged with a positive control ibuprofen (Spectrum Chemical MFG, Gardena, Calif.) (100 or 200 mg/kg); test articles such as: extracts, and combinations of extracts at various doses from 100, 200, 300 to 400 mg/kg and vehicle control (propylene glycol) were given 1 hour after carrageenan inoculation unless specified otherwise.

Example 41

Effect of Purified Curcumin in Nociceptive Behavior Model

Intraplantar injection of formalin (2.5%) in CD-1 mice elicited a biphasic nociceptive response compromising flinching, leg raising, biting and licking of the injected paw. These behavioral reactions observed for the first five minutes are due to direct action of the irritant on sensory nerve endings where is believed to be as a result of inflammation in the later phase. In this study, greater than 50% reduction in pain perception were observed for animals treated with single oral dose of curcumin isolated from organic extract of Curcuma longa as prepared in Example 16 (Compound 11) or ibuprofen in the inflammatory phase (Table 22). Mice were treated with curcumin (50, 100, 150 or 200 mg/kg) or ibuprofen (200 mg/kg) orally half an hour before intraplantar formalin injection.

TABLE 22

Dose Related Iinhibition of Pain Sensitivity by Curcumin

| Rx groups: | Dose (mg/kg) | Pain Sensitivity 20-40 Minutes after Formalin Injection | |
|---|---|---|---|
| | | % ↓ vs. Vehicle | P-value |
| Ibuprofen | 200 | 63.5 | 0.03 |
| Curcumin | 200 | 74.6 | 0.01 |
| | 150 | 60.3 | 0.07 |
| | 100 | 52.5 | 0.24 |
| | 50 | 53.1 | 0.15 |

Dose related inhibition in pain sensitivity was observed for curcumin treated mice at a dose range of 200 mg/kg to 100 mg/kg. There was little to no difference in the level of pain inhibition between animals treated with curcumin at 50 mg/kg and 100 mg/kg. Pain inhibition at 200 mg/kg curcumin or ibuprofen was statistically significant (Table 22). Furthermore, greater pain inhibition was observed in mice treated with curcumin at 200 mg/kg (74.6%) than with ibuprofen at 200 mg/kg (63.5%).

Example 42

Effect of *Curcuma* Formulated in β-Cyclodextrin in Nociceptive Behavior Model

To increase absorption and maximize efficacy, *Curcuma* extract, prepared as described in Example 20, was formulated with β-cyclodextrin at various ratios and tested in an abdominal constriction assay. CD-1 mice (N=6) were treated (gavaged) with 50 mg/kg or 100 mg/kg of these formulations or ibuprofen (100 mg/kg) half an hour before intraperitoneal injection of acetic acid.

TABLE 23

Effect of *Curcuma* Compostions on Visceral Pain Sensitivity

| Formulation | Curcumin content | Total curcuminoid content | Dose (mg/kg) | % ↓ vs. Vehicle | P-values |
|---|---|---|---|---|---|
| Ibuprofen | — | — | 100 | 56.1 | 0 |
| 401 | 12.57% | 29.06% | 50 | 19.2 | 0.02 |
| | | | 100 | 38.2 | 0.001 |
| 203-1 | 6.69% | 14.74% | 50 | 27.9 | 0.01 |
| | | | 100 | 33.3 | 0.003 |
| 601 | 8.11% | 25.74% | 50 | 10.9 | 0.07 |
| | | | 100 | 24.9 | 0.02 |
| 403-1 | 4.46% | 13.40% | 50 | 9.0 | 0.44 |
| | | | 100 | 16.0 | 0.12 |
| 201 | 72.99% | 96.58% | 50 | 23.7 | 0.03 |
| | | | 100 | 28.1 | 0.001 |
| 101-1 | 9.68% | 12.50% | 50 | 26.9 | 0.07 |
| | | | 100 | 32.8 | 0.0005 |

Ibuprofen treated animals showed 56.1% reduction in pain sensitivity (Table 23). Other than formulation 403-1 (which has the lowest curcumin and total curcuminoid content), all other formulations showed statistically significant inhibition in visceral pain sensitivity (Table 23).

Example 43

Effect of *Mentha piperita* Extract in Nociceptive Behavior Model

Plants with historical anti-inflammatory usage were screened for their anti-pain activity using writhing's animal model. Among these extracts, mice treated with a single oral dose of peppermint plant (*Mentha piperita*) methanol extract ME, as described in the Example 26, showed 29.8% visceral pain inhibition when administered at 300 mg/kg in CD-1 mice. Following ethyl acetate fractionation, an enhanced, statistically significant inhibition (i.e., 47.2%) compared to the methanol extract was observed for peppermint fractions administered at 126 mg/kg (Table 24). Comparable inhibition was also observed for ibuprofen treated animals (i.e., 67.6%).

TABLE 24

Percent Inhibition of Visceral Pain Sensitivity by Peppermint Extracts

| Compound/Spp | Dose (mg/kg) | Fraction | Max % inhibition | P-value | Reproducibility |
|---|---|---|---|---|---|
| Ibuprofen | 100 | — | 67.6 | 0.00026 | Yes |
| *Mentha piperita* | 126 | EA | 47.2 | 0.0005 | Yes |
| | 300 | ME | 29.8 | 0.0895 | Yes |

CD-1 mice (N=6) were gaveged with ibuprofen (100 mg/kg) or peppermint (126 or 300 mg/kg) half an hour before acetic acid injection.

Example 44

In Vivo Efficacy of Peppermint Extracts in Carrageenan-Induced Rat Paw Edema Model Carrageenan-induced rat paw edema model was utilized to evaluate different grades of peppermint ethanol extracts described in Example 26, which were gavaged at 200 mg/kg one hour after disease induction. As seen in Table 25 activity of extract decreases proportionally as the percentage of ethanol used for extraction decreased. Maximum inhibition in pain and inflammation was observed when rats were gavaged with a 100% ethanol extract of peppermint at a dose of 200 mg/kg followed by 90%. As a result, the 90% ethanol extract was selected for subsequent use. These percentage reductions were statistically significant at each time point analyzed against vehicle control.

TABLE 25

Anti-Pain and Anti-Inflammatory Activity of Peppermint Extracts

| | Dose | | Percent change vs. Vehicle | | | | | |
|---|---|---|---|---|---|---|---|---|
| | | | Paw Edema | | | Pain sensitivity | | |
| Group | (mg/kg) | N | 1 hr | 3 hr | 5 hr | 1 hr | 3 hr | 5 hr |
| Ibuprofen | 200 | 5 | 43.5* | 58.0* | 50.3* | 55.6* | 62.7* | 44.6* |
| 100% Ethanol Extract | 200 | 5 | 27.5* | 49.5* | 37.6* | 33.8* | 43.4* | 36.3* |
| 90% Ethanol Extract | 200 | 5 | 26.6* | 45.1* | 36.0* | 28.9* | 41.4* | 33.3* |

TABLE 25-continued

Anti-Pain and Anti-Inflammatory Activity of Peppermint Extracts

| Group | Dose (mg/kg) | N | Percent change vs. Vehicle | | | | | |
|---|---|---|---|---|---|---|---|---|
| | | | Paw Edema | | | Pain sensitivity | | |
| | | | 1 hr | 3 hr | 5 hr | 1 hr | 3 hr | 5 hr |
| 70% Ethanol Extract | 200 | 5 | 31.7* | 25.9* | 12.1 | 24.6* | 32.3* | 21.0* |
| 30% Ethanol Extract | 200 | 5 | 32.8* | 27.9* | 18.6** | 24.1* | 40.6* | 16.5** |
| Peppermint-Water extract | 200 | 5 | 20.2* | 26.2* | 18.2** | 8.6 | 26.0* | 10.2** |

Data are presented as a percent change as compared to vehicle alone. Lewis rats (N = 5) were treated with ibuprofen (200 mg/kg), peppermint (200 mg/kg), or vehicle an hour after carrageenan inoculation.
*$P \leq 0.001$ vs vehicle.
**$P \leq 0.05$ vs vehicle.

Example 45

Efficacy of Rosmarinic Acid in Carrageenan-Induced Rat Paw Edema Model

Documenting efficacy from abdominal constriction assay and carrageenan-induced rat paw edema models, subsequent activity guided fractionation and compound isolation was carried out to determine the active marker compounds in a peppermint extract. Rosmarinic acid (RA) and eriocitrin were confirmed as the active markers of peppermint and tested at doses of 200 mg/kg and 100 mg/kg, respectively, in carrageenan-induced rat paw edema model. As shown in Table 26, RA showed 29.9%, 35.7% and 34.6% reductions, and eriocitrin showed 17.2%, 36.0% and 30.0% reductions in paw edema after 1, 3 and 5 hours of treatment, respectively. Similarly, RA showed 38.9%, 45.0% and 30.6% reductions and eriocitrin showed 20.4%, 36.4% and 25.2% reductions in pain sensitivity after 1, 3 and 5 hours of treatment, respectively. The positive control ibuprofen showed 39.5%, 50.4% and 46.6% reduction in paw edema and 55.1%, 701.3% and 50.8% reduction in pain sensitivity after 1, 3 and 5 hours of treatment, respectively (Table 26). The measured inhibition in pain and inflammation was statistically significant for both RA and eriocitrin at each time point examined except 1 hour after eriocitrin treatment.

TABLE 26

Analgesic and Anti-Inflammatory Activity of Compounds Purified from Peppermint MeOH Extract

| Group | Dose (mg/kg) | N | Percent change of vehicle | | | | | |
|---|---|---|---|---|---|---|---|---|
| | | | Paw Edema | | | Pain sensitivity | | |
| | | | 1 hr | 3 hr | 5 hr | 1 hr | 3 hr | 5 hr |
| Ibuprofen | 200 | 5 | 39.5* | 50.4* | 46.6* | 55.1* | 70.3* | 50.8* |
| RA | 200 | 5 | 29.9* | 35.7* | 34.6* | 38.9* | 45.0* | 30.6* |
| Eriocitrin | 100 | 5 | 17.2 | 36.0* | 30.0* | 20.4* | 36.4* | 25.2* |

Data are presented as a percent change as compared to vehicle alone. Lewis rats (N = 5) were treated with ibuprofen (200 mg/kg), rosmarinic acid (200 mg/kg), eriocitrin 100 mg/kg or vehicle an hour after carrageenan inoculation.
*$P \leq 0.001$ vs vehicle.

Example 46

In Vivo Dose Response Effect of Peppermint Extract in Carrageenan-Induced Rat Paw Edema Model To determine what dose would induce maximum inhibition in pain and inflammation, a dose-response curve was conducted using the carrageenan-induced rat paw edema model. Rats were gavaged with 90% ethanol extract of peppermint, made as described in Example 25, at dose ranging from 300 mg/kg to 50 mg/kg. As illustrated in Table 27, a correlation in pain and inflammation reduction was observed when rats were administered with peppermint at 200 mg/kg to 50 mg/kg. In this particular study, rats treated with 300 mg/kg of 90% ethanol extract peppermint didn't show greater inhibition than 200 mg/kg treated rats, probably due to issues associated with solubility of the higher dose.

TABLE 27

Analgesic and Anti-Inflammatory Activity of Peppermint Extract 25

| Group | Dose (mg/kg) | N | Percent Change of Vehicle | | | | | |
|---|---|---|---|---|---|---|---|---|
| | | | Inflammation | | | Analgesia | | |
| | | | 1 hr | 3 hr | 5 hr | 1 hr | 3 hr | 5 hr |
| Ibuprofen | 200 | 5 | 44.6* | 54.9* | 50.0* | 52.9* | 62.5* | 48.8* |
| 25 | 300 | 5 | 8.5 | 32.8* | 29.8* | 27.2* | 37.0* | 30.8* |
| 25 | 200 | 5 | 32.8* | 46.1* | 34.8* | 38.0* | 47.1* | 34.2* |
| 25 | 100 | 5 | 22.6* | 23.3* | 10.9 | 27.8* | 21.9* | 19.1** |
| 25 | 50 | 5 | 15.8** | 12.3 | 8.4 | 22.7* | 13.4** | 13.5** |

Data are presented as a percent change as compared to vehicle alone. Female Lewis rats (N = 5) were treated with ibuprofen (200 mg/kg) and 90% ethanol extract peppermint (300 mg/kg, 200 mg/kg, 100 mg/kg and 50 mg/kg), or vehicle an hour after carrageenan inoculation.
*$P \leq 0.001$ vs vehicle.
**$P \leq 0.05$ vs vehicle.

Example 47

Effect of Morus Extract on Nociceptive Behavior Model

Writhing's animal model was employed to evaluate anti-nociceptive activity of plant extracts of this disclosure. When CD-1 mice were treated with a single oral dose of 25, 50 or 300 mg/kg of ethanol extract of Morus alba from Example 11, 30.7%, 45.3% and 48.4%, respectively, visceral pain inhibition was observed as compared to vehicle treated CD-1 mice (Table 28).

TABLE 28

Percent inhibition of visceral pain sensitivity by Morus Extract

| Compound | Spp. | Part | Dose (mg/kg) | N | Mean ± SD | % Inhibition | P Value |
|---|---|---|---|---|---|---|---|
| Vehicle | | | 0 | 6 | 82.3 ± 24.3 | — | — |
| | | | 300 | 6 | 42.5 ± 10.2 | 48.4 | 0.004 |
| 11 | M. alba | Root bark | 50 | 6 | 45.0 ± 11.5 | 45.3 | 0.001 |
| | | | 25 | 6 | 57.2 ± 14.3 | 30.7 | 0.05 |

CD-1 mice (N = 6) were gaveged with vehicle (0 mg/kg) or Morus alba (25, 50 or 300 mg/kg) half an hour before acetic acid injection.

Example 48

Dose Response of Carrageenan-Induced Rat Paw Edema Model to Morus Extract

Analgesic and anti-inflammatory activity of Morus alba were also confirmed by using carrageenan induced rat paw edema model. Lewis rats (N=5) were orally gavaged with a dose of 100, 200, or 300 mg/kg of Morus ethanol extract 13-1, as described in Example 13, 1 hour after carrageenan inoculation. Ethanol extract of Morus were effective in both measures as low as 100 mg/kg. As depicted in Table 29, rats treated with 300 mg/kg showed the highest inhibition in pain (48.0%-31.6%) and inflammation (53.1%-37.0%) when compared to vehicle control. Similarly, a range of 45.8%-24.6% reduction in paw edema and 34.7%-22.1% reduction in pain were observed for rats treated with a dose of 200 mg/kg of Morus ethanol extract 13-1. These reductions were statistically significant at each time point examined.

TABLE 29

Analgesic and Anti-Inflammatory Activity of Morus Ethanol Extract 13-1

| | Dose | | Percent change of vehicle | | | | | |
| | (mg/ | | Paw edema | | | Pain sensitivity | | |
| Group | kg) | N | 1 hr | 3 hr | 5 hr | 1 hr | 3 hr | 5 hr |
|---|---|---|---|---|---|---|---|---|
| Ibuprofen | 200 | 5 | 53.2* | 64.3* | 50.6* | 57.1* | 61.5* | 44.3* |
| M. alba | 300 | 5 | 53.1* | 46.1* | 37.0* | 48.0* | 46.1* | 31.6* |
| 13-1 | 200 | 5 | 45.8* | 35.9* | 24.6* | 34.7* | 36.4* | 22.1* |
| | 100 | 5 | 16.6 | 18.3** | 12.3** | 20.3* | 31.2* | 6.3 |

Data are presented as a percent change as compared to vehicle alone. Female Lewis rats (N = 5) were treated with ibuprofen (200 mg/kg) and ethanol extract of M. alba 13-1 (300 mg/kg, 200 mg/kg, and 100 mg/kg), or vehicle alone an hour after carrageenan inoculation.
*P ≤ 0.001 vs vehicle.
**P ≤ 0.05 vs vehicle.

Example 49

Efficacy of Pure Compounds and Extracts of Morus in Carrageenan-Induced Rat Paw Edema Model Based on activity guided fractionation and compound isolation; four major actives, oxyresveratrol, mulberroside A, kuwanon G and morusin isolated from extract of Moms root bark as described in Examples 3 and 5, were evaluated in carrageenan-induced rat paw edema model for their in vivo activity. Animals were orally administered with purified Moms compounds at a dose of 100 mg/kg, one hour after carrageenan inoculation. In this study EtOAc fractions and ethanol extracts 11, 13-1 and 13-3 of Morusat a dose of 200 mg/kg were included. As seen in Table 30, all marker compounds showed statistically significant inhibition in pain and inflammation when compared to vehicle control. However, a sharp drop in percent inhibition was observed when extract with high active content extract 13-1 was compared to low active contents extract 13-3 in marker compounds. As a result, these data indicate that root bark Morus extracts having a high content of both stilbenes and prenylated flavonoids will likely result in maximum pain and inflammation inhibition.

TABLE 30

Analgesic and Anti-Inflammatory Activity of Morus Extracts and Compounds

| | Dose | | Percent change of vehicle | | | | | |
| | (mg/ | | Paw edema | | | Pain sensitivity | | |
| Group | kg) | N | 1 hr | 3 hr | 5 hr | 1 hr | 3 hr | 5 hr |
|---|---|---|---|---|---|---|---|---|
| Ibuprofen | 200 | 5 | 51.6* | 61.9* | 50.0* | 55.4* | 65.9* | 49.3* |
| Oxyresveratrol | 100 | 5 | 44.7* | 54.5* | 38.3* | 53.3* | 54.8* | 38.5* |
| Mulberroside A | 100 | 5 | 48.4* | 50.6* | 37.3* | 54.2* | 52.2* | 35.5* |
| Kuwanon G | 100 | 5 | 36.5* | 37.7* | 29.3* | 33.3* | 40.5* | 31.2* |
| Morusin | 100 | 5 | 37.3* | 40.0* | 38.0* | 33.3* | 38.5* | 30.2* |
| 13-1 | 200 | 5 | 37.1* | 36.1* | 33.9* | 36.0* | 41.1* | 30.6* |
| 13-3 | 200 | 5 | 21.1* | 24.9* | 23.1* | 24.2* | 26.7* | 18.4* |
| 11 | 200 | 5 | 27.0* | 32.9* | 31.7* | 31.2* | 35.5* | 19.7* |

Data are presented as a percent change as compared to vehicle alone. Female Lewis rats (N = 5) were treated with ibuprofen (200 mg/kg), marker compounds (100 mg/kg), 13-1 (Ethanol extract of M. alba at a dose of 200 mg/kg), 13-3 (M. alba supernatant at a dose of 200 mg/kg), 11 (EtOAc Fraction of Morus alba at a dose of 200 mg/kg) or vehicle an hour after carrageenan inoculation.
*P ≤ 0.001 vs vehicle.

Example 50

Efficacy of Morus:Curcuma Compositions on Carrageenan-Induced Rat Paw Edema Model Once analgesic and anti-inflammatory activity of Curcuma and Morus extracts were confirmed in multiple animal models, a study was designed to evaluate activity of a composition comprising a mixture of these two extracts. The plant extracts from Morus and Curcuma were produced according Examples 10 and 19, respectively. Curcuma and Morus extracts were combined at different ratios, including 4:1, 2:1, 1:1, 1:2 and 1:4. The compositions 1C:1M, 1C:2M, 2C:1M, 1C:4M and 4C:1M were administered orally at a dose of 300 mg/kg. As seen in Table 31, all compositions showed statistically significant inhibition of pain and inflammation at all-time points examined. Among them, rats gavaged with the composition combining Curcuma and Morus extracts at a ratio of 1:1 showed the maximum inhibition both in pain and inflammation, which is the composition that was selected for subsequent tests.

TABLE 31

Analgesic and Anti-Inflammatory Activity of C:M Compositions

| | Dose | | Percent change vs. Vehicle | | | | | |
|---|---|---|---|---|---|---|---|---|
| | (mg/ | | Paw edema | | | Pain sensitivity | | |
| Group | kg) | N | 1 hr | 3 hr | 5 hr | 1 hr | 3 hr | 5 hr |
| Ibuprofen | 200 | 5 | 53.9* | 59.0* | 52.6* | 56.4* | 62.2* | 45.0* |
| 1C:1M | 300 | 5 | 51.4* | 46.6* | 41.4* | 54.4* | 49.4* | 41.8* |
| 1C:2M | 300 | 5 | 57.6* | 45.3* | 41.1* | 56.5* | 48.6* | 39.5* |
| 2C:1M | 300 | 5 | 27.7* | 35.8* | 31.3* | 40.8* | 46.2* | 27.7* |
| 1C:4M | 300 | 5 | 50.1* | 33.7* | 27.8* | 46.5* | 40.7* | 25.6* |
| 4C:1M | 300 | 5 | 27.3* | 25.1* | 26.4* | 23.7* | 29.9* | 20.4** |

Data are presented as a percent change as compared to vehicle alone. Female Lewis rats (N = 5) were treated with ibuprofen (200 mg/kg) and composition C:M (300 mg/kg), or vehicle an hour after carrageenan inoculation.
*P ≤ 0.001 Vs vehicle.
**P ≤ 0.05 Vs vehicle.

Example 51

Dose Response of *Curcuma:Morus* Composition in Carrageenan-Induced Rat Paw Edema Model The *Curcuma:Morus*: composition with a blending ratio of 1C:1M was further subjected to a dose-response study to determine the dose that would result in the most significant inhibition in pain and inflammation. For this purpose, female Lewis rats (N=5) were gavaged orally a dose of 100, 200, 300 or 400 mg/kg of 1C:1M composition as described in Example 50, one hour after intraplantar carrageenan injection. Statistically significant, dose correlated, inhibition in pain and inflammation were observed for all doses administered, with the highest inhibition observed for the 400 mg/kg doise and the lowest inhibition for the 100 mg/kg dose of the 1C:1M composition.

TABLE 32

Analgesic and Anti-Inflammatory Activity of 1C:1M Composition

| | Dose | | Percent change of vehicle | | | | | |
|---|---|---|---|---|---|---|---|---|
| | (mg/ | | Paw edema | | | Pain sensitivity | | |
| Group | kg) | N | 1 hr | 3 hr | 5 hr | 1 hr | 3 hr | 5 hr |
| Ibuprofen | 200 | 5 | 53.9* | 59.0* | 52.6* | 56.4* | 62.2* | 45.0* |
| 1C:1M | 400 | 5 | 55.1* | 51.5* | 45.5* | 55.9* | 54.2* | 44.4* |
| 1C:1M | 300 | 5 | 51.4* | 46.6* | 41.4* | 54.4* | 49.4* | 41.8* |
| 1C:1M | 200 | 5 | 50.1* | 40.7* | 30.8* | 42.5* | 39.7* | 32.0* |
| 1C:1M | 100 | 5 | 35.6* | 28.0* | 22.6* | 21.7* | 30.2* | 10.4** |

Data are presented as a percent change as compared to vehicle alone. Female Lewis rats (n = 5) were treated with ibuprofen (200 mg/kg), composition 1C:1M (400 mg/kg, 300 mg/kg, 200 mg/kg or 100 mg/kg), or vehicle an hour after carrageenan inoculation.
*P ≤ 0.001 as compared to vehicle.

Example 52

Evaluation of *Morus:Curcuma* Composition Synergy in a Carrageenan-Induced Rat Paw Edema Model Carrageenan-induced paw edema model was used to evaluate a possible synergy or unexpected effect of the extracts from *Curcuma* and *Morus* when formulated together in a specific ratio of 1C:1M as described in Example 50, using Colby's method (Colby, 1967). Rats treated with the 1C:1M (12.5 wt % curcuminoids, 1.5 wt % prenylated flavonoids, 1.5 wt % stilbenes) composition at a dose of 300 mg/kg showed greater (synergistic) activity than the theoretically calculated (additive effect) for both inflammation and pain sensitivity at each time point analyzed (1, 3 or 5 hours after treatment). Similarly, the composition also showed a greater inhibition in pain sensitivity and inflammation than either *Curcuma* or *Morus* extract administered alone at the same dose of 300 mg/kg (see Tables 33 and 34).

TABLE 33

Analgesic and Anti-Inflammatory Activity of 1C: 1M Mixture

| | Dose | | Percent change of vehicle | | | | | |
|---|---|---|---|---|---|---|---|---|
| | (mg/ | | Paw edema | | | Pain sensitivity | | |
| Group | kg) | N | 1 hr | 3 hr | 5 hr | 1 hr | 3 hr | 5 hr |
| Ibuprofen | 200 | 5 | 53.9* | 59.0* | 52.6* | 56.4* | 62.2* | 45.0* |
| 1C:1M (50) | 300 | 5 | 51.4* | 46.6* | 41.4* | 54.4* | 49.4* | 41.8* |
| M. alba (10) | 300 | 5 | 45.1* | 38.3* | 31.3* | 44.6* | 39.2* | 32.5* |
| M. alba (10) | 150 | 5 | 31.4* | 26.2* | 18.3* | 31.3* | 27.0* | 24.0* |
| C. longa (19) | 300 | 5 | 41.8* | 35.3* | 29.2* | 39.0* | 44.7* | 30.9* |
| C. longa (19) | 150 | 5 | 27.7* | 24.3* | 21.5* | 25.0* | 30.5* | 21.4* |

Data are presented as a percent change as compared to vehicle alone. Female Lewis rats (N = 5) were treated with ibuprofen (200 mg/kg), composition 1C:1M (300 mg/kg), *Morus alba* extract (150 mg/kg or 300 mg/kg), *Curcuma longa* extract (150 mg/kg or 300 mg/kg) or vehicle an hour after carrageenan inoculation.
*P ≤ 0.001 vs vehicle.

TABLE 34

Analgesic and Anti-Inflammatory Activity of 1C:1M Mixture

| | | Dose | | Percent change vs Vehicle | | | | | |
|---|---|---|---|---|---|---|---|---|---|
| | | | | Paw Edema | | | Pain Sensitivity | | |
| Composition/ Compound* | Synergy | mg/ kg | N | 1 hr | 3 hr | 5 hr | 1 hr | 3 hr | 5 hr |
| 1C | — | 150 | 5 | 27.7 | 24.3 | 21.5 | 25.0 | 30.5 | 21.4 |
| 1M | — | 150 | 5 | 31.4 | 26.2 | 18.3 | 31.3 | 27.0 | 24.0 |

TABLE 34-continued

Analgesic and Anti-Inflammatory Activity of 1C:1M Mixture

| Composition/ | | Dose | | Percent change vs Vehicle | | | | | |
|---|---|---|---|---|---|---|---|---|---|
| | | mg/ | | Paw Edema | | | Pain Sensitivity | | |
| Compound* | Synergy | kg | N | 1 hr | 3 hr | 5 hr | 1 hr | 3 hr | 5 hr |
| 1C:1M | Expected** | — | — | 50.4 | 44.1 | 35.9 | 48.5 | 49.2 | 40.3 |
| | Observed¥ | 300 | 5 | 51.4 | 46.6 | 41.4 | 54.4 | 49.4 | 41.8 |

Data are presented as a percent change as compared to vehicle alone. Rats (n = 5) were gavaged with composition 1C:1M (300 mg/kg), Curcuma and Morus extracts (150 mg/kg), and vehicle alone 1 hour after carrageenan induced paw edema induction.
*C—Curcuma; M—Morus.
**Expected—Calculated value according to Colby's method = A − B i.e A = (C + M), B = (CM)/100.
¥Observed—data observed when a composition was orally administered at 300 mg/kg.

Example 53

Efficacy of Morus:Curcuma:Peppermint Compositions in Carrageenan-Induced Rat Paw Edema Model The efficacy of composition 1C:1M with a peppermint extractadded was examined for increased efficacy. The effective dose of 1C1M was set at 200 mg/kg and Peppermint extract 24 was added at a dose of 50, 100, 150 or 200 mg/kg to result in ratios of 1C:1M:0.5P, 1C:1M:1P, 1C:1M:1.5P and 1C:1M:2P, respectively. A direct correlation in response was observed for analgesic and anti-inflammatory activity of the composition when the proportion of added Peppermint extract 24 increased from 50 mg/kg to 200 mg/kg. The highest inhibition was observed for 1C:1M:2P, while the lowest was recorded for 1C:1M:0.5P. Nonetheless, all of compositions 1C:1M:0.5P, 1C:1M:1P, 1C:1M:1.5P and 1C:1M:2P showed a higher efficacy than 1C:1M (Table 35).

TABLE 35

Analgesic and Anti-Inflammatory Activity of C:M:P and C:M Compositions

| | Dose | | Percent change of vehicle | | | | | |
|---|---|---|---|---|---|---|---|---|
| | (mg/ | | Paw edema | | | Pain sensitivity | | |
| Group | kg) | N | 1 hr | 3 hr | 5 hr | 1 hr | 3 hr | 5 hr |
| Ibuprofen | 200 | 5 | 57.2* | 67.6* | 53.5* | 56.1* | 65.9* | 47.9* |
| 1C:1M:2P | 400 | 5 | 50.6* | 47.5* | 43.5* | 52.5* | 51.2* | 40.3* |
| 1C:1M:1.5P | 350 | 5 | 47.3* | 42.6* | 38.4* | 48.3* | 45.9* | 35.9* |
| 1C:1M:1P | 300 | 5 | 45.3* | 40.8* | 31.2* | 43.9* | 44.4* | 31.7* |
| 1C:1M:0.5P | 250 | 5 | 42.4* | 37.8* | 24.2* | 43.3* | 40.2* | 30.9* |
| 1C:1M | 200 | 5 | 37.9* | 35.4* | 23.1* | 42.1* | 38.0* | 30.2* |

Data are presented as a percent change as compared to vehicle alone. Female Lewis rats (N = 5) were treated with ibuprofen (200 mg/kg), composition 1C1M0.5P (250 mg/kg), 1C1M1P (300 mg/kg), 1C1M1.5P (350 mg/kg), 1C:1M:2P (400 mg/kg), 1C:1M (200 mg/kg) or vehicle an hour after carrageenan inoculation.
*P ≤ 0.001 vs vehicle

Example 54

Efficacy of Morus:Curcuma:N-Acetylglucosamine (Nag) Composition in Carrageenan-Induced Rat Paw Edema Model N-acetylglucosamine (NAG) is the building block of collagen in the joint. By adding NAG into Morus and Curcuma composition 1C:1M, it may be possible to enhance the joint care benefit without changing the anti-inflammatory and anti-pain activity of the C:M composition. To examine this hypothesis, a study was performed using carrageenan-induced rat paw edema as the disease model. In this study, rats were orally treated with 1C:1M at a dose of 200 mg/kg or an equivalent dose of 3C:3M:5NAG at a dose of 366 mg/kg one hour after disease induction. NAG alone at 166 mg/kg was included in this study. As shown in Table 36, NAG neither enhances nor inhibits analgesic and anti-inflammatory activity of the CM composition in this model. At least in this animal model, it could be concluded that NAG has minimal to no activity in inhibiting pain or inflammation at a dose of 166 mg/kg.

TABLE 36

Analgesic and Anti-Inflammatory Activity of a C:M:NAG Composition

| | Dose | | Percent change of vehicle | | | | | |
|---|---|---|---|---|---|---|---|---|
| | (mg/ | | Paw edema | | | Pain sensitivity | | |
| Group | kg) | N | 1 hr | 3 hr | 5 hr | 1 hr | 3 hr | 5 hr |
| Ibuprofen | 200 | 5 | 57.2* | 67.6* | 53.5* | 56.1* | 65.9* | 47.9* |
| 1C:1M | 200 | 5 | 37.9* | 35.4* | 23.1* | 42.1* | 38.0* | 30.2* |
| 3C:3M:5NAG | 366 | 5 | 40.3* | 34.6* | 27.7* | 42.1* | 37.4* | 30.6* |
| NAG | 166 | 5 | 8.2 | 15.8 | 6.2 | 8.8 | 3.6 | 2.6 |

Data are presented as a percent change as compared to vehicle alone. Female Lewis rats (n = 5) were treated with ibuprofen (200 mg/kg), composition 1C1M (200 mg/kg), 3C:3M:5NAG (366 mg/kg), NAG (166 mg/kg) or vehicle alone an hour after carrageenan inoculation.
*P ≤ 0.001 vs vehicle

Examples 55

Dose Response of Morus:Curcuma:NAG Composition in Carrageenan-Induced Rat Paw Edema Model To further examine whether N-acetylglucosamine (NAG) had a neutral effect on composition CM efficacy, a dose-response study was designed for 1C:1M:2NAG at oral doses of 600, 500, 400 and 300 mg/kg in carrageenan-induced rat paw edema model. Rats were gavaged the composition one hour after intraplantar carrageenan inoculation. These dosages correlate with doses of 300, 250, 200 and 150 mg/kg of 1C1M, respectively. As seen in Table 37, all compositions showed statistically significant inhibition in pain and inflammation, the highest being in the 600 mg/kg and the lowest in 300 mg/kg. These data again show that NAG neither enhances nor inhibits the analgesic and anti-inflammatory activity of the mixed Curcuma:Morus composition.

TABLE 37

Analgesic and Anti-Inflammatory Efficacy
of 1C:1M:2NAG Composition

| Group | Dose (mg/kg) | N | Percent change of vehicle | | | | | |
|---|---|---|---|---|---|---|---|---|
| | | | Paw edema | | | Pain sensitivity | | |
| | | | 1 hr | 3 hr | 5 hr | 1 hr | 3 hr | 5 hr |
| Ibuprofen | 200 | 5 | 54.2* | 57.7* | 48.6* | 53.7* | 61.5* | 47.5* |
| 1C1M2NAG | 600 | 5 | 55.7* | 48.1* | 43.4* | 56.1* | 52.2* | 43.6* |
| 1C1M2NAG | 500 | 5 | 53.4* | 47.5* | 41.3* | 54.3* | 50.3* | 41.6* |
| 1C1M2NAG | 400 | 5 | 42.2* | 43.6* | 36.6* | 46.9* | 42.8* | 35.3* |
| 1C1M2NAG | 300 | 5 | 33.7* | 31.0* | 28.1* | 33.6* | 37.2* | 27.3* |

Data are presented as a percent change as compared to vehicle alone. Female Lewis rats (N = 5) were treated with ibuprofen (200 mg/kg), composition 1C:1M:2NAG (600, 500, 400 or 300 mg/kg), or vehicle an hour after carrageenan inoculation.
*P ≤ 0.001 vs vehicle Example 56

Efficacy of *Morus:Curcuma*:NAG Composition in Writhing Test

Composition 1C:1M:2NAG was further tested at doses of 600 mg/kg, 500 mg/kg and 400 mg/kg for capability to alleviate visceral pain inflicted by intraperitoneal administration of acetic acid in CD-1 mice. In this study, 1C:1M (without NAG) and NAG (N-acetylglucosamine) alone at a dose of 300 mg/kg were used as controls. Immediately after injection of the irritant, animals showed abdominal constrictions consisting of contractions of the abdominal muscle which progressed posteriorly and ended with simultaneous flexor extension of both hind limbs with arching of the back.

TABLE 38

Effect of 1C:1M:2NAG Composition on Visceral Pain Sensitivity

| Groups | Dose (mg/kg) | Mean + SD | % change | P-values |
|---|---|---|---|---|
| Vehicle | 0 | 96.2 ± 16.3 | — | — |
| Ibuprofen | 200 | 34.5 ± 12.7 | 64.1 | 0.0000 |
| 1C:1M | 300 | 51.5 ± 7.9 | 46.4 | 0.0001 |
| NAG | 300 | 91.0 ± 18.7 | 5.4 | 0.6210 |
| 1C:1M:2NAG | 600 | 50.8 ± 7.8 | 47.1 | 0.0001 |
| 1C:1M:2NAG | 500 | 64.5 ± 10.8 | 32.9 | 0.0027 |
| 1C:1M:2NAG | 400 | 76.8 ± 12.4 | 20.1 | 0.0432 |

CD-1 mice (N = 6) were gavaged with ibuprofen (200 mg/kg), 1C:1M:2NAG (600, 500 or 400 mg/kg), 1C:1M (300 mg/kg), N-acetylglucosamine (NAG, 300 mg/kg) or vehicle alone half an hour before acetic acid injection.

The number of behavioral responses observed for 30 minutes were reduced to 50.8±7.9, 64.5±7.8 and 76.8±12.4 for 1C:1M:2NAG after oral administration at doses of 600, 500 and 400 mg/kg, respectively, as compared to the vehicle control, i.e., 96.2±16.3 (Table 53). A similar response of 51.5±7.9 was observed for mice treated with 300 mg/kg of 1C:1M (Table 53). However, mice receiving NAG alone showed 91.0+18.7 behavioral reaction. This finding indicates that 1C:1M:2NAG provides an analgesic effect in a dose dependent manner, and that 1C:1M is the active component in C:M:NAG composition, while NAG has minimal to neutral effect on analgesic activity of 1C:1M in this model.

Example 57

Efficacy of *Morus:Uncaria* Compositions in Carrageenan-Induced Rat Paw Edema Model

*Morus alba* ethanol extract 10 (M), as described in Example 10, was formulated with *Uncaria gambir* extract 21 (G), as described in Example 21, at ratios of 1G:1M, 1G:2M, 1G:4M, 2G:1M (13.3 wt % flavans, 1 wt % prenylated flavonoids, 1 wt % stilbenes) and 4G:1M (16 wt % flavans, 0.6 wt % prenylated flavonoids, 0.6 wt % stilbenes) and tested in carrageenan-induced rat paw edema model at a dose of 300 mg/kg. For comparison, each constituent extract, *Uncaria* and *Morus*, were each administered orally at dose of 300 mg/kg. As seen in Table 39, all treatment groups (ratios and individual components) showed statistically significant inhibition in pain and inflammation when compared to vehicle control. But, unexpected enhanced (synergistic) activity was observed for ratios of 1G:1M (10 wt % flavans, 1.5 wt % prenylated flavonoids, 1.5 wt % stilbenes), 1G:2M (about 6.7 wt % flavans, 2 wt % prenylated flavonoids, 2 wt % stilbenes) and 1G:4M (4 wt % flavans, 2.4 wt % prenylated flavonoids, 2.4 wt % stilbenes) as compared to either *Uncaria* or *Morus* given alone at the same dose of 300 mg/kg.

TABLE 39

Analgesic and Anti-Inflammatory Activity
of GM Compositions Compared to "G"
Extract 21 and "M" Extract 10

| Group | Dose (mg/kg) | N | Percent change vs Vehicle | | | | | |
|---|---|---|---|---|---|---|---|---|
| | | | Paw edema | | | Pain sensitivity | | |
| | | | 1 hr | 3 hr | 5 hr | 1 hr | 3 hr | 5 hr |
| Ibuprofen | 200 | 5 | 53.0* | 60.1* | 51.3* | 52.4* | 59.7* | 43.3* |
| 1G:1M | 300 | 5 | 50.2* | 53.3* | 48.7* | 51.8* | 52.5* | 40.0* |
| 1G:2M | 300 | 5 | 48.6* | 51.4* | 48.4* | 47.0* | 49.1* | 38.7* |
| 1G:4M | 300 | 5 | 43.4* | 50.8* | 39.4* | 42.9* | 44.7* | 33.2* |
| 2G:1M | 300 | 5 | 31.1* | 42.7* | 27.1* | 36.6* | 42.8* | 28.8* |
| 4G:1M | 300 | 5 | 32.3* | 41.7* | 20.9* | 33.7* | 36.7* | 21.1* |
| G (*Gambir*) | 300 | 5 | 28.7* | 34.3* | 17.4* | 33.9* | 30.9* | 17.5* |
| M (*Morus*) | 300 | 5 | 38.2* | 43.9* | 31.4* | 38.9* | 37.1* | 30.7* |

Data are presented as a percent change as compared to vehicle. Female Lewis rats (N = 5) were treated with ibuprofen (200 mg/kg), composition G:M (300 mg/kg), *Morus alba* (300 mg/kg), *Uncaria gambir* (300 mg/kg) or vehicle an hour after carrageenan inoculation.
*P ≤ 0.001 vs vehicle Example 58

Efficacy of *Morus:Acacia* Compositions in Carrageenan-Induced Rat Paw Edema Model Compositions comprising extract 22 from *Acacia catechu*, as described in Example 22, and *Morus alba* ethanol extract 10, as described in Example 10, were tested at ratios of 1A:1M, 1A:2M, 1A:4M (4 wt % flavans, 2.4 wt % prenylated flavonoids, 2.4 wt % stilbenes), 2A:1M (13.3 wt % flavans, 1 wt % prenylated flavonoids, 1 wt % stilbenes) and 4A:1M (16 wt % flavans, 0.5 wt % prenylated flavonoids, 0.5 wt % stilbenes) in carrageenan-induced rat paw edema model at a dose of 300 mg/kg. For comparison, extract from each constituent, *A. catechu* extract 22 and *M. alba* extract 10 were each individually administered orally at dose of 300 mg/kg. As seen in Table 40, all treatment groups (ratios and individual components) showed statistically significant inhibition in pain and inflammation when compared to vehicle control. However, unexpected enhanced activities were observed for ratios 1A:1M (10 wt % flavans, 1.5 wt % prenylated flavonoids, 1.5 wt % stilbenes) and 1A:2M (6.7 wt % flavans, 2 wt % prenylated flavonoids, 2 wt % stilbenes as compared to either *A. catechu* extract 22 or *M. alba* extract 10 given alone at the same dose of 300 mg/kg.

TABLE 40

Analgesic and Anti-Inflammatory Activity of A:M Compositions Compared to "A" Extract 22 and "M" Extract 10

| Group | Dose (mg/kg) | N | Percent change vs Vehicle |||||| 
|---|---|---|---|---|---|---|---|---|
| | | | Paw edema ||| Pain sensitivity |||
| | | | 1 hr | 3 hr | 5 hr | 1 hr | 3 hr | 5 hr |
| Ibuprofen | 200 | 5 | 53.0* | 60.1* | 51.3* | 52.4* | 59.7* | 43.3* |
| 1A:1M | 300 | 5 | 41.8* | 44.5* | 38.6* | 46.3* | 47.3* | 33.2* |
| 1A:2M | 300 | 5 | 55.4* | 49.2* | 43.0* | 51.4* | 48.4* | 36.6* |
| 1A:4M | 300 | 5 | 32.7* | 46.4* | 37.9* | 40.9* | 46.4* | 32.3* |
| 2A:1M | 300 | 5 | 41.4* | 36.8* | 22.7* | 46.5* | 44.2* | 27.6* |
| 4A:1M | 300 | 5 | 32.7* | 34.6* | 20.6* | 36.6* | 41.0* | 21.5* |
| A (*Acacia*) | 300 | 5 | 35.5* | 29.3* | 17.3* | 35.0* | 31.1* | 17.7* |
| M (*Morus*) | 300 | 5 | 38.2* | 43.9* | 31.4* | 38.9* | 37.1* | 30.7* |

Data are presented as a percent change as compared to vehicle alone. Female Lewis rats (N = 5) were treated with ibuprofen (200 mg/kg), composition A:M (300 mg/kg), *Morus alba* (300 mg/kg), *Acacia catechu* (300 mg/kg) or vehicle an hour after carrageenan inoculation.
*$P \leq 0.001$ vs vehicle.

TABLE 41

Dose correlated Analgesic and Anti-Inflammatory Activity of 1G:1M, 1A:2M and 1A:1M Compositions

| Group | Dose mg/kg | N | Percent change vs Vehicle ||||||
|---|---|---|---|---|---|---|---|---|
| | | | Paw Edema ||| Pain sensitivity |||
| | | | 1 hr | 3 hr | 5 hr | 1 hr | 3 hr | 5 hr |
| Ibuprofen | 200 | 5 | 52.5* | 62.9* | 51.6* | 58.6* | 64.0* | 50.7* |
| 1G:1M | 300 | 5 | 53.7* | 55.3* | 48.8* | 56.1* | 53.3* | 44.8* |
| | 200 | 5 | 41.7* | 40.9* | 38.9* | 39.6* | 42.0* | 37.1* |
| | 100 | 5 | 31.4* | 33.0* | 26.6* | 33.6* | 30.3* | 28.3* |
| 1A:2M | 300 | 5 | 53.3* | 54.3* | 46.3* | 54.8* | 53.8* | 43.6* |
| | 200 | 5 | 39.3* | 40.5* | 36.5* | 42.9* | 41.3* | 36.3* |
| | 100 | 5 | 25.2* | 26.8* | 24.2* | 31.8* | 31.3* | 28.8* |
| 1A:1M | 300 | 5 | 45.9* | 44.3* | 42.6* | 49.3* | 50.3* | 38.0* |
| | 200 | 5 | 36.8* | 39.5* | 36.1* | 37.3* | 39.4* | 30.8* |
| | 100 | 5 | 24.4* | 22.0* | 20.5* | 28.9* | 31.5* | 27.3* |

Data are presented as a percent change as compared to vehicle alone. Female Lewis rats (N = 5) were treated with ibuprofen (200 mg/kg), composition 1G1M, 1A2M or 1A1M (300 mg/kg, 200 mg/kg or 100 mg/kg), or vehicle alone an hour after carrageenan inoculation.
*$P \leq 0.001$ vs vehicle.

Example 59

Dose Correlated Analgesic and Anti-Inflammatory Activity of *Morus*-Based Compositions As described in Examples 57 and 58, mixed compositions of 1G:1M, 1A:2M and 1A:1M showed superior anti-inflammatory and analgesic activity over individual components G, A or M at a dose of 300 mg/kg. To determine the dose of compositions that would result in the most significant inhibition in pain and inflammation, each composition was tested at a dose of 300, 200 and 100 mg/kg in a carrageenan-induced rat paw edema model administered orally an hour post model induction. As seen in Table 41, a clear dose correlated, statistically significant, inhibition in hypersensitivity and inflammation was observed for all the compositions tested.

Example 60

Evaluation of Specific *Morus:Acacia* Composition in Carrageenan-Induced Rat Paw Edema Model Despite the fact that compositions 1G:1M, and 1A:2M of Examples 57 and 58 excelled in efficacy as analgesic and anti-inflammatory agents as compared to individual components G, A or M, a study using a carrageenan-induced rat paw edema model was conducted to evaluate the potential synergistic activity of components when formulated together at a specific ratios of 1G:1M and 1A:2M using Colby's method (Colby, 1967). When rats were given 1G:1M (10 wt % flavans, 1.5 wt % prenylated flavonoids, 1.5 wt % stilbenes) or 1A:2M (6.7 wt % flavans, 2 wt % prenylated flavonoids, 2 wt % stilbenes) compositions at a dose of 300 mg/kg, the observed results were greater than the theoretically calculated values both in inflammation and pain sensitivity at each time point analyzed (1, 3 or 5 hours after treatment) (Table 42).

TABLE 42

Analgesic and Anti-Inflammatory Activity of 1G:1M and 1A:2M Compositions

| Composition | Compound | Dose mg/kg | N | Percent change vs Vehicle ||||||
|---|---|---|---|---|---|---|---|---|---|
| | | | | Paw Edema ||| Pain Sensitivity |||
| | | | | 1 hr | 3 hr | 5 hr | 1 hr | 3 hr | 5 hr |
| 1G:1M | 1G* | 150 | 5 | 25.6 | 26.1 | 23.8 | 27.4 | 30.0 | 22.4 |
| | 1M | 150 | 5 | 30.6 | 29.6 | 24.2 | 30.1 | 31.5 | 23.0 |
| | Expected** | — | — | 48.4 | 48.0 | 42.2 | 49.2 | 52.0 | 40.2 |
| | Observed[¥] | 300 | 5 | 53.7 | 55.3 | 48.8 | 56.1 | 53.3 | 44.8 |
| 1A:2M | 1A | 100 | 5 | 21.9 | 23.0 | 17.6 | 23.9 | 27.5 | 22.6 |
| | 2M | 200 | 5 | 32.2 | 33.0 | 27.9 | 33.8 | 34.3 | 25.7 |
| | Expected** | — | — | 47.1 | 48.4 | 40.6 | 49.6 | 52.4 | 42.4 |
| | Observed[¥] | 300 | 5 | 53.3 | 54.3 | 46.3 | 54.8 | 53.8 | 43.6 |

Data are presented as a percent change as compared to vehicle alone. Rats (n = 5) were gavaged with composition 1G:1M or 1A:2M (300 mg/kg), G (150 mg/kg), A (100 and 150 mg/kg), M extract (150 and 200 mg/kg), or vehicle alone 1 hour after carrageenan-induced paw edema.
*G—*Uncaria gambir*, M—*Morus alba*, A—*Acacia catechu*.
**Expected: calculated value according to Colby's method = A − B, i.e., A = (C + M), B = (CM)/100.
[¥]Observed: data observed when a composition was orally administered at 300 mg/kg.

Clearly, the combination of a *Morus* ethanol extract with either an *Acacia* or Gambir extract yielded compositions with unexpected synergy and superior analgesic and anti-inflammatory efficacy.

Example 61

Effect of *Acacia* Extract on Ex Vivo GAG Release

Rabbit cartilage explants were cultured with rhIL-1α (5 ng/ml) in the absence or presence of *Acacia* extract 23, as prepared in Example 23, to examine the protective effects on proteoglycan (PG) degradation. *Acacia* extract was tested at four doses—25, 50, 100 and 200 µg/ml. *Acacia* extract interfered with the rhIL-1α-mediated degradation of PG in a dose dependent manner.

TABLE 43

Effect of *Acacia* Extract on Ex Vivo GAG Release

| Sample | Dose | % GAG release |
|---|---|---|
| (—) | — | 44.8 |
| IL-1α | 5 ng/ml | 100.0 |
| Diclofenac | 300 µg/ml | 26.5 |
| *Acacia* | 25 ug/ml | 90.6 |
|  | 50 ug/ml | 82.4 |
|  | 100 µg/ml | 73.8 |
|  | 200 µg/ml | 68.2 |

Example 62

Effect of Gambir (G):*Morus* (M) Compositions on Ex Vivo GAG Release

Rabbit cartilage explants were cultured for 24 hr with rhIL-1α (5 ng/ml) in absence or presence of composition of Gambir and *Morus* extract to examine the protective effects on PG degradation. The compositions were tested at two doses—100 and 200 µg/ml. As shown in the Table 44, all compositions of plant extracts prevented rhIL-1α mediated degradation of articular cartilage in a concentration dependent manner. The order of efficacy observed was 1G:2M>1G:1M>1G:4M>2G:1M>4G:1M.

TABLE 44

Effect of G:M Compositions on Ex Vivo GAG Release

| Sample | Dose | % GAG release |
|---|---|---|
| (—) | — | 44.8 |
| IL-1α | 5 ng/ml | 100.0 |
| Diclofenac | 300 µg/ml | 26.5 |
| 1G:1M | 100 µg/ml | 60.6 |
|  | 200 µg/ml | 51.1 |
| 1G:2M | 100 µg/ml | 56.0 |
|  | 200 µg/ml | 40.2 |
| 1G:4M | 100 µg/ml | 66.5 |
|  | 200 µg/ml | 51.2 |
| 2G:1M | 100 µg/ml | 72.7 |
|  | 200 µg/ml | 59.9 |
| 4G:1M | 100 µg/ml | 71.6 |
|  | 200 µg/ml | 65.9 |

Example 63

Evaluation of Gambir (G):*Morus* (M) Composition Synergy on Ex Vivo GAG Release

Rabbit cartilage explants were cultured for 24 hr with rhIL-1α (5 ng/ml) in the absence or presence of a Gambir extract: *Morus* extract mixed composition to examine the potential protective effect on PG degradation. The plant extracts from Gambir and Moms were produced according the above examples. The compositions were tested at two doses—100 and 200 µg/ml—to examine whether the combination showed synergistic effects. A composition of Gambir and *Morus* extract interfered with the rhIL-1α-mediated degradation of PG in a concentration dependent manner. Whether a synergistic effect was present was calculated by using the Colby formular (Colby, 1967). All five GM combinations 1G:1M (10 wt % flavans, 1.5 wt % prenylated flavonoids, 1.5 wt % stilbenes), 1G:2M (6.7 wt % flavans, 2 wt % prenylated flavonoids, 2 wt % stilbenes), 1G:4M (4 wt % flavans, 2.4 wt % prenylated flavonoids, 2.4 wt % stilbenes), 2G:1M (13.3 wt % flavans, 1 wt % prenylated flavonoids, 1 wt % stilbenes) and 4G:1M (16 wt % flavans, 0.6 wt % prenylated flavonoids, 0.6 wt % stilbenes) showed unexpected synergy at two doses.

TABLE 45

Synergistic Effect of G:M Compositions on Ex Vivo GAG Release

| Sample | Dose (µg/ml) | % Inhibition | Remark |
|---|---|---|---|
| 1G:1M | 100 | 62.8 | Theoretical value |
|  |  | 71.4 | Experimental result |
| G | 50 | 3.0 |  |
| M | 50 | 61.7 |  |
| 1G:1M | 200 | 71.8 | Theoretical value |
|  |  | 88.5 | Experimental result |
| G | 100 | 32.6 |  |
| M | 100 | 58.2 |  |
| 1G:2M | 100 | 41.3 | Theoretical value |
|  |  | 79.7 | Experimental result |
| G | 33.3 | 3.0 |  |
| M | 66.7 | 39.5 |  |
| 1G:2M | 200 | 55.7 | Theoretical value |
|  |  | 100 | Experimental result |
| G | 66.7 | 3.0 |  |
| M | 133.3 | 54.3 |  |
| 1G:4M | 100 | 54.8 | Theoretical value |
|  |  | 60.6 | Experimental result |
| G | 20 | 3.0 |  |
| M | 80 | 53.4 |  |
| 1G:4M | 200 | 71.6 | Theoretical value |
|  |  | 88.5 | Experimental result |
| G | 40 | 3.0 |  |
| M | 160 | 70.7 |  |
| 2G:1M | 100 | 32.7 | Theoretical value |
|  |  | 49.5 | Experimental result |
| G | 66.7 | 3.0 |  |
| M | 33.3 | 30.6 |  |
| 2G1M | 200 | 53.8 | Theoretical value |
|  |  | 72.7 | Experimental result |
| G | 133.3 | 23.6 |  |
| M | 66.7 | 39.5 |  |
| 4G:1M | 100 | 48.3 | Theoretical value |
|  |  | 51.4 | Experimental result |
| G | 80 | 25.5 |  |
| M | 20 | 30.6 |  |
| 4G:1M | 200 | 50.5 | Theoretical value |
|  |  | 61.8 | Experimental result |
| G | 160 | 14.7 |  |
| M | 40 | 42.0 |  |

A confirmatory study of 1G:1M and 1G:2M at 50, 100 and 200 µg/ml was carried out to validate the unexpected synergistic effect of two individual extracts being combined. The individual extracts used in the mixed compositions were tested at concentrations that were in proportion to the weight content of those extracts in the mixed compositions. Gambir and *Morus* extracts interfered with the rhIL-1α-mediated degradation of PG in a concentration dependent manner.

Synergistic effect was calculated by using Colby formular (Colby, 1967). Both 1G:1M and 1G:2M compositions demonstrated unexpected synergy at all three dosages.

TABLE 46

Synergy of G:M Combinations on Ex Vivo GAG Release

| Sample | Dose (ug/ml) | % Inhibition | Remark |
| --- | --- | --- | --- |
| 1G:1M | 50 | 27.6 | Theoretical value |
|  |  | 41.5 | Experimental result |
| G | 25 | 18.7 |  |
| M | 25 | 11 |  |
| 1G:1M | 100 | 72.5 | Theoretical value |
|  |  | 67.2 | Experimental result |
| G | 50 | 50.8 |  |
| M | 50 | 44.2 |  |
| 1G:1M | 200 | 45 | Theoretical value |
|  |  | 88.7 | Experimental result |
| G | 100 | 0 |  |
| M | 100 | 45 |  |
| 1G:2M | 50 | 54.4 | Theoretical value |
|  |  | 49.4 | Experimental result |
| G | 16.7 | 28 |  |
| M | 33.3 | 36.7 |  |
| 1G:2M | 100 | 60 | Theoretical value |
|  |  | 60.4 | Experimental result |
| G | 33.3 | 37.4 |  |
| M | 66.7 | 36.1 |  |
| 1G:2M | 200 | 79 | Theoretical value |
|  |  | 96.4 | Experimental result |
| G | 66.7 | 12.6 |  |
| M | 133.3 | 76 |  |

Example 64

Effect of *Curcuma* (C):Gambir (G):*Morus* (M) Composition On Ex Vivo GAG Release Rabbit cartilage explants were cultured for 24 hr with rhIL-1α (5 ng/ml) in absence or presence of composition of *Curcuma, Uncaria*, and *Morus* extracts to examine the protective effects on PG degradation. The compositions were tested at two doses—50 and 100 μg/ml. The individual extracts in the compositions were tested at concentrations that were in proportions of the weight contents of those extracts in the compositions. As shown in the Table 47, the composition of plant extracts prevented with the rhIL-1α mediated degradation of articular cartilage in a concentration dependent manner.

TABLE 47

Effect of C:G:M Compositions on Ex Vivo GAG Release

| Sample | Dose | % GAG release |
| --- | --- | --- |
| (—) | — | 44.8 |
| IL-1α | 5 ng/ml | 100.0 |
| Diclofenac | 300 μg/ml | 26.5 |
| 1C:2G:1M | 50 μg/ml | 82.1 |
|  | 100 μg/ml | 73.0 |

Example 65

Effect of *Acacia* (A):*Morus* (M) Compositions on Ex Vivo GAG Release

Rabbit cartilage explants were cultured with rhIL-1α (5 ng/ml) in absence or presence of composition of *acacia* and *morus* extract to examine the protective effects on PG degradation. The compositions were tested at two doses—100 and 200 ug/ml. As shown in the Table 48, all compositions of plant extracts prevented the rhIL-1α mediated degradation of articular cartilage.

TABLE 48

Effect of A:M Compositions on Ex Vivo GAG Release

| Sample | Dose | % GAG release |
| --- | --- | --- |
| (—) |  | 52.2 |
| IL-1α | 5 ng/ml | 100.0 |
| Diclofenac | 300 μg/ml | 42.2 |
| 1A:1M | 100 μg/ml | 66.8 |
|  | 200 μg/ml | 54.8 |
| 1A:2M | 100 μg/ml | 66.4 |
|  | 200 μg/ml | 65.4 |
| 1A:4M | 100 μg/ml | 70.5 |
|  | 200 μg/ml | 62.5 |
| 2A:1M | 100 μg/ml | 65.5 |
|  | 200 μg/ml | 66.2 |
| 4A:1M | 100 μg/ml | 71.6 |
|  | 200 μg/ml | 68.6 |

Example 66

Evaluation of *Acacia* (A):*Morus* (M) Composition Synergy on Ex Vivo GAG Release Rabbit cartilage explants were cultured for 24 hr with rhIL-1α (5 ng/ml) in the absence or presence of composition of *acacia* and *Morus* extract to examine the protective effects on PG degradation. The plant extracts from *Acacia* and *Morus* were produced according to the above examples. The compositions were tested at two doses—50 and 100 μg/ml—to examine whether the combined extracts together produce a unexpected synergistic effect on cartilage protection. The individual extracts in the compositions were tested at concentrations that were in proportion to the weight content of those extracts in the mixed compositions. *Acacia* and *Morus* extracts interfered with the rhIL-1α-mediated degradation of PG in a concentration dependent manner. Synergy was calculated by using the Colby formular (Colby, 1967). Both 1A:1M (10 wt % flavans, 1.5 wt % prenylated flavonoids, 1.5 wt % stilbenes) and 1A:2M (6.7 wt % flavans, 2 wt % prenylated flavonoids, 2 wt % stilbenes) demonstrated unexpected synergy in two doses.

TABLE 49

Synergistic Effect of A:M Compositions on Ex Vivo GAG Release

| Sample | Dose (ug/ml) | % Inhibition | Remark |
| --- | --- | --- | --- |
| 1A:1M | 50 | 28.4 | Theoretical value |
|  |  | 29.9 | Experimental result |
| A | 25 | 19.6 |  |
| M | 25 | 11 |  |
| 1A:1M | 100 | 64.7 | Theoretical value |
|  |  | 69.6 | Experimental result |
| A | 50 | 36.8 |  |
| M | 50 | 44.2 |  |
| 1A:2M | 50 | 65.6 | Theoretical value |
|  |  | 63.0 | Experimental result |
| A | 16.7 | 45.7 |  |
| M | 33.3 | 36.7 |  |
| 1A:2M | 100 | 53.4 | Theoretical value |
|  |  | 70.5 | Experimental result |
| A | 33.3 | 27.0 |  |
| M | 66.7 | 36.1 |  |

Example 67

Joint Protection Function of Compositions on In Vivo MIA (Monosodium Iodoacetate) Induced Osteoarthritis (OA) Rat Model The animals were randomized and assigned to treatment groups before the study began. After anesthetization with isoflurane, rats were injected with 50 μl containing 1 mg Monosodium iodoacetate (Sigma, St. Louis, Mo.; lot #SLBB6147V) using a 26 gauge needle inserted through the patellar ligament into the intra-articular space of the right knee. Normal rats were injected with an equivalent volume of saline instead of MIA. Animals were treated orally with Celecoxib 100 mg/kg, Diclofenac 5 mg/kg, Univestin® (Scutellaria:Acacia extract mixture) 400 mg/kg, 1C:1M 600 mg/kg and 1C:1M:2NAG 600 mg/kg once a day for 4 weeks. The first sample treatment was administered 1 hr before MIA injection. Normal and control rats were given orally an equal volume of vehicle (0.5% CMC in saline). Body weight and allodynia were measured once a week for 4 weeks. Allodynia was evaluated by measuring responsiveness to a tip of Randall-Selitto test (2390 series, IITC, Woodland Hills, Calif.) applied perpendicular to the central plantar surface of the right hind paw. Three animals in each group were evaluated for structural alterations of articular cartilage surface and subchondral bone architecture by Micro CT scan (SkyScan1173, Belgium). Histological changes were assessed to confirm the protection effect on cartilage degeneration in the knee joints of OA rats. After decalcification, joint tissues were stained with hematoxylin and eosin (HE), and also Safranin O-fast green to enable evaluation of proteoglycan content.

Example 68

Organic Extracts of Prenylated Flavonoids

Prenylchalcone, prenylflavones, prenylflavonols and prenylflavanones all belong to prenylflavonoids. Prenylated flavonoids have limited distribution in the plant kingdom. Many prenylated flavonoids have been found in the Moraceae family, but they are also disseminated in other families, such as Canabaceae, Fabaceae, Meliaceae, Rutaceae, Platanaceae, Cecropiaceae, Mimosaceae, Asclepiadaceae, Scrophulariaceae, Gesneriaceae, Asteraceae, and Zingiberaceae. The prenyl isoflavonoids are more restricted to subfamilies of the Leguminosae family.

Five different genera of plants reported to contain prenylated flavonoids were selected for extraction, as shown in Table 50. A total of 20 grams ground powder of each plant was loaded into a 100 ml stainless steel tube and extracted twice with an organic solvent mixture (methylene chloride/methanol in a ratio of 1:1) using an ASE 350 automatic extractor at 80° C. and under 1,500 psi of pressure. The extract solution was automatically filtered and collected. The combined organic extract solution was evaporated with a rotary evaporator to give a crude organic extract (OE). The organic extracts of the eight plants were tested in the GAG release assay described herein.

TABLE 50

Prenylated flavonoid Yield from Selected Plants

| SAMPLE_ID | FAMILY | GENUS | SPECIES | PARTS | NB_ID | Extraction YIELD |
|---|---|---|---|---|---|---|
| P00288 | Fabaceae | Sophora | Flavescens | root | P00288-OE | 22.6% |
| P00309 | Fabaceae | Psoralea | Corylifolia | fruit | P00309-OE | 11.5% |
| P00572 | Fabaceae | Glycyrrhiza | Glabra | rhizome-root | P00572-OE | 29.2% |
| P00635 | Cannabaceae | Humulus | Lupulus | flower | P00635-OE | 48.5% |
| P01302 | Cannabaceae | Humulus | Americanus | flower-leaf-vin | P01302-OE | 18.2% |
| P01962 | Fabaceae | Millettia | Usaramensis | root | P01962-OE | 6.3% |
| P01963 | Fabaceae | Millettia | Usaramensis | bark | P01963-OE | 8.4% |
| P01964 | Fabaceae | Millettia | Oblata | leaf | P01964-OE | 8.2% |

Xanthohumol and isoxanthohumol, which are prenylated chalcones and flavanones from hops (cones of Humulus lupulus), were reported as major and active compounds of the plants. Glabridin is one of the major prenylated flavonoids specifically reported from Glycyrrhiza glabra. Cathayanon A is a Diels-Alder adduct isolated from Milicia excelsa. These four prenylated flavonoids were obtained from commercial sources and tested in the GAG release assay.

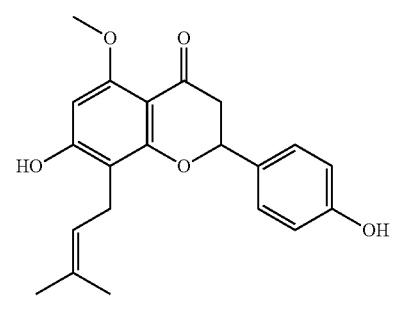

Isoxanthuhomol

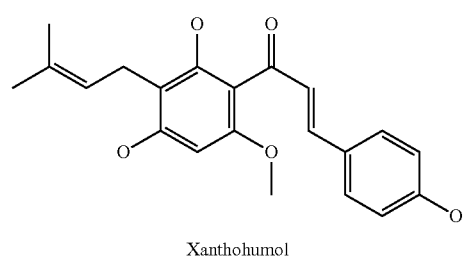

Xanthohumol

-continued

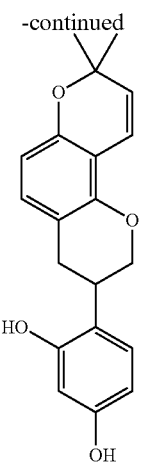
Glabridin

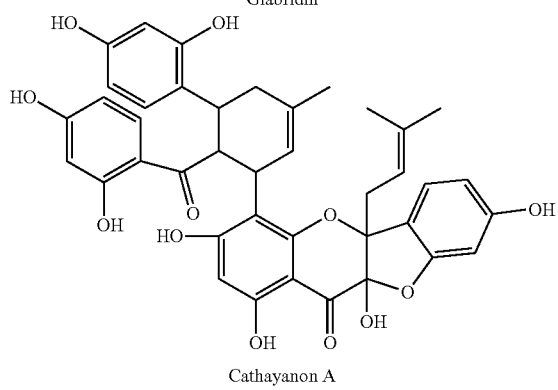
Cathayanon A

Example 69

Effect of Various Organic Extracts on Ex Vivo GAG Release

Organic extracts generated from five different plant genera as described in previous Example 68 were tested at three doses—50 µg/ml, 100 µg/ml, and 200 µg/ml—in the GAG release model as described in Example 27. As shown in Table 51, every extract tested inhibited ex vivo GAG release. In particular, organic extracts from *Sophora, Psoralea, Glycyrrhiza* and *Humulus* showed a strong cartilage protective effect as reflected by a reduction in GAG release, whereas the *Millettia* extract, while inhibiting GAG release, showed a weaker efficacy by comparison.

TABLE 51

| Effect of Various Organic Extracts on Ex Vivo GAG Release | | |
|---|---|---|
| Sample | Dose (µg/ml) | % GAG release |
| Negative control | — | 53.0 |
| IL-1α | 0.005 | 100.0 |
| Diclofenac | 300 | 19.6 |
| P00288 (*Sophora*) | 50 | 68.6 |
|  | 100 | 48.9 |
|  | 200 | 50.7 |
| P00309 (*Psoralea*) | 50 | 66.4 |
|  | 100 | 57.3 |
|  | 200 | 45.4 |
| P00572 (*Glycyrrhiza*) | 50 | 56.7 |
|  | 100 | 38.1 |
|  | 200 | 43.6 |

TABLE 51-continued

| Effect of Various Organic Extracts on Ex Vivo GAG Release | | |
|---|---|---|
| Sample | Dose (µg/ml) | % GAG release |
| P00635 (*Humulus*) | 50 | 46.7 |
|  | 100 | 39.5 |
|  | 200 | 34.9 |
| P01302 (*Humulus*) | 50 | 84.9 |
|  | 100 | 69.8 |
|  | 200 | 54.1 |
| P01962 (*Millettia*) | 50 | 87.7 |
|  | 100 | 86.1 |
|  | 200 | 84.8 |
| P01963 (*Millettia*) | 50 | 108.8 |
|  | 100 | 105.7 |
|  | 200 | 94.8 |
| P01964 (*Millettia*) | 50 | 113.2 |
|  | 100 | 109.4 |
|  | 200 | 80.0 |

Example 70

Effect of Purified Prenylated Flavonoids on Ex Vivo GAG Release

Four different prenylated flavonoids (glabridin, Compound 14; xanthohumol, Compound 13; isoxanthohumol, Compound 14; and cathayanon A, Compound 15), purified as described in Example 68, were tested in the ex vivo GAG release model as described in Example 27. Rabbit cartilage explants were cultured with rhIL-1α (5 ng/ml) in the absence or presence of each purified prenylated flavonoid compound to examine the protective effects on cartilage degradation. Each purified prenylated flavonoid was tested at four concentrations—6.25 µg/ml, 12.5 µg/ml, 25 µg/ml and 50 µg/ml.

TABLE 52

| Effect of Prenylated Flavonoids on Ex Vivo GAG Release | | |
|---|---|---|
| Sample | Dose (µg/ml) | % GAG release |
| (—) |  | 48.9 |
| IL-1α | 0.005 | 100.0 |
| Diclofenac | 300 | 38.0 |
| Glabridin | 6.25 | 66.1 |
|  | 12.5 | 47.9 |
|  | 25 | 47.5 |
|  | 50 | 46.3 |
| Xanthohumol | 6.25 | 77.4 |
|  | 12.5 | 55.3 |
|  | 25 | 59.2 |
|  | 50 | 51.2 |
| Isoxanthohumol | 6.25 | 97.8 |
|  | 12.5 | 73.5 |
|  | 25 | 41.7 |
|  | 50 | 37.3 |
| Cathayanon A | 6.25 | 101.4 |
|  | 12.5 | 99.1 |
|  | 25 | 81.3 |
|  | 50 | 72.4 |

As shown in Table 52, all four prenylated flavonoids inhibited rhIL-1α-mediated degradation of cartilage in a dose dependent manner.

Example 71

In Vivo Anti-Nociceptive Efficacy of a Gambir:*Morus* Composition in a Mouse Writhing Model Composition containing the extracts of Gambir:*Morus* at a ratio of 1:1 by weight (1G:1M) was tested at doses of 400 mg/kg, 300 mg/kg and 200 mg/kg to alleviate a visceral pain inflicted by the intraperitoneal administration of 0.7% of freshly prepared acetic acid in CD-1 mice. CD-1 mice (N=6) were orally gavaged with ibuprofen (200 mg/kg), 1G:1M (400, 300 or 200 mg/kg), or vehicle 30 minutes before intraperitoneal administration of freshly made acetic acid solution (0.7% in 0.9% NaCl) at 10 ml/kg. Immediately after injection of the irritant, animals showed abdominal constrictions consisting of contractions of the abdominal muscle which progressed posteriorly and ended with simultaneous flexor extension of both hind limbs with arching of the back. These behavioral responses observed for the duration of 30 minutes.

TABLE 53

Effect of 1G:1M Composition on Visceral Pain Sensitivity

| Group | Dose (mg/kg) | Mean ± SD. | % Inhibition | P Value |
|---|---|---|---|---|
| Vehicle | 0 | 77.4 ± 18.7 | — | — |
| Ibuprofen | 200 | 25.3 ± 14.3 | 67.4 | 0.0003 |
| 1G:1M | 400 | 42.2 ± 24.0 | 45.5 | 0.0176 |
|  | 300 | 50.5 ± 17.6 | 34.8 | 0.0279 |
|  | 200 | 65.7 ± 17.2 | 15.2 | 0.2836 |

The behavioral responses were found to be reduced to 42.2±24.0, 50.5±17.6 and 65.7±17.2 by oral administration of 1G:1M at doses of 400, 300 and 200 mg/kg, respectively, as compared to that of the vehicle control, i.e., 77.4±18.7 (Table 54). The positive control ibuprofen showed 25.3±14.3 or 67.4% reduction of the pain behavior. The reduction in pain sensitivity was statistically significant for both ibuprofen and 1G:1M (at doses of 400 mg/kg and 300 mg/kg) when compared to vehicle control.

Example 72

In Vivo Anti-Nociceptive Efficacy of an Acacia:*Morus* Composition in a Mouse Writhing Model A composition containing extracts of *Acacia:Morus* blended at a ratio of 1:2 by weight (1A:2M) was tested at doses of 300 mg/kg, 200 mg/kg and 100 mg/kg for the ability to alleviate visceral pain inflicted by intraperitoneal administration of acetic acid. CD-1 mice (n=6) were orally gavaged with ibuprofen (200 mg/kg), 1A:2M (300, 200 or 100 mg/kg), or vehicle alone 30 minutes before intraperitoneal administration of freshly prepared acetic acid solution (0.7% in 0.9% NaCl) at 10 mL/kg. Immediately after injection of the irritant, animals showed abdominal constrictions consisting of contractions of the abdominal muscle, which progressed posteriorly and ended with simultaneous flexor extension of both hind limbs with arching of the back. These behavioral responses were observed for 30 minutes.

TABLE 54

Effect of 1A:2M Composition on Visceral Pain Sensitivity

| Group | Dose (mg/kg) | Mean ± SD. | % Inhibition | P Value |
|---|---|---|---|---|
| Vehicle | 0 | 77.5 ± 16.3 | — | — |
| Ibuprofen | 200 | 41.8 ± 12.6 | 46.0 | 0.0016 |
|  | 300 | 50.8 ± 17.2 | 34.4 | 0.0197 |
| 1A:2M | 200 | 54.3 ± 15.5 | 29.9 | 0.0294 |
|  | 100 | 64.0 ± 11.5 | 17.4 | 0.1256 |

The behavioral responses were found to be reduced to 50.8±17.2, 54.3±15.5 and 64.0±11.5 after oral administration of 1A:2M at doses of 300, 200 and 100 mg/kg, respectively, as compared to the vehicle control, i.e., 77.5±16.1 (Table 54). The positive control ibuprofen showed 41.8±12.6 or 46.0% reduction of pain behavior. The reduction in pain sensitivity was statistically significant for both ibuprofen and 1A:2M (at doses of 300 mg/kg and 200 mg/kg) when compared to the control of vehicle alone.

Example 73

Effect of *Curcuma:Morus* Compostions on Pain and Inflammation in an Adjuvant-Induced Arthritis (AIA) Rat Model Adjuvant-induced arthritis (AIA) in rats is one of the most widely used experimental animal models of inflammatory joint conditions with clinical and pathological features similar to rheumatoid arthritis shared by many higher animals. It is characterized by chronic inflammation of multiple joints associated with subsequent progressive, erosive destruction of articular bone and cartilage, mononuclear cell infiltration, pannus formation and functional impairment (Wooley, *Curr. Rheumatol. Rev.* 4:277, 2008; Bolon et al., *J. Biomed. Biotechnol.* 2011:569068, 2011).

Use of a complete adjuvant as an antigen to induce a disease model of arthritis in rats was found to elicit two intertwined phases of the immune response that lead to inflammation. The primary reaction is an acute inflammation mediated partially through the COX/LOX pathways (on day 0 through day 8) at the site of inoculation, which was followed by a more delayed and complex secondary systemic reaction as a result of a generalized immunologic burst (on days 9 through 14) against antigen that triggers both cellular and humoral responses in association with TNF-α, IL1-β and NF-κB (Newbould, Br. *J. Pharmacol. Chemother.* 21:127, 1963). Therefore, anti-inflammatory agents that inhibit either immune response or pro-inflammatory pathways will show efficacy in this AIA model measured by edema or ankle diameter and pain sensitivity.

This adjuvant-induced rat arthritis model was used to evaluate the anti-pain and anti-inflammatory activity of a *Curcuma:Morus* (C:M) composition. Purpose bred female Wistar rats weighing 150-175 g (Charles River Laboratories, Inc., Wilmington, Mass.) were acclimated upon arrival for a week before being assigned randomly to their respective group. The rats were provided with fresh water and rodent chow diet ad libitum while being housed in a temperature controlled room (22.2° C.) on a 12 hour light-dark cycle. Treatment was started a day before antigen inoculation, wherein animals (n=9) were orally gavaged with a positive control ibuprofen, a 1C:1M test article, or a vehicle only control (propylene glycol). On the next day, arthritis was induced by sensitizing rats with an injection of complete Freund's adjuvant containing 5 mg/ml (w/v) suspension of heat killed *Mycobacterium tuberculosis* in liquid paraffin into the subplantar region of right hind paw of sedated rats (Currey, *Ann. Rheum. Dis.* 29:314, 1970; Whitehouse et al., *Can. Med. Assoc. J.* 129:249, 1983) an hour after a second treatment dose.

Anti-Inflammatory Activity—Paw Edema Measurement

Treatment with the controls or test articles was started a day before intraplantar injection of complete adjuvant into the right hind paw. The anti-inflammatory effect of a C:M composition was reflected in the measured change in paw edema. Rats (n=9) were treated orally with 1C:1M composition (200 mg/kg, 100 mg/kg or 50 mg/kg), ibuprofen (100 mg/kg) or vehicle for 14 days. Data are expressed as mean±SD and p-values were calculated against vehicle. Paw edema was measured with the use of a plethysmometer (IITC, Woodland Hills, Calif.; Model 520) on day 1 (before antigen), day 3, 5, 7, 9 and 13 after antigen injection.

The AIA model showed cardinal signs of inflammation (including hyperalgesia, swelling and hyperemia) were evident in all animals 24 hours post-priming with antigen. Rats treated with the positive control (ibuprofen) showed a statistically significant reduction in paw edema of 28.8%, 21.1%, 19.4%, 24.3% and 32.7% on days 3, 5, 7, 9 and 13, respectively, as compared to vehicle control. Animals treated with an oral dose of C:M compositions showed a reduction in paw edema as compared to the vehicle control animals on days 3, 5, 7, 9 and 13, respectively, of (a) 24.0%, 32.1%, 30.6%, 38.5% and 48.4% at a dose of 200 mg/kg, (b) 21.8%, 29.3%, 25.0%, 33.7% and 38.8% at a dose of 100 mg/kg, and (c) 15.6%, 17.1%, 18.8%, 27.1% and 38.2% at a dose of 50 mg/kg (Table 55). These percentage reductions were statistically significant at each time point analyzed.

TABLE 55

Effect of C:M Compostion on Paw Edema in AIA Model

| Groups | Day 3 Mean ± SD | P-Value | Day 5 Mean ± SD | P-Value | Day 7 Mean ± SD | P-Value | Day 9 Mean ± SD | P-Value | Day 13 Mean ± SD | P-Value |
|---|---|---|---|---|---|---|---|---|---|---|
| Vehicle | 5 ± 0.6 | — | 3.9 ± 0.4 | — | 3.8 ± 0.7 | — | 3.6 ± 0.6 | — | 3.1 ± 0.6 | — |
| Ibuprofen 100 mg/kg | 3.5 ± 0.7 | 0.0003 | 3.1 ± 0.8 | 0.0007 | 3.1 ± 0.7 | 0.0067 | 2.7 ± 0.6 | 0.0041 | 2.1 ± 0.58 | 0.0016 |
| C:M 200 mg/kg | 3.8 ± 0.3 | 0.0001 | 2.7 ± 0.4 | 0 | 2.7 ± 0.5 | 0.0005 | 2.2 ± 0.4 | 0 | 1.6 ± 0.4 | 0 |
| C:M 100 mg/kg | 3.9 ± 0.3 | 0.0002 | 2.8 ± 0.2 | 0 | 2.9 ± 0.4 | 0.0013 | 2.4 ± 0.3 | 0 | 1.9 ± 0.3 | 0.0001 |
| C:M 50 mg/kg | 4.2 ± 0.3 | 0.0003 | 3.3 ± 0.4 | 0.0020 | 3.1 ± 0.3 | 0.0079 | 2.6 ± 0.5 | 0.0007 | 1.9 ± 0.5 | 0.0002 |

The positive control showed greater inhibition of inflammation after 3 days of daily oral treatment as compared to any of the test compositions, but the degree of inhibition observed for the test compositions increase beyond the positive control as treatment days extended to day 13. These results indicate the C:M composition compounds may persist during this treatment regimen, which means a lower dose of C:M compositions may be used for chronic inflammation management and treatment.

Anti-Pain Activity—Allodynia Mesurement

Treatment with the controls or test articles was started a day before intraplantar injection of complete adjuvant into the right hind paw. The anti-pain effect of a C:M composition was reflected by allodynia (induced pain). Rats (n=9) were treated orally with 1C:1M composition (200 mg/kg, 100 mg/kg or 50 mg/kg), ibuprofen (100 mg/kg) or vehicle for 14 days. Data are expressed as mean±SD and p-values were calculated against vehicle. Allodynia was evaluated by responsiveness to pressure applied perpendicular to the central plantar surface of the right hind paw using the Randall-Selitto test (Randall and Selitto, *Arch. Intl Pharmacodyn Therap.* 133:233, 1957). A positive response to the applied mechanical pressure, noted by sharp withdrawal of the paw, was recorded automatically by an electronic Von Frey Anesthesiometer (2390 series Electrovonfrey, IITC, Woodland Hills, Calif.) (Vivancos et al., 2004). Mechanically induced allodynia was evaluated before antigen treatment, and then on days 3, 5, 7, 9 and 13 after antigen injection.

Oral administration of a C:M composition and ibuprofen showed a marked reduction in pain sensitivity. As shown in Table 56, a statistically significant reduction in pain sensitivity was observed when rats were treated with 100 mg/kg of ibuprofen (31.3%, 39.5%, 48.8%, 52.5% and 52.5% reductions on day 3, 5, 7, 9 and 13, respectively). The pain sensitivity inhibitions of orally gavaged C:M composition at a dose of 200 mg/kg were 27.1%, 38.2%, 51.6%, 52.8% and 54.2%, at a dose of 100 mg/kg were 25.6%, 34.9%, 39.0%, 47.6% and 46.2%, and at a dose of 50 mg/kg were 21.8%, 24.3%, 29.0%, 37.6% and 40.8% (Table 56).

TABLE 56

Effect of C:M Compostion on Allodynia in AIA Model

| Groups | Day 3 Mean ± SD | P-Value | Day 5 Mean ± SD | P-Value | Day 7 Mean ± SD | P-Value | Day 9 Mean ± SD | P-Value | Day 13 Mean ± SD | P-Value |
|---|---|---|---|---|---|---|---|---|---|---|
| Vehicle | 98.2 ± 6.3 | — | 90.7 ± 5.4 | — | 84.0 ± 2.9 | — | 81.6 ± 3.6 | — | 69.3 ± 3.5 | — |
| Ibuprofen 100 mg/kg | 67.4 ± 5.6 | 0 | 54.8 ± 2.6 | 0 | 43.0 ± 4.6 | 0 | 38.8 ± 2.3 | 0 | 32.9 ± 2.6 | 0 |
| C:M 200 mg/kg | 71.6 ± 3.6 | 0 | 56.0 ± 2.0 | 0 | 40.7 ± 4.9 | 0 | 38.5 ± 1.7 | 0 | 31.7 ± 2.7 | 0 |
| C:M 100 mg/kg | 73.1 ± 3.7 | 0 | 59.1 ± 2.6 | 0 | 51.2 ± 3.6 | 0 | 42.8 ± 3.2 | 0 | 37.3 ± 1.0 | 0 |
| C:M 50 mg/kg | 76.8 ± 5.4 | 0 | 68.7 ± 2.7 | 0 | 59.6 ± 1.8 | 0 | 50.9 ± 4.1 | 0 | 41.1 ± 2.1 | 0 |

These data make clear that ibuprofen (positive control) showed the strongest analgesic activity by day 3, but C:M compositions at 100 mg/kg or 50 mg/kg were stronger thereafter. Nevertheless, coinciding with the paw edema data, activity of the composition at any of the doses administered were augmented as the treatment days were extended to day 13.

Anti-Inflammatory Activity—Ankle Width Mesurement

Treatment with the controls or test articles was started a day before intraplantar injection of complete adjuvant into the right hind paw. The anti-inflammatory effect of a C:M composition was reflected in the measured change in ankle diameter. Rats (n=9) were treated orally with 1C:1M composition (200 mg/kg, 100 mg/kg or 50 mg/kg), ibuprofen (100 mg/kg) or vehicle for 14 days. Data are expressed as mean±SD and p-values were calculated against vehicle Ankle diameter was measured using a Pocket Thickness Gage (7309, Mitutoyo corp. Japan) on day 1 (before antigen), day 3, 5, 7, 9 and 13 after antigen injection.

As shown in Table 57, a greater reduction in ankle diameter reduction support the harmonized effect of C:M composition in reducing inflammation in a joint. Animals treated with an oral dose of 200 mg/kg C:M showed 43.1%, 47.3%, 45.5%, 52.4 and 60.9% reduction, with an oral dose of 100 mg/kg showing a 35.9%, 39.0%, 39.2%, 42.0% and 51.9% reduction, and with an oral dose of 50 mg/kg showing a 30.9%, 32.2%, 34.1%, 36.5% and 48.7% reductions in ankle diameter on days 3, 5, 7, 9 and 13, respectively, as compared to vehicle control treated animals. These percentage reductions were statistically significant at each time point analyzed. The positive control ibuprofen showed statistically significant 37.2%, 34.8%, 36.8%, 33.5% and 44.2% reduction in ankle diameter on days 3, 5, 7, 9 and 13, respectively, compared to vehicle control (Table 57).

TABLE 57

Effect of C:M Compostion on Ankle Width in AIA Model

| Groups | Day 3 Mean ± SD | P-Value | Day 5 Mean ± SD | P-Value | Day 7 Mean ± SD | P-Value | Day 9 Mean ± SD | P-Value | Day 13 Mean ± SD | P-Value |
|---|---|---|---|---|---|---|---|---|---|---|
| Vehicle | 1.7 ± 0.2 | — | 1.5 ± 0.2 | — | 1.8 ± 0.2 | — | 1.5 ± 0.2 | — | 1.4 ± 0.1 | — |
| Ibuprofen 100 mg/kg | 1.1 ± 0.1 | 0.0028 | 1.0 ± 0.1 | 0.0076 | 1.2 ± 0.1 | 0.0009 | 1.0 ± 0.2 | 0.0116 | 0.8 ± 0.1 | 0.0016 |
| C:M 200 mg/kg | 1.0 ± 0.1 | 0.0009 | 0.8 ± 0.1 | 0.0002 | 1.0 ± 0.1 | 0 | 0.7 ± 0.1 | 0 | 0.5 ± 0.1 | 0 |
| C:M 100 mg/kg | 1.1 ± 0.1 | 0.0057 | 0.9 ± 0.1 | 0.0028 | 1.1 ± 0.2 | 0.0020 | 0.9 ± 0.1 | 0.0003 | 0.7 ± 0.1 | 0 |
| C:M 50 mg/kg | 1.2 ± 0.1 | 0.0053 | 1.0 ± 0.1 | 0.0143 | 1.2 ± 0.2 | 0.0103 | 1.0 ± 0.2 | 0.0260 | 0.7 ± 0.2 | 0.0004 |

In this particular case, the C:M composition (at 200 mg/kg) showed the greatest inhibition of ankle swelling as compared to any other treatment group, including positive control ibuprofen, and at all time points monitored. In fact, rats treated with an oral dose of ibuprofen at 100 mg/kg was comparable to treatment with a C:M composition at 50 mg/kg in anti-inflammatory effect.

Example 74

*Curcuma:Morus, Acacia:Morus* and *Gambir:Morus* Compositions Inhibit COX-1 and COX-2 Enzyme Activity COX inhibition was tested using a colorimetric COX (ovine) inhibition assay kit (Cayman Chem., Co.). Briefly, 150 μl of assay buffer, 10 μl of heme, 10 μl of COX-1 or COX-2 enzyme and 20 μl of test material were added into 96-well plates. The plate was shaken carefully for a few seconds, incubated at 25° C. for 5 minutes, and then 20 μl colorimetric substrate solution and arachidonic acid were added to initiate the reaction. After shaking, the reaction was allowed to proceed for 10 minutes at 25° C. and then the absorbance of each well was measured at 590 nm using a plate reader.

TABLE 58

Effect of C:M, G:M, and A:M Compositions on COX-1/COX-2 Activity

| Dose (μg/ml) | % Inhibition of COX-1 | | | % Inhibition of COX-2 | | |
| --- | --- | --- | --- | --- | --- | --- |
| | C:M | G:M | A:M | C:M | G:M | A:M |
| 10 | 17.3 ± 0.23 | 36.3 ± 0.55 | 38.1 ± 0.67 | 14.3 ± 1.11 | 23.2 ± 1.35 | 23.7 ± 1.51 |
| 25 | 39.8 ± 0.35 | 64.9 ± 0.35 | 54.1 ± 0.74 | 19.7 ± 1.21 | 46.6 ± 0.44 | 46.0 ± 1.15 |
| 50 | 57.6 ± 0.06 | 78.8 ± 0.25 | 72.3 ± 0.64 | 35.8 ± 1.29 | 63.8 ± 0.26 | 51.9 ± 0.47 |
| 100 | 107.8 ± 0.61 | 90.5 ± 0.21 | 81.0 ± 0.35 | 63.6 ± 0.49 | 82.0 ± 0.15 | 72.7 ± 0.70 |
| $IC_{50}$ | 40.5 μg/ml | 12.4 μg/ml | 20.9 μg/ml | 74.1 μg/ml | 39.8 μg/ml | 49.2 μg/ml |

As shown in Table 58, $IC_{50}$ values of C:M, G:M and A:M compositions were 40.5, 12.4 and 20.9 μg/ml, respectively, in the COX-1 enzyme activity assay, and 74.1, 39.8 and 49.2 μg/ml, respectively, in COX-2 enzyme activity assay. All samples showed more potent effects in inhibition of COX-1 enzyme than inhibition of COX-2 enzyme, each in a dose-dependent manner.

Example 75

*Curcuma:Morus, Acacia:Morus* and *Gambir:Morus* Compositions Inhibit 5-Lipoxygenase Activity The effect on 5-lipoxygenase (5-LOX) was tested us a Lipoxygenase inhibitor screening assay kit (5-LOXs: potato; Cayman Chem., Co.). Briefly, 90 μl of 5-LOX enzyme and 10 μl of test materials were added into 96-well plates, carefully shaken for a few seconds, and then 10 μl linoleic acid was added to initiate the reaction. The plates were placed on a shaker for 5 minutes, and then 100 μl chromogen was added to each well to stop the enzyme reaction. To develop the reaction, the plates were placed on a shaker for 5 minutes and the absorbance of each well was then measured at 490 nm using a plate reader.

TABLE 59

Effect of C:M, G:M, and A:M Compositions on 5-LOX Activity

| | % Inhibition of 5-LOX Enzyme | | |
| --- | --- | --- | --- |
| Dose (μg/ml) | C:M | G:M | A:M |
| 10 | 25.7 ± 2.59 | 37.3 ± 1.93 | 41.4 ± 1.25 |
| 25 | 56.3 ± 1.04 | 77.7 ± 0.00 | 78.6 ± 0.40 |
| 50 | 75.3 ± 0.40 | 92.8 ± 0.36 | 93.4 ± 0.20 |
| $IC_{50}$ | 26.3 μg/ml | 13.6 μg/ml | 11.1 μg/ml |

As shown in Table 59, all samples showed more potent effect than that of 5-LOXIN and all three compositions showed a dose-dependent effect. The $IC_{50}$ values of C:M, G:M and A:M were 26.3, 13.6 and 11.1 μg/ml, respectively, in this 5-LOX enzyme activity assay.

Example 76

Anti-Nociceptive Effect of a *Gambir:Morus* Composition in a Mono-Iodoacetate (Mia)-Induced Osteoarthritis Rat Model Osteoarthritis (OA) is a degenerative joint disease characterized by joint pain and a progressive loss of articular cartilage and, to date, with no cure. As the disease advances, the biochemical alterations that occur within the articular cartilage will result in imbalances between anabolic and catabolic processes that ultimately alter the overall joint structure and function, and lead to chronic pain. Multiple animal models have been developed and utilized to study the pathogenesis of OA and to evaluate the effectiveness of novel therapeutic agents with limited success. An animal model with a robust induction and reproducibility of joint pathology, along with pain associated with the disease, was desired, so the minimally invasive mono-iodoacetate (MIA) induced OA model was employed. Mono-iodoacetate (MIA) is an inhibitor of glyceraldehyde-3-phosphate dehydrogenase activity shown to induce chondrocyte death and hence reproduces cartilage lesions with loss of proteoglycan matrix and functional joint impairment similar to human OA (Marker and Pomonis, *Methods Mol. Biol.* 851:239, 2012).

Male Sprague-Dawley (SD) rats weighing about 170 to about 230 g (6 weeks of age) were purchased and acclimated for one week. One day before disease induction, animals were randomized into four group as follows: G1 (Normal), G2 (Vehicle), G3 (Diclofenac; 10 mg/kg) and G4 (G:M; 500 mg/kg). Each group was orally gavaged with their respective treatment. Anesthetized rats were injected with 0.8 mg of MIA in a 50 μl saline solution into the intra-articular pocket one hour after the second dose of treatments. Pain sensitivity was measured once a week using a Randall-Salitto meter and treatment lasted for 6 weeks. Body weights were measured once a week to calculate the respective weekly dosage of each group. Once the in-life study was concluded, structural and cellular alterations of joint tissues as a result of disease progression and/or treatment efficacy was assessed by using histopathology with a modified Mankin scoring system.

TABLE 60

Inhibition of Pain Sensitivity by G:M Composition in an OA Model

| Group/Dose | | 0 | 1 | 2 | 3 | 4 | 5 | 6 |
|---|---|---|---|---|---|---|---|---|
| G1 (Normal) | Mean | 174.53 | 172.53 | 174.67 | 175.40 | 171.40 | 166.07 | 163.60 |
| | SD | 29.51 | 6.53 | 13.90 | 23.95 | 39.09 | 19.86 | 9.32 |
| | % | 100.00 | 98.85 | 100.08 | 100.50 | 98.20 | 95.15 | 93.74 |
| G2 (Vehicle) | Mean | 173.23 | 158.07 | 151.90 | 160.07 | 143.10 | 121.03 | 122.07 |
| | SD | 18.04 | 15.08 | 42.97 | 16.12 | 23.00 | 12.77 | 15.17 |
| | % | 100.00 | 91.24 | 87.69 | 92.40 | 82.61 | 69.87 | 70.46 |
| G3 (Diclofenac; | Mean | 173.20 | 146.37 | 155.67 | 162.90 | 150.90 | 146.23 | 144.23 |
| 10 mg/kg) | SD | 15.61 | 27.86 | 23.85 | 28.90 | 19.62 | 22.73 | 27.57 |
| | % | 100.00 | 84.51 | 89.88 | 94.05 | 87.12 | 84.43 | 83.28 |
| G4 (G:M; | Mean | 173.33 | 168.13 | 178.87 | 174.37 | 166.90 | 170.00 | 148.93 |
| 500 mg/kg) | SD | 17.44 | 22.68 | 57.83 | 26.48 | 27.17 | 21.13 | 26.12 |
| | % | 100.00 | 97.00 | 103.19 | 100.60 | 96.29 | 98.08 | 85.92 |
| P-values vs | G1 | 0.9311 | 0.0226 | 0.1535 | 0.2446 | 0.1907 | 0.0041 | 0.0000 |
| Vehicle | G3 | 0.9965 | 0.2626 | 0.8120 | 0.7905 | 0.4255 | 0.0085 | 0.0428 |
| | G4 | 0.9901 | 0.2600 | 0.2532 | 0.1655 | 0.0491 | 0.0000 | 0.0135 |

One of the cardinal symptoms of OA (i.e., pain) was apparent a week following model induction. As shown in Table 60, rats with an intra-articular injection of MIA showed a progressive increase in pain sensitivity as exhibited by the mean pain sensitivity values of untreated vehicle control with MIA. In contrast, rats treated with a dose of 500 mg/kg of G:M orally per day for 6 weeks showed statistically significant reductions in pain sensitivity after 4 weeks of oral treatment. A 16.6%, 40.5% and 22.0% reductions in pain sensitivity were observed for rats treated with 1G:1M (500 mg/kg) at week 4, week 5 and week 6, respectively. Diclofenac (positive control) showed significant reduction of pain sensitivity beginning week 5 and percentage reductions of 20.8% and 18.2% were observed in week 5 and week 6, respectively.

Example 77

Protection of Articular Cartilage by Gambir:Morus Composition

In the rat model of Example 76, articular cartilage matrix integrity was also measured. In agreement with the pain sensitivity reduction data in Example 76, statistically significant improvement in articular cartilage matrix integrity was found as reflected by the total Mankin score for animals treated with G:M at a dose of 500 mg/kg (Table 61). In contrast, the positive control, Diclofenac, while showing a positive trend, showed a change that was not statistically significant in the structure, cellular abnormality and matrix integrity, as compared to vehicle control (Table 61).

TABLE 61

Effect of G:M Composition on Histopatholical Scoring in OA Model

| Group (Dose) | Structure (0-6)* | Cellular Abnormality (0-3)† | Safranin-O Staining (0-4)‡ | Total Mankin Score |
|---|---|---|---|---|
| Normal | 0 | 0 | 0 | 0 |
| Vehicle | 2.78 ± 1.79 | 1.78 ± 0.44 | 2.67 ± 1.32 | 7.22 ± 3.19 |
| Diclofenac (10 mg/kg) | 1.9 ± 1.45 | 1.3 ± 0.67 | 1.7 ± 0.82 | 4.9 ± 2.69 |
| GM (500 mg/kg) | 1.0 ± 0* | 1.4 ± 0.52 | 1.3 ± 0.95* | 3.7 ± 1.33* |

*Structure Score (0-6): 0 = Normal; 1 = Irregular surface, including fissures in to the radial layer; 2 = pannus; 3 = Absence of superficial cartilage layers; 4 = Slight disorganization (an absent cellular row and some small superficial clusters); 5 = Fissures into the calcified cartilage layer; 6 = Disorganization (chaotic structure,clusters and oesteoclastic activity)
†Cellular abnormality Score (0-3): 0 = Normal; 1 = Hyper cellularity, including small superficial clusters; 2 = Clusters, 3 = Hypocellularity
‡Matrix (Safranin-O) Staining Score (0-4): 0 = Normal/slight reduction of staining; 1 = Staining reduced in the radial layer; 2 = Staining reduced in the interterritorial matrix; 3 = Staining reduce in pericellular matrix; 4 = Staining absent.

Example 78

Human Clinical Study of Combination Extracts from Curcuma, Uncaria, Acacia and Morus on Supporting Joint Functions In a human clinical trial, a double blind randomized placebo and positive comparator controlled trial will be carried out to examine the efficacy and safety of a mixture of C—Curcuma, G—Gambir or A—Acacia, and M—Morus in osteoarthritis (OA) patients. The study will evaluate change in pain severity on a 0-10 Numeric Rating Scale (visual analog scale, VAS), change in pain severity on the WOMAC scale, and change in physical functional and stiffness as measured by the WOMAC scale. Objective measures of improvement will be evaluated at baseline and end of study, range of motion by BIODEX and distance walked in six minutes plus safety evaluations are also included.

Before screening, subjects must read and sign the IRB approved Informed Consent Form. The study population will consist of male and female subjects older than 18 and less than 75 years and in generally good health as determined by a medical history. Female subjects of childbearing potential must have a negative urine pregnancy test at baseline. The goal of the study is to enroll sufficient subjects to treat 40 subjects per study arm.

A clear definition of OA as listed in Inclusion criteria: Male/Female healthy adult 18 to 75 years of age, inclusive, meet pain entry criteria, a history of knee joint pain for greater than 6 months, medial or lateral tibiofemoral joint line tenderness, unilateral knee pain 6/10 or greater, on average, on the visual analog scale (VAS), that interferes with function most days per week, and Kellgren grade II or III radiographic changes of osteoarthritis. Willingness to discontinue use of all analgesic medications (including over-the-counter [OTC] analgesics) except those provided as the study treatment and rescue medication specifically for study purposes Primary Objective
  Change in pain severity on a 0-10 Numeric Rating Scale, Change in Pain Severity on 0-10 cm VAS
  Change in Pain Severity on WOMAC Pain Subscale (0-100), Change in WOMAC Total Score all subscales.
Secondary Objectives Safety Assessments
  Patient global assessment of response to treatment, Physician global assessment of response to treatment
  Improvement in Physical Function and Stiffness subscale of the WOMAC and WOMAC
  Change in joint function as measured by active and passive range of motion, distance walked in the 6 minute walk test. QOL: generic health status measure, the SF-36 and specific health status measures, the WOMAC
Safety Evaluations:
  Complete Blood Count, Chemistry Panel with liver function tests, PT/INR, HCG and AE assessments will be performed.
Data Analysis
  In this study 120 subjects, randomized equally to receive Product 1, Product 2, or Placebo (40 subjects each). If the attrition rate is 30% from the per-protocol population over the course of the 12-week study, there should be approximately 21 analyzable subjects per group. A power analysis was carried out to determine the effect size (difference between products in mean 12-week changes of efficacy endpoints) that would provide an 80% chance of obtaining a significant result of $p<0.05$ with 21 analyzable subjects per group.

The statistical design parameters for this study are:
Alpha Level: 0.05 ($p<0.05$ considered statistically significant);
Power: 0.8 (an 80% chance of obtaining significant p value);
Primary Null Hypothesis: Mean 12-week change for any supplement will equal the 12-week change for Placebo
Alternate Hypothesis: Changes are not equal between products.
Statistical Test: Analysis of Covariance (power calculations based on unpaired Student t test);
Sample Size: 120 enrolled subjects, 40 in each product group;

TABLE 58

Study Procedures

| Procedure | Visit 1 | Visit 2 | Visit 3 | Visit 4 | Visit 5 | Visit 6 |
|---|---|---|---|---|---|---|
| Subject Visit | Screening | Day 0 | Day 14 | Day 30 | Day 60 | Day 90 Exit Visit |
| Timing | Day −14 | Day 0 | Day 14 ± 1 | Day 30 ± 1 | Day 60 ± 2 | Day 90 ± 2 |
| Informed Consent | X | | | | | |
| Inclusion/Exclusion | X | X | | | | |
| Continuance Criteria | | X | X | X | X | |
| Medical History | X | | | | | |
| Physical Exam | X | | | | | X |
| Demography | X | | | | | |
| Height | X | | | | | |
| Weight | X | X | X | X | X | X |
| Vital signs | X | X | X | X | X | X |
| Identify target joint | X | | | | | |
| Chemistry panel with LFT | X | | | X | X | X |
| CBC with differential, PT/INR | X | | | X | X | X |
| Collect blood samples for Cytokines | | X | | X | X | X |
| β-HCG Pregnancy Test | X | | | | | X |
| WOMAC pain subscale (5 items) | X | | | | | |
| Complete WOMAC 3 subscales | | X | X | X | X | |
| 100 mm VAS Scale Daily Assessment | | X | X | X | X | |
| Maximum Distance (feet) walked in 6 minutes | | X | | X | X | X |
| Concomitant Medications | X | X | X | X | X | X |

TABLE 58-continued

Study Procedures

| Procedure | Visit 1 | Visit 2 | Visit 3 | Visit 4 | Visit 5 | Visit 6 |
|---|---|---|---|---|---|---|
| Adverse Events/Intercurrent Illness | | | X | X | X | X |
| Dispense Rescue Medication | | X | | | | |
| Return Rescue Medication | | | X | X | X | X |
| Dispense Test Product | | X | | X | X | |
| Return Test Product | | | X | X | X | X |

The various embodiments described above can be combined to provide further embodiments. All of the U.S. patents, U.S. patent application publications, U.S. patent applications, foreign patents, foreign patent applications and non-patent publications referred to in this specification or listed in the Application Data Sheet are incorporated herein by reference, in their entirety. Aspects of the embodiments can be modified, if necessary to employ concepts of the various patents, applications and publications to provide yet further embodiments. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method for maintaining joint health in a mammal comprising:
providing an enriched *Morus* (M) extract from a plant material or other source, the extract having at least a two-fold up to about a 1000-fold increase in the amount or activity of one or more prenylated flavonoids as compared to the amount or activity of the one or more prenylated flavonoids found in the weight of the plant material or the other source before extraction or other preparation;
providing an enriched *Acacia* (A) extract from a plant material or other source; and
administering a composition comprising 300 mg/kg dose of a mixture of the enriched *Morus* extract and the *Acacia* extract, wherein the *Morus* extract is from *Morus alba*, and the *Acacia* extract is from *Acacia catechu*, wherein the *Morus* extract comprises Kuwanon G, Albanin G or a combination thereof, wherein the enriched *Morus* extract and the *Acacia* extract are blended in a 1A:1M weight ratio or a 1A:2M weight ratio, wherein the *Morus* extract comprises about 1.5-2 wt % of prenylated flavonoids, wherein the *Morus* extract comprises about 1.5-2 wt % of stilbenes, and wherein the *Acacia* comprises about 6.7-10 wt % flavans.

2. The method for maintaining joint health in a mammal of claim 1, wherein the enriched *Morus* extract from a plant material or other source, the extract having at least a two-fold up to about a 1000-fold increase in the amount or activity of one or more prenylated flavonoids, one or more stilbenes, or a combination thereof, as compared to the amount or activity of the one or more prenylated flavonoids, one or more stilbenes, or a combination thereof, found in the weight of the plant material or the other source before extraction or other preparation.

3. The method for maintaining joint health in a mammal of claim 1, wherein the *Acacia* extract is an enriched *Acacia* extract, wherein the enriched *Acacia* extract from a plant material or other source, the extract having at least a two-fold up to about a 1000-fold increase in the amount or activity of one or more flavans as compared to the amount or activity of the one or more flavans found in the weight of the plant material or the other source before extraction or other preparation.

4. The method for maintaining joint health in a mammal of claim 2, wherein the one or more prenylated flavonoids further comprises Morusin.

5. The method for maintaining joint health in a mammal of claim 2, wherein the one or more stilbenes comprises oxyresveratrol, mulberroside A, or a combination thereof.

6. The method for maintaining joint health in a mammal of claim 1, wherein the active ingredients in the *Acacia* extract are catechin, epicatechin, or a combination thereof.

7. The method of claim 1 wherein the composition additionally comprises a joint health management agent.

8. The method for maintaining joint health in a mammal of claim 7, wherein the joint health management agent comprises glucosamine sulfate, glucosamine hydrochloride, N-acetylglucosamine, chondroitin sulfate, methylsulfonylmethane, hyaluronic acid or a combination thereof.

9. The method for maintaining joint health in a mammal of claim 1, wherein the composition further comprises a pharmaceutically or nutraceutically acceptable carrier, diluent, or excipient, wherein the pharmaceutical or nutraceutical formulation comprises from about 0.5 weight percent to about 90 weight percent of active ingredients of the extract mixture.

10. The method for maintaining joint health in a mammal of claim 9, wherein the composition is formulated as a tablet, hard capsule, softgel capsule, powder, or granule.

* * * * *